(12) United States Patent
Dai et al.

(10) Patent No.: US 11,241,437 B2
(45) Date of Patent: Feb. 8, 2022

(54) HETEROCYCLIC COMPOUNDS, PREPARATION METHODS AND USES THEREOF

(71) Applicant: InventisBio Co., Ltd., Shanghai (CN)

(72) Inventors: Xing Dai, Shanghai (CN); Yueheng Jiang, Shanghai (CN); Yanqin Liu, Shanghai (CN)

(73) Assignee: INVENTISBIO CO., LTD., Shanghai (CN)

( * ) Notice: Subject to any disclaimer, the term of this patent is extended or adjusted under 35 U.S.C. 154(b) by 0 days.

(21) Appl. No.: 17/172,984

(22) Filed: Feb. 10, 2021

(65) Prior Publication Data

US 2021/0260067 A1    Aug. 26, 2021

Related U.S. Application Data

(63) Continuation of application No. PCT/CN2020/137276, filed on Dec. 17, 2020.

(30) Foreign Application Priority Data

Dec. 18, 2019 (WO) ............... PCT/CN2019/126230

(51) Int. Cl.
| | |
|---|---|
| C07D 487/04 | (2006.01) |
| A61K 31/505 | (2006.01) |
| A61P 35/00 | (2006.01) |
| A61K 31/519 | (2006.01) |
| A61K 45/06 | (2006.01) |
| C07D 471/04 | (2006.01) |

(52) U.S. Cl.
CPC ............ *A61K 31/519* (2013.01); *A61K 45/06* (2013.01); *C07D 471/04* (2013.01); *C07B 2200/13* (2013.01)

(58) Field of Classification Search
CPC ...... A61K 31/505; C07D 487/04; A61P 35/00
USPC ..................... 514/252.16; 544/279
See application file for complete search history.

(56) References Cited

U.S. PATENT DOCUMENTS

| | | |
|---|---|---|
| 10,519,146 B2 | 12/2019 | Lanman et al. |
| 10,532,042 B2 | 1/2020 | Lanman et al. |
| 10,640,504 B2 | 5/2020 | Lanman et al. |
| 2018/0334454 A1 | 11/2018 | Lanman et al. |
| 2019/0343838 A1 | 11/2019 | Allen et al. |
| 2019/0374542 A1 | 12/2019 | Allen et al. |
| 2020/0181118 A1 | 6/2020 | Malhotra et al. |
| 2020/0207766 A1 | 7/2020 | Lanman et al. |
| 2020/0222407 A1 | 7/2020 | Lipford et al. |

FOREIGN PATENT DOCUMENTS

| | | |
|---|---|---|
| CN | 108658972 A | 10/2018 |
| CN | 110256421 A | 9/2019 |
| CN | 111205286 A | 5/2020 |
| CN | 111377918 A | 7/2020 |
| WO | 2018119183 A2 | 6/2018 |
| WO | 2018217651 A1 | 11/2018 |
| WO | 2019051291 A1 | 3/2019 |
| WO | 2019213516 A1 | 11/2019 |
| WO | 2020097537 A2 | 5/2020 |

OTHER PUBLICATIONS

McCormick, F., KRAS as a Therapeutic Target, Clin Cancer Res., 21:1797-1801 (2015).
Simanshu, D. K., et al., RAS Proteins and Their Regulators in Human Disease, Cell, 170:17-33 (2017).
Liu, L. and Wei, S., Research Progress of KRAS Mutation in Non-small Cell Lung Cancer, Chin J Lung Cancer, 21 (5):419-424 (2018).
International Search Report and Written Opinion dated Feb. 24, 2020 in International Patent Application No. PCT/CN2019/087772, 13 pages.
International Search Report and Written Opinion dated Feb. 27, 2020 in International Patent Application No. PCT/CN2019/095947, 14 pages.
International Search Report and Written Opinion dated Mar. 12, 2020 in International Patent Application No. PCT/CN2019/123223, 12 pages.
U.S. Appl. No. 17/172,988, filed Feb. 10, 2021, Dai, X., et al.
Lanman, B.A., et al. Discovery of a covalent inhibitor of KrasG12C (AMG510) for the treatment of solid tumors, J Med Chem., 63:52-65 (2019).
International Search Report and Written Opinion dated Aug. 19, 2020 in International Patent Application No. PCT/CN2020/091274, 14 pages.
International Search Report and Written Opinion dated Mar. 17, 2021 in International Patent Application No. PCT/CN2020/137276, 16 pages.
International Search Report and Written Opinion dated Sep. 22, 2020 in International Patent Application No. PCT/CN2019/126230, 14 pages.

*Primary Examiner* — Raymond J Henley, III
(74) *Attorney, Agent, or Firm* — Nixon & Vanderhye P.C.

(57) ABSTRACT

Provided herein are compounds, crystalline forms, and pharmaceutical compositions of Compound 1 and/or Compound 2. Also provided are methods of treating a disease or disorder such as a cancer or infectious disease that comprises administering to a subject in need thereof one or more of the compounds or compositions of the present disclosure.

23 Claims, 13 Drawing Sheets

HETEROCYCLIC COMPOUNDS, PREPARATION METHODS AND USES THEREOF

CROSS-REFERENCE TO RELATED PATENT APPLICATIONS

This Patent Application is a continuation of PCT Application No. PCT/CN2020/137276, filed Dec. 17, 2020, which claims priority to International Application No. PCT/CN2019/126230, filed Dec. 18, 2019, the entire contents of each of which are hereby incorporated herein by reference.

BACKGROUND

In various embodiments, the present disclosure generally relates to novel heterocyclic compounds, compositions of the same, methods of preparing and methods of using the same, e.g., for inhibiting RAS and/or for treating a number of diseases or disorders, such as pancreatic, colorectal, and lung cancers.

BACKGROUND

RAS proteins regulate key cellular pathway transmitting signal received from cellular membrane receptor to downstream molecules such as Raf, MEK, ERK and PI3K, which are crucial for cell proliferation and survival. RAS cycles between the inactive GDP-bound form and active GTP-bound form. RAS proteins have three gene isoforms: KRAS, NRAS and HRAS and share extensive homology (>90%) in the N-terminal domain (amino acid 1-165). RAS is frequently mutated cancers with KRAS accounted for ~80% of all RAS mutations. KRAS mutation occurs in approximately 60% of pancreatic cancer, 40% of colorectal cancer, 30% of lung cancer and 20% of endometrial carcinoma (F. McCormick, 2017, Clin Cancer Res 21: 1797-1801). The RAS hot-spot mutations occur at codons 12, 13 and 61, with 75% of KRAS mutations occurs at codon 12 (Glycine) (D. K. Simanshu, D. V. Nissley and F. McCormick, 2017, Cell, 170: 17-33).

There is a medical need for therapeutic treatments of cancer patients with RAS mutation such as KRAS G12C mutation.

BRIEF SUMMARY

International Application Nos. PCT/CN2019/087772, filed on May 21, 2019, and PCT/CN2019/095947, filed on Jul. 15, 2019, the content of each of which is incorporated herein by reference in its entirety, describe Compounds 1 and 2 as RAS inhibitors, such as KRAS G12C inhibitors and are useful for treating various diseases or disorders, such as cancer associated with KRAS G12C mutation.

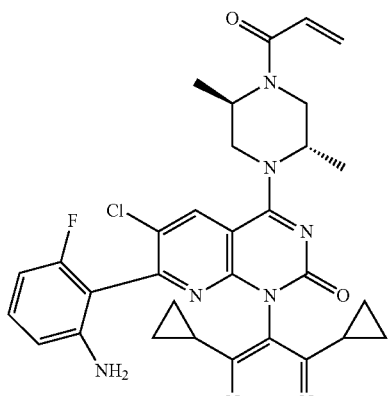

Compound 1

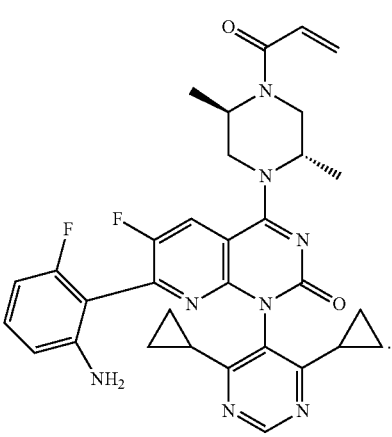

Compound 2

In various embodiments, the present disclosure is directed to Compound 1, or Compound 2, which can be for example, in an isolated form, a substantially pure form, and/or in a solid form. Further provided are pharmaceutical compositions comprising the Compound 1 or Compound 2, methods of preparing the same, and methods of using the same.

Certain embodiments of the present disclosure are directed to Compound 1, which can be for example, in a substantially pure form and/or in a solid form. In some embodiments, the Compound 1 can be in an amorphous form. In some embodiments, the Compound 1 can be in a crystalline form, such as Form I, Form II, Form III, or Form IV as described herein. In some embodiments, Compound 1 can be substantially pure.

Certain embodiments of the present disclosure are directed to Compound 2, which can be for example, in a substantially pure form and/or in a solid form. In some embodiments, the Compound 2 can be in an amorphous form. In some embodiments, the Compound 2 can be in a crystalline form, such as Form A, Form B, Form C, or Form D as described herein. In some embodiments, Compound 2 can be substantially pure.

Compounds of the present disclosure can be used for preparing a pharmaceutical composition. In some embodiments, the pharmaceutical composition can comprise one or more of the compounds of the present disclosure (e.g., Compound 1 in Form IV, amorphous Compound 1, Compound 2 in Form B, amorphous Compound 2, or any combination thereof).

The pharmaceutical compositions described herein can be formulated for any suitable routes of administration. In some embodiments, the pharmaceutical composition can be formulated for oral administration. For example, in some embodiments, the pharmaceutical composition can be a tablet or a capsule.

Certain embodiments of the present disclosure are directed to methods of using the compounds or compositions of the present disclosure. For example, in some embodiments, the present disclosure provides a method for inhibiting KRAS G12C mutant protein in a cell, which can comprise contacting the cell with Compound 1 or 2. In some embodiments, the present disclosure provides a method of treating cancer in a subject, the method comprising administering to the subject a therapeutically effective amount of a compound of the present disclosure (e.g., Compound 1 in Form IV, amorphous Compound 1, Compound 2 in Form B, amorphous Compound 2, or any combination thereof), or pharmaceutical composition described herein. In some embodiments, the cancer is a hematologic malignancy, lung cancer (e.g., non-small cell lung cancer), pancreatic cancer, endometrial cancer, gall bladder cancer, thyroid cancer, bile duct cancer, and/or colorectal cancer.

Compounds of the present disclosure can be used as a monotherapy or in a combination therapy. For example, in some embodiments, the method herein is for treating cancer in a subject in need thereof, the method comprising administering to the subject an effective amount (e.g., therapeutically effective amount) of a compound of the present disclosure. In some embodiments, the method can further comprise treating the subject with an additional anti-cancer therapy. In some embodiments, the additional anti-cancer therapy is a chemotherapeutic agent, therapeutic antibody, radiation, cell therapy, or immunotherapy.

It is to be understood that both the foregoing summary and the following detailed description are exemplary and explanatory only, and are not restrictive of the invention herein.

BRIEF DESCRIPTION OF THE DRAWINGS/FIGURES

Figure 4A:
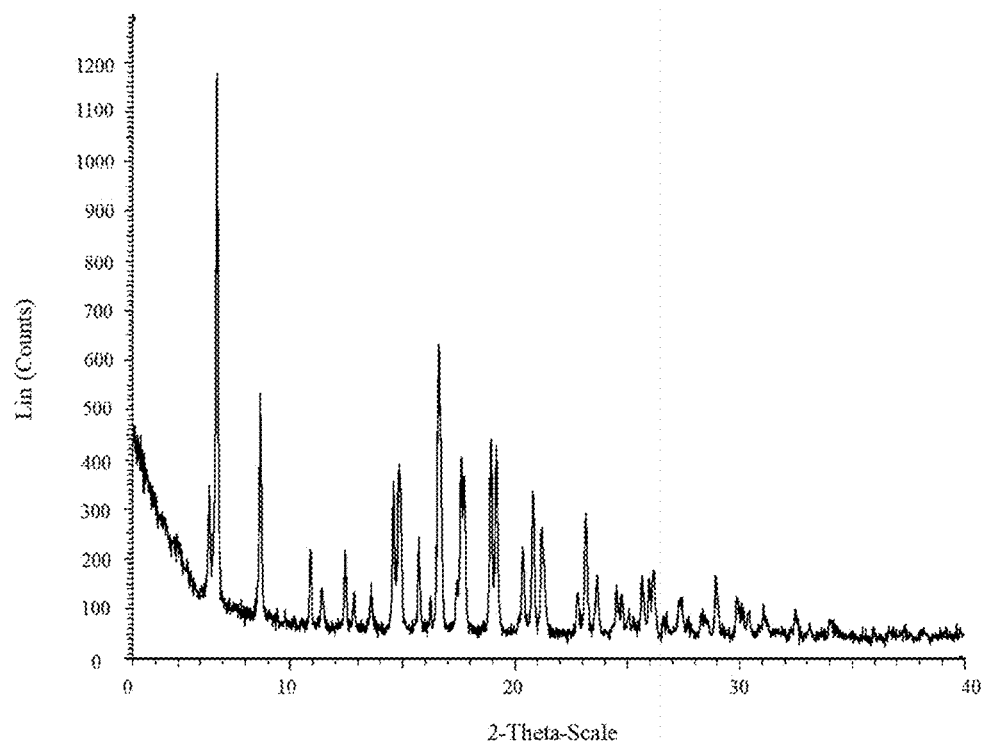
Figure 4B:
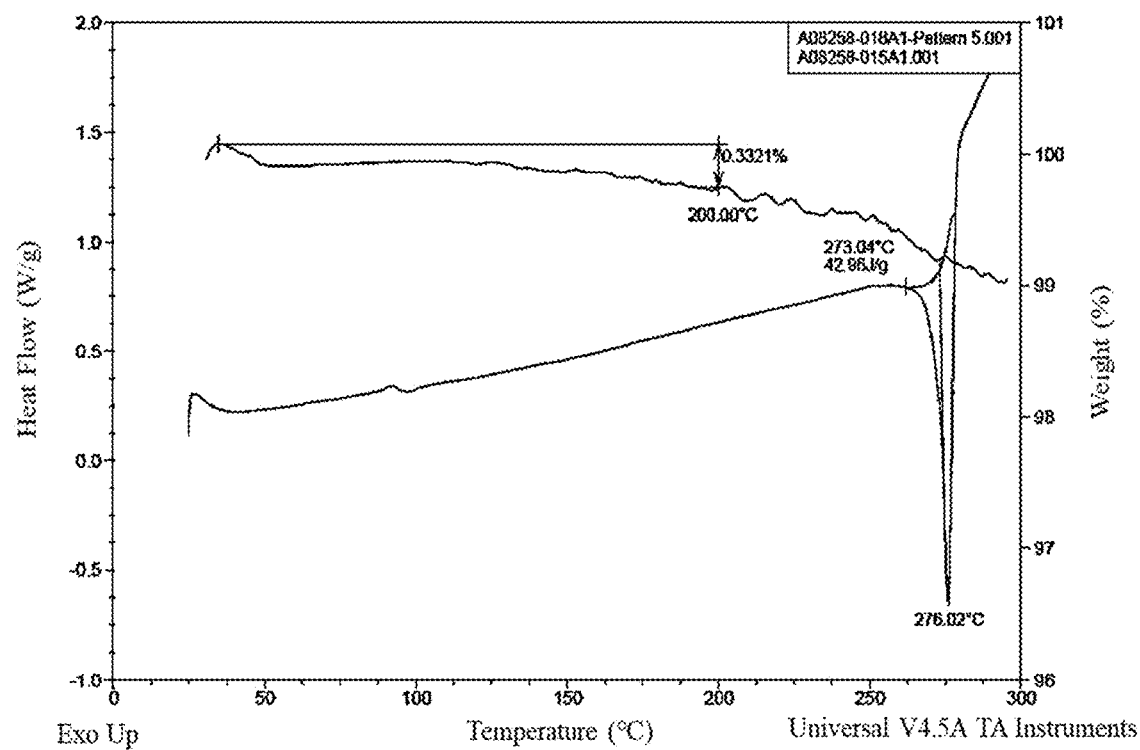
Figure 4C:
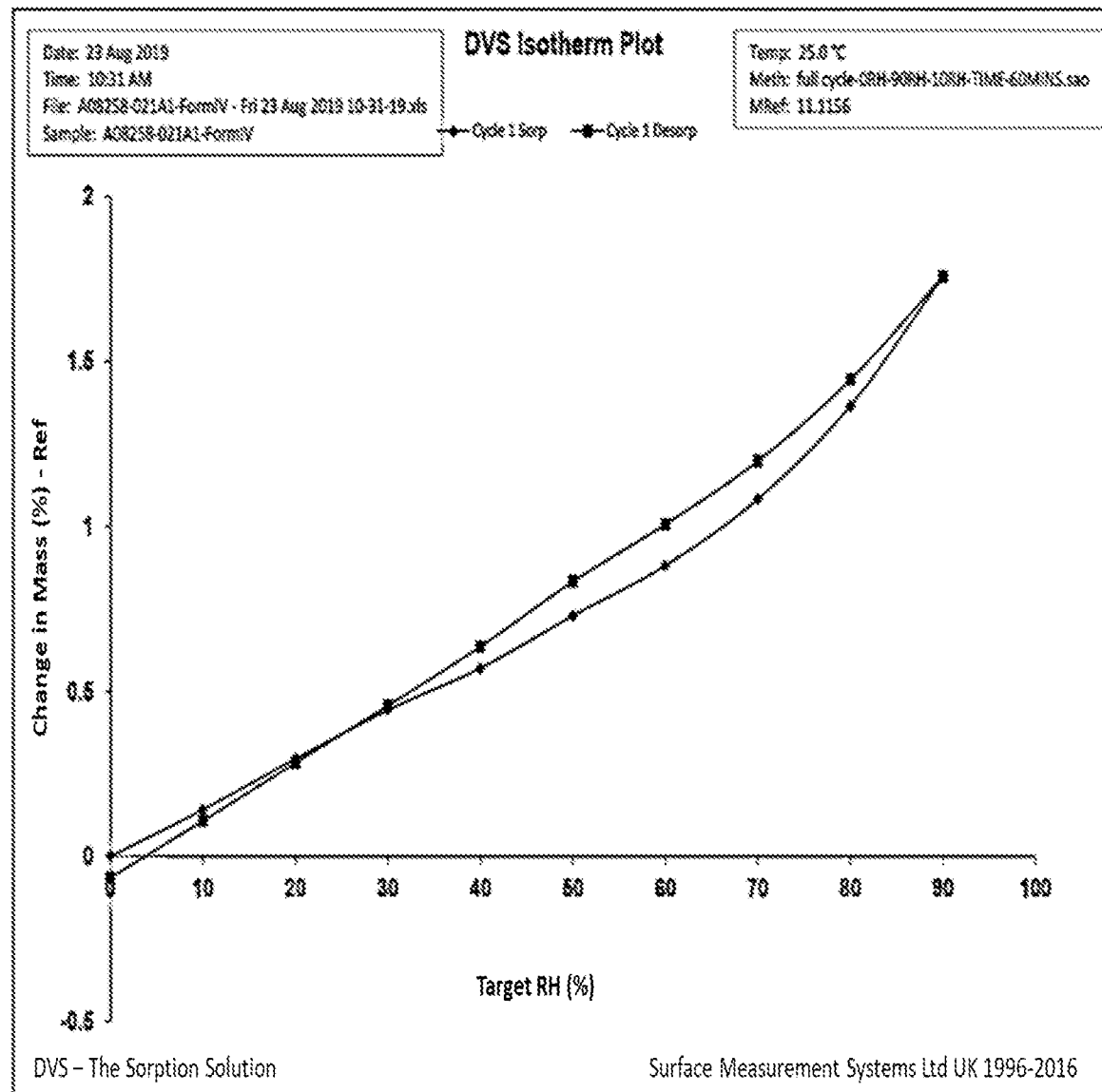

FIG. 4A shows a representative X-ray powder diffraction (XRPD) spectrum of crystalline form IV of Compound 1. FIG. 4B shows a representative thermogravimetric analysis (TGA) and differential scanning calorimetry (DSC) analysis of crystalline form IV of Compound 1. FIG. 4C presents a representative Dynamic moisture sorption analysis (DVS) of Form IV of Compound 1.

Figure 5A:
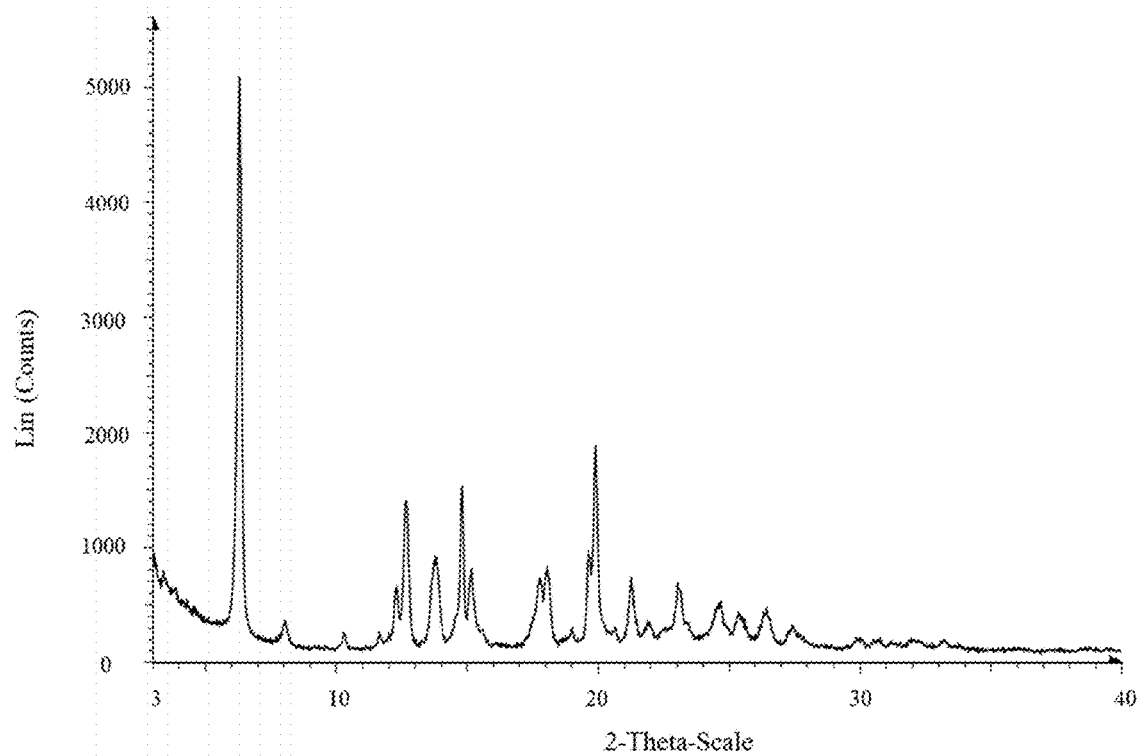
Figure 5B:
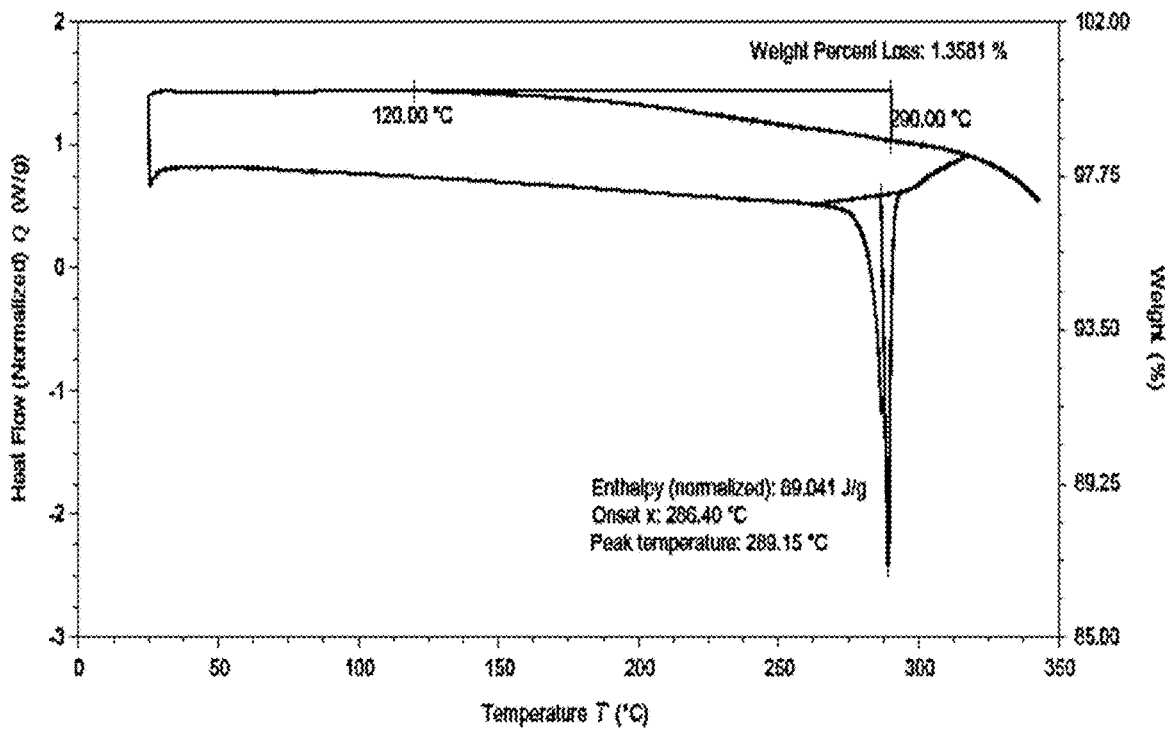

FIG. 5A shows a representative X-ray powder diffraction (XRPD) spectrum of crystalline form A of Compound 2. FIG. 5B shows a representative thermogravimetric analysis (TGA) and differential scanning calorimetry (DSC) analysis of crystalline form A of Compound 2.

Figure 6A:
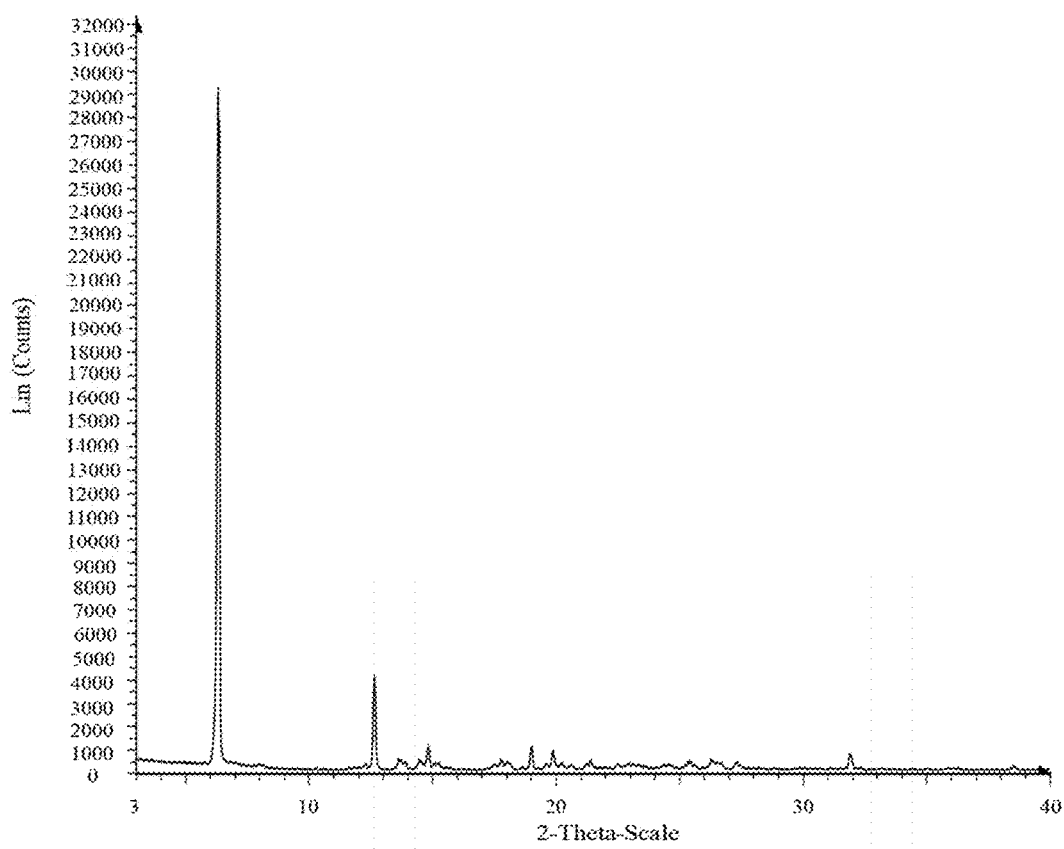
Figure 6B:
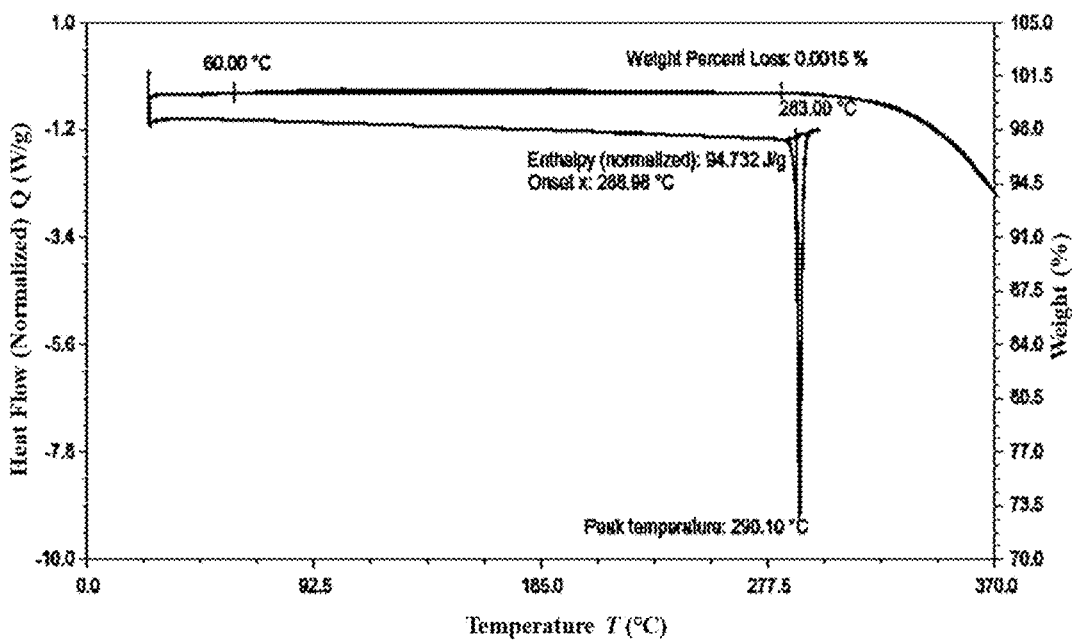
Figure 6C:
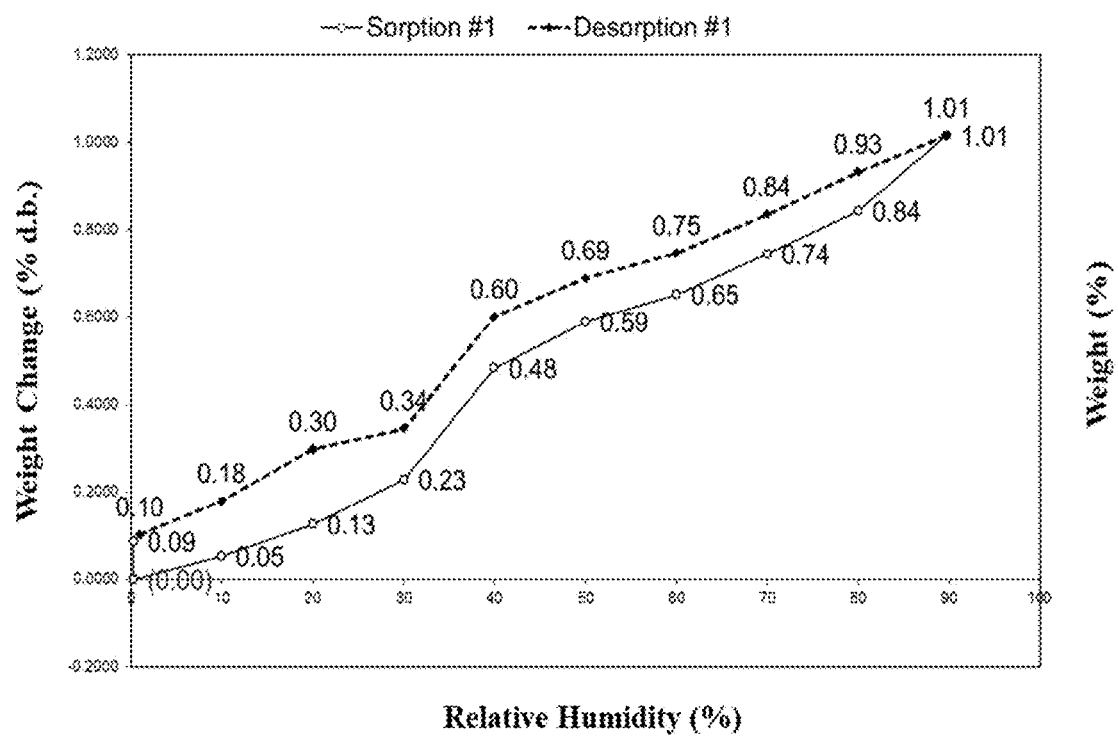
Figure 6D:
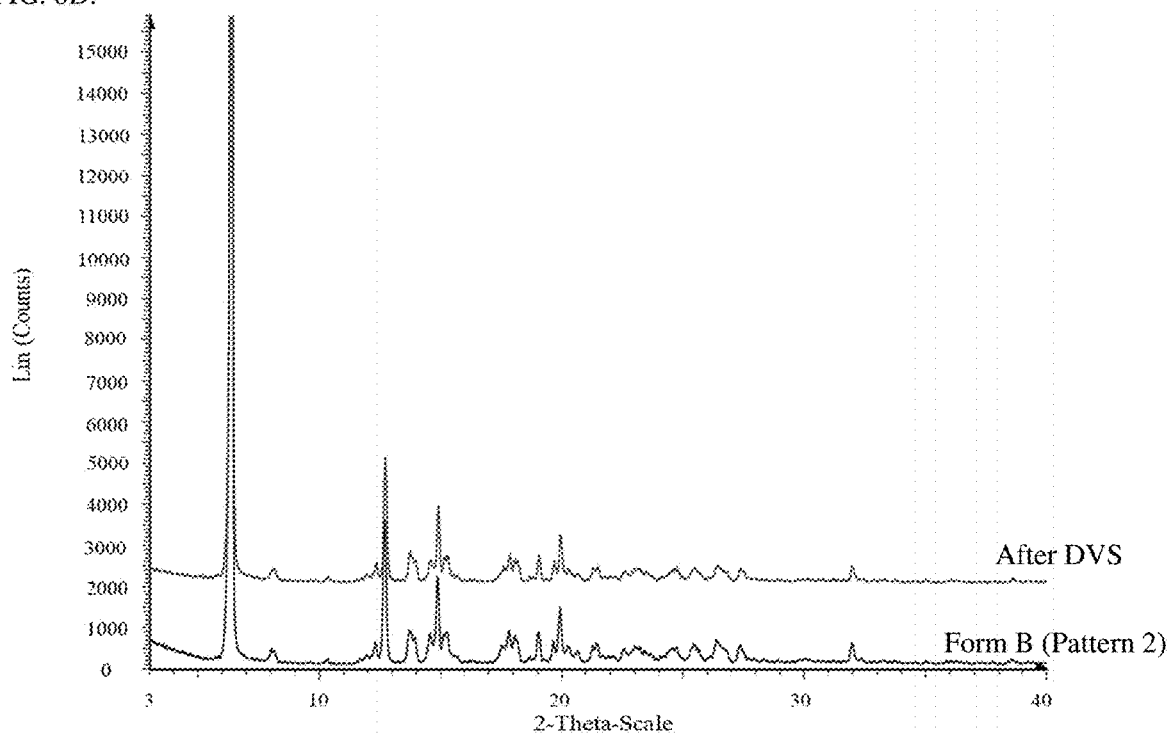

FIG. 6A shows a representative X-ray powder diffraction (XRPD) spectrum of crystalline form B of Compound 2. FIG. 6B shows a representative thermogravimetric analysis (TGA) and differential scanning calorimetry (DSC) analysis of crystalline form B of Compound 2. FIG. 6C presents a representative Dynamic moisture sorption analysis (DVS) of form B of Compound 2. FIG. 6D presents XRPD spectra showing that Form B remain unchanged after DVS study.

Figure 7A:
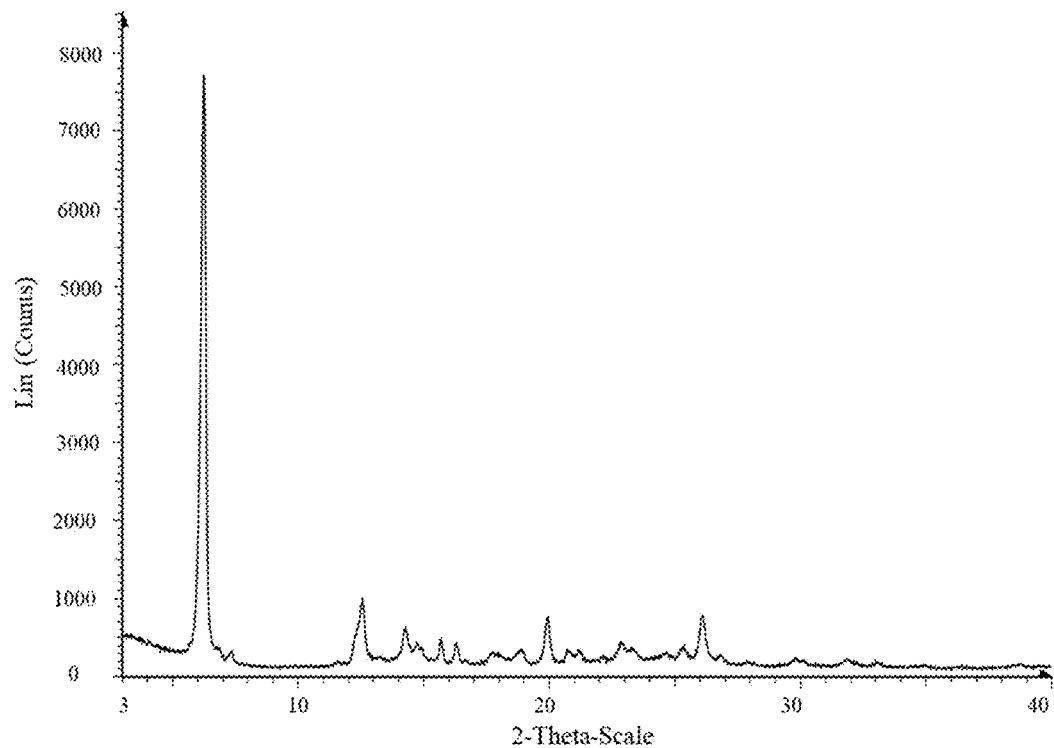
Figure 7B:
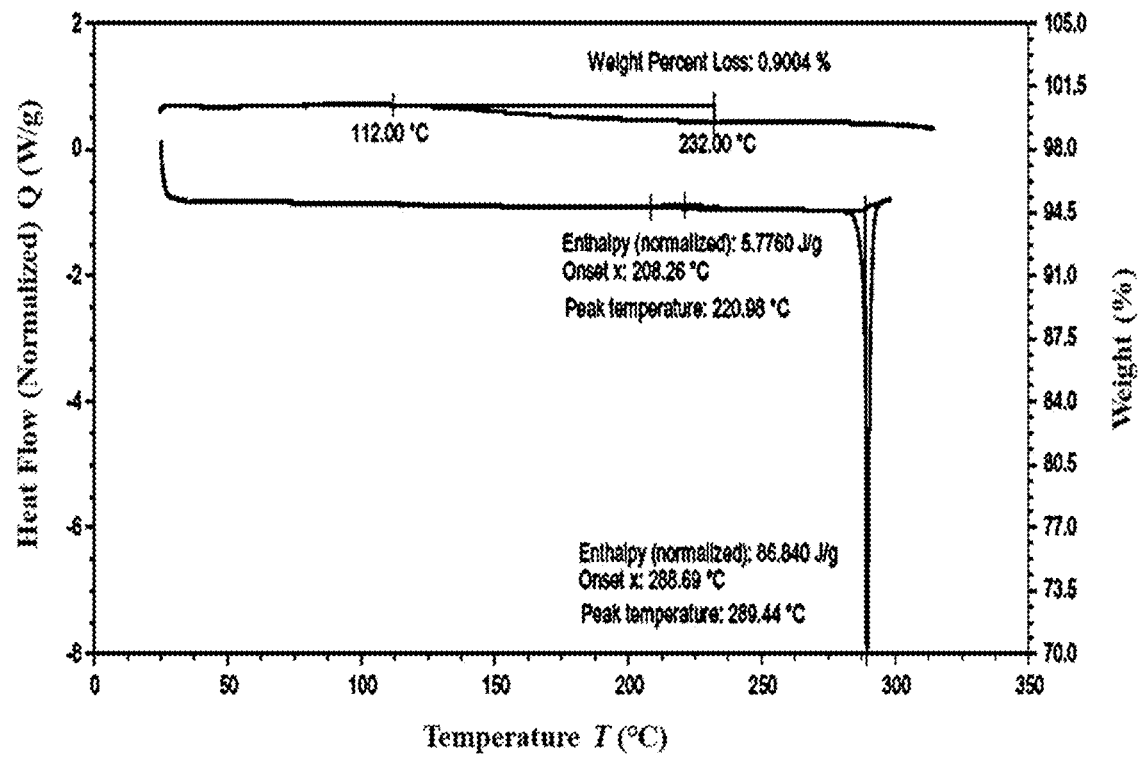

FIG. 7A shows a representative X-ray powder diffraction (XRPD) spectrum of crystalline form C of Compound 2. FIG. 7B shows a representative thermogravimetric analysis (TGA) and differential scanning calorimetry (DSC) analysis of crystalline form C of Compound 2.

Figure 8A:
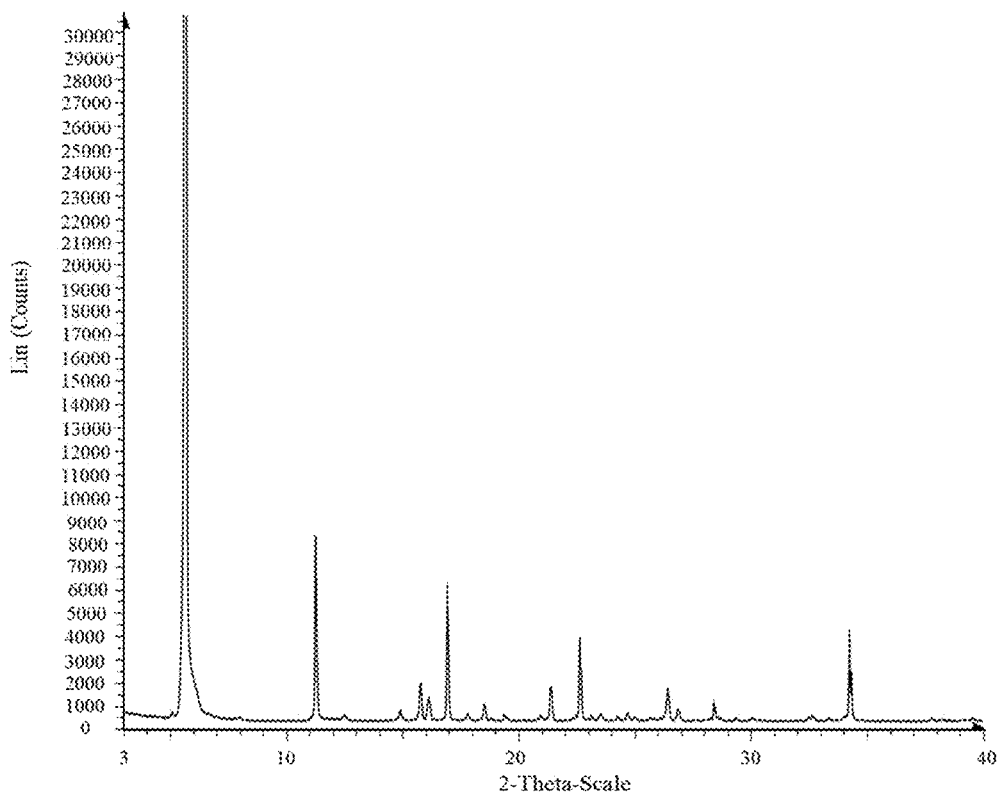
Figure 8B:
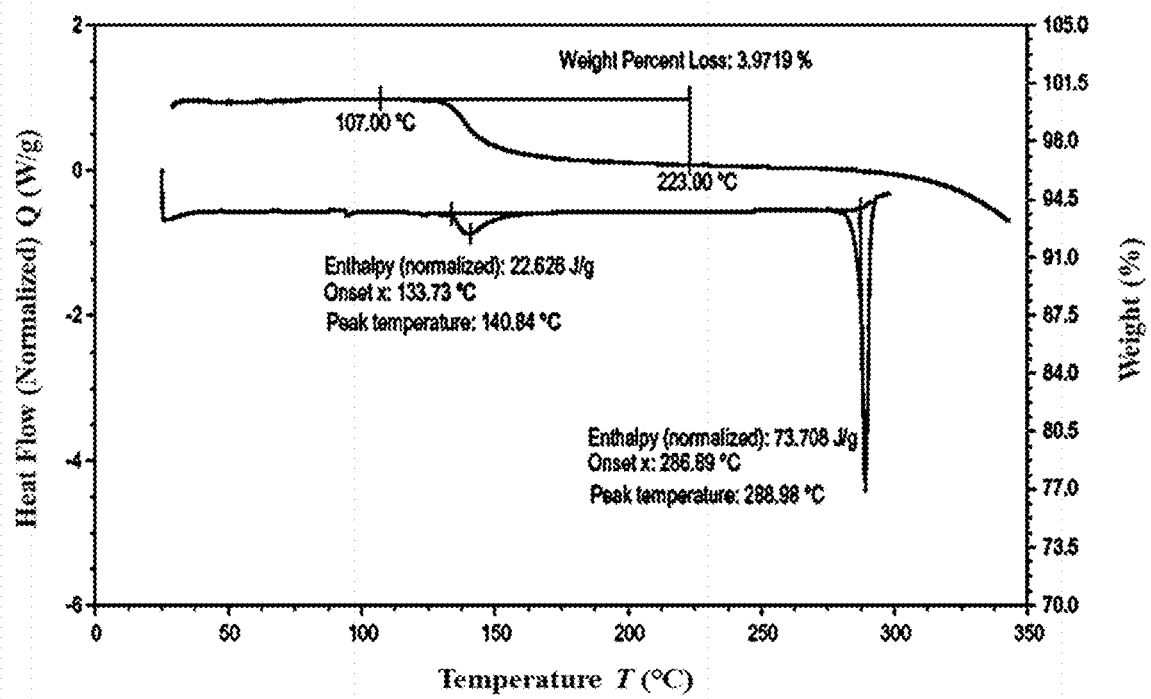

FIG. 8A shows a representative X-ray powder diffraction (XRPD) spectrum of crystalline form D of Compound 2. FIG. 8B shows a representative thermogravimetric analysis (TGA) and differential scanning calorimetry (DSC) analysis of crystalline form D of Compound 2.

Figure 9A:
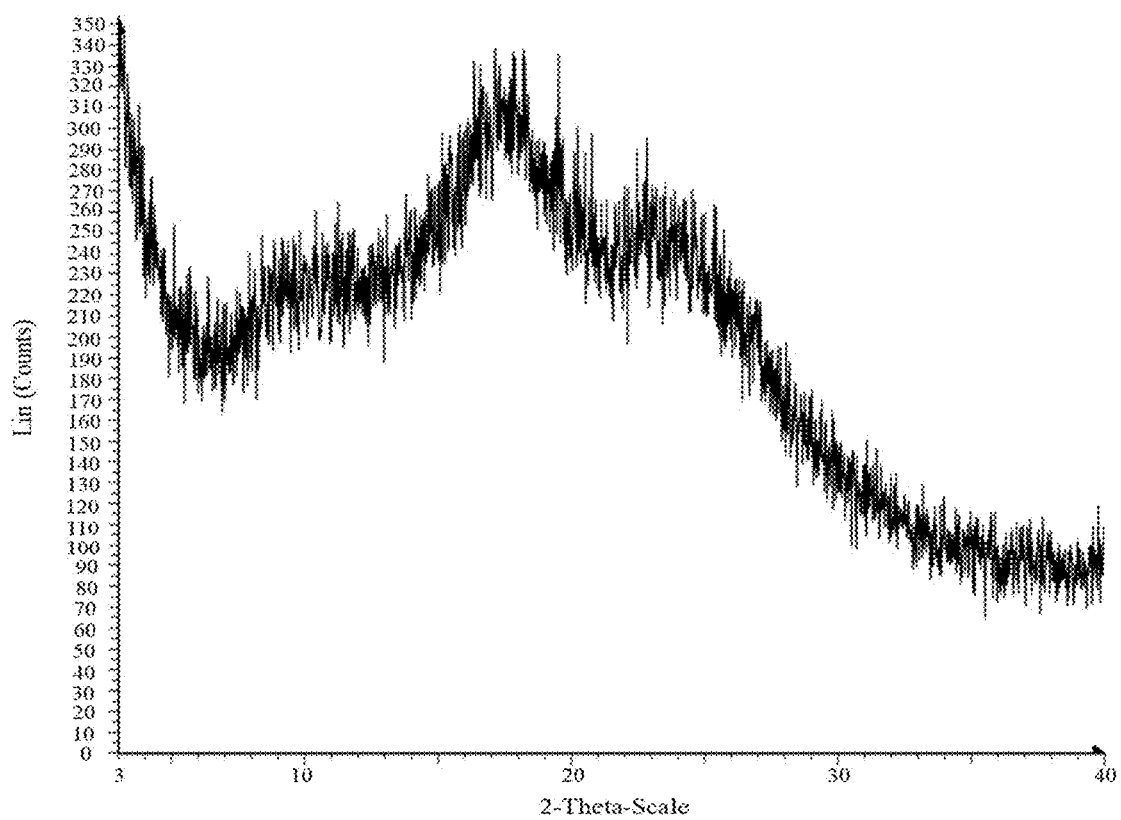
Figure 9B:
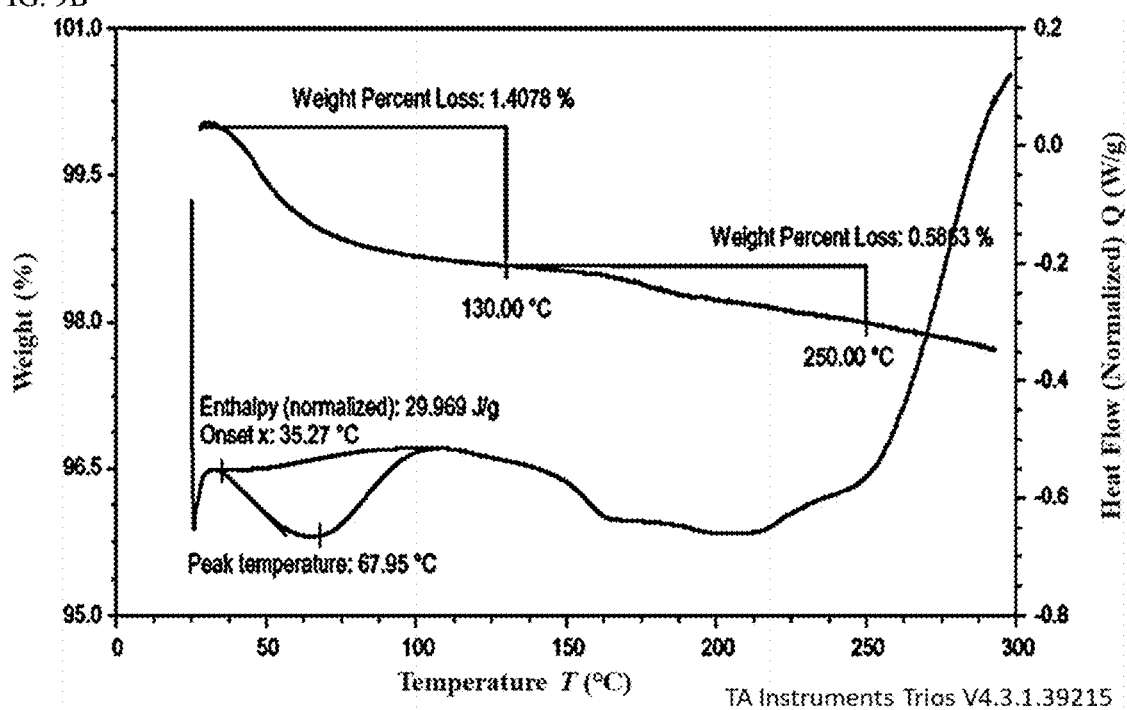
Figure 9C:
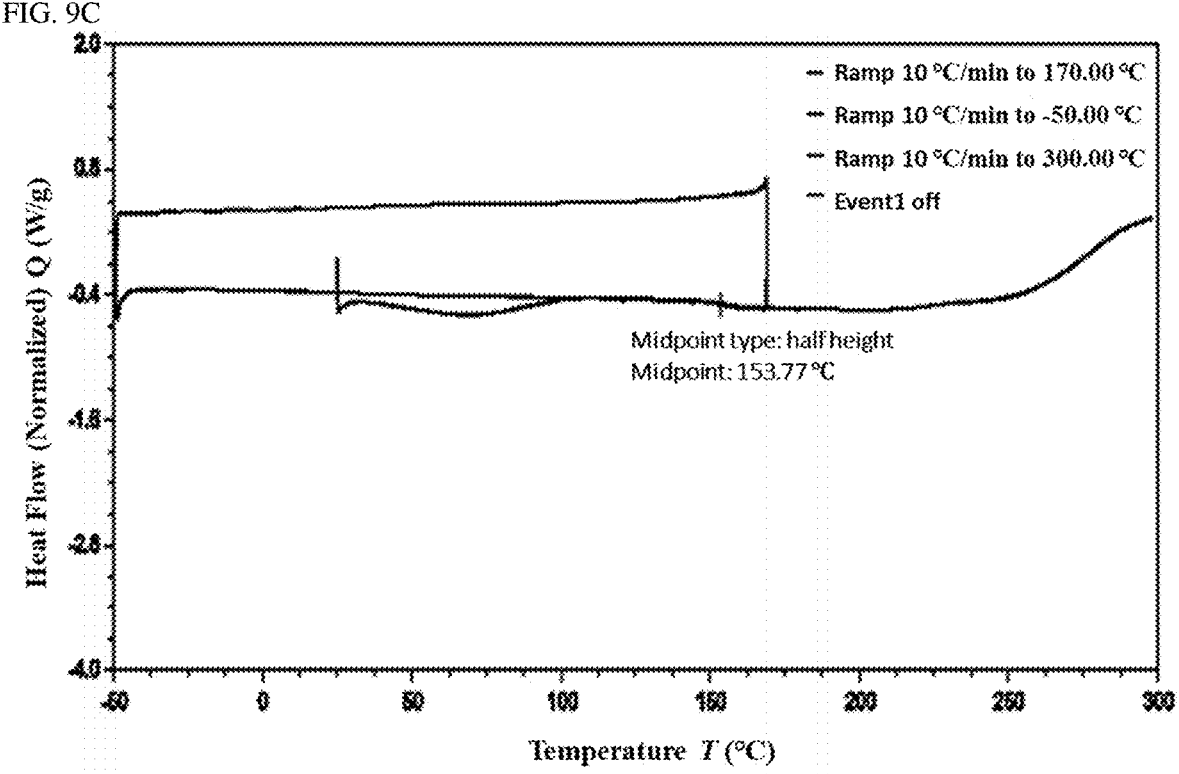

FIG. 9A shows a representative X-ray powder diffraction (XRPD) spectrum of an amorphous Compound 1. FIG. 9B shows a representative thermogravimetric analysis (TGA) and differential scanning calorimetry (DSC) analysis of an amorphous Compound 1. FIG. 9C shows a differential scanning calorimetry (DSC) study of an amorphous Compound 1.

Figure 10:
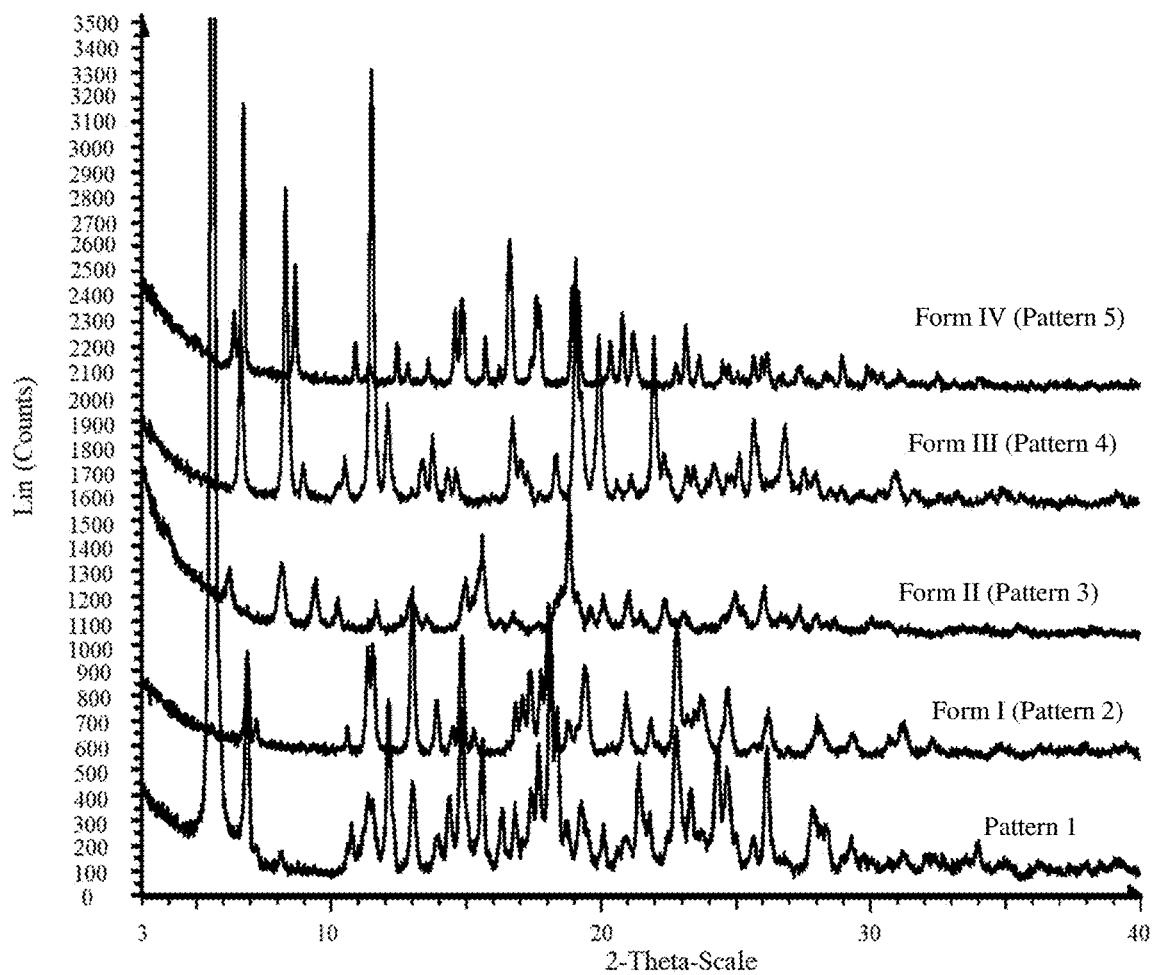

FIG. 10 shows a comparison of different XRPD patterns observed for Compound 1.

DETAILED DESCRIPTION

In various embodiments, the present disclosure is directed to RAS inhibitors, such as KRAS inhibitors, more specifically, Compounds 1 and 2, which for example, can be in an isolated form, a substantially pure form, and/or in a solid form. Compounds 1 and 2 have a pKa of around 3 and typically exist in a free base form. Unless otherwise explicitly stated to the contrary, Compound 1 or 2 herein should be understood as existing in its free base form as opposed to a salt formed with an acid or base. As exemplified in the Examples section, various polymorphic forms of Compounds 1 and 2 were found. Among these polymorphs, Form IV of Compound 1 and Form B of Compound 2 were found to be stable and can be more suited for various pharmaceutical uses compared to other forms for the respective compound. Compound 1 and 2 have the following formulae, respectively:

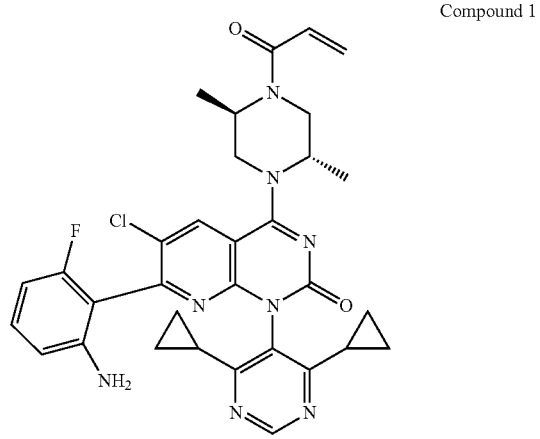

Compound 1

-continued

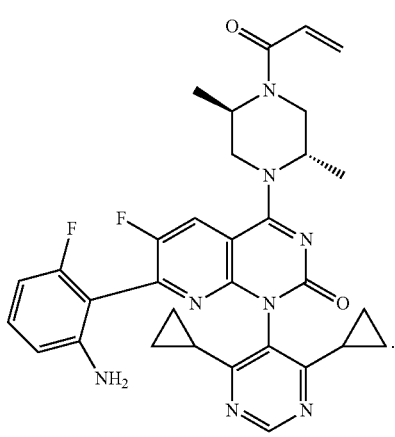

Compound 2

As described in International Application Nos. PCT/CN2019/087772, filed on May 21, 2019, and PCT/CN2019/095947, filed on Jul. 15, 2019, the content of each of which is incorporated herein by reference in its entirety, Compounds 1 and 2 are RAS inhibitors, such as KRAS G12C inhibitors and are useful for treating various diseases or disorders, such as cancer associated with KRAS G12C mutation. Thus, some embodiments of the present disclosure are also directed to pharmaceutical compositions comprising Compound 1 and/or Compound 2 as described herein. In some embodiments, a method of treating or preventing a disease or disorder associated with RAS such as KRAS G12C mutation is also provided, which comprises administering to a subject in need thereof a therapeutically effective amount of the Compound 1 as described herein, or a pharmaceutical composition described herein. In some embodiments, a method of treating or preventing a disease or disorder associated with RAS such as KRAS G12C mutation is also provided, which comprises administering to a subject in need thereof a therapeutically effective amount of the Compound 2 as described herein, or a pharmaceutical composition described herein.

Compound 1

In some embodiments, the present disclosure is directed to Compound 1. Compound 1 and its synthesis were described in International Application Nos. PCT/CN2019/087772, filed on May 21, 2019, and/or PCT/CN2019/095947, filed on Jul. 15, 2019, the content of each of which is herein incorporated by reference in its entirety. Compound 1 should be understood as in its free base form to distinguish it from a salt formed with an external acid or base. Unless obvious from context, Compound 1 should be understood as in its free base form as discussed.

In some embodiments, Compound 1 can be in a solid form, such as an amorphous form, a crystalline form, or a combination thereof. In some embodiments, Compound 1 can be an amorphous form. In some embodiments, Compound 1 can be in a crystalline form (e.g., in any one or more crystalline forms I, II, III and IV as described herein). As used herein, when a compound (e.g., Compound 1) is said to exist or be in one particular solid form (e.g., a crystalline form), it should be understood that in some embodiments, the compound can exist predominantly in that particular form. However, in some embodiments, the compound can also exist in the particular form, in a mixture with one or more other solid forms, including amorphous form. For example, when Compound 1 is said to exist or be in Form IV, Compound 1 can exist predominantly in Form IV, such as more than 80% by weight, more than 90% by weight, or more than 95% by weight of Compound 1 are in Form IV, or no other solid form can be identified, for example, by XRPD; or in some embodiments, Compound 1 can exist in Form IV, in a mixture with one or more solid forms such as an amorphous form.

Compound 1 herein is typically in a substantially pure form. For example, in some embodiments, Compound 1 can have a purity of greater than 70%, preferably greater than 90% (e.g., greater than 95%, greater than 97%, greater than 98%, greater than 98.5%), by weight, by HPLC area, or both. In some embodiments, the Compound 1 can be characterized by a purity by weight and/or by HPLC area of about 70%, about 75%, about 80%, about 85%, about 90%, about 95%, about 97%, about 99%, or any ranges between the specified values. For example, in some embodiments, the Compound 1 can be characterized by a purity by HPLC area of about 70%, about 75%, about 80%, about 85%, about 90%, about 95%, about 97%, about 99%, or any ranges between the specified values. The substantially pure Compound 1 can be in a solid form (e.g., a crystalline form described herein, amorphous form, or a combination thereof) or in a solution, suspension, or another form. In some embodiments, the substantially pure Compound 1 can be in crystalline Form IV. For the avoidance of doubt, a composition comprising the substantially pure Compound 1 herein and one or more other ingredients should be understood as a mixture of the substantially pure Compound 1 herein and the one or more other ingredients, for example, such composition can be obtained directly or indirectly from mixing the substantially pure Compound 1 with the one or more other ingredients, such as solvent, pharmaceutically acceptable excipients, etc.

Figure 1A:
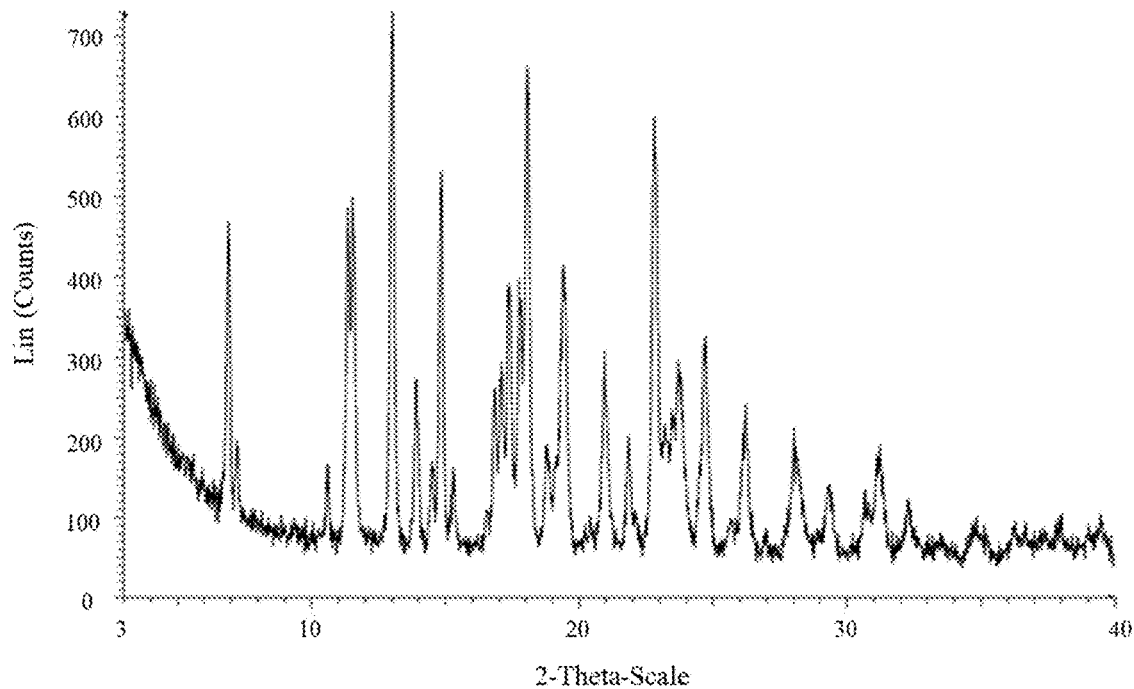
FIG. 1A shows a representative X-ray powder diffraction (XRPD) spectrum of crystalline form I of Compound 1.
Figure 1B:
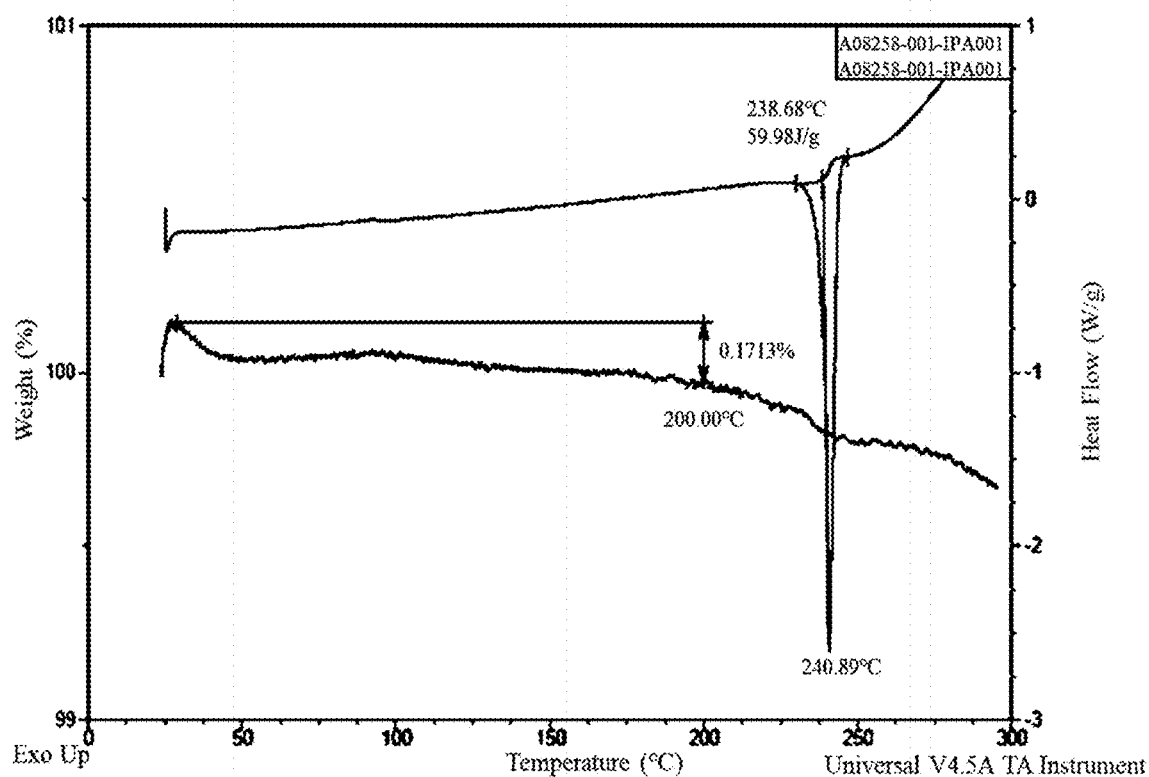
FIG. 1B shows a representative thermogravimetric analysis (TGA) and differential scanning calorimetry (DSC) analysis of crystalline form I of Compound 1.

In some embodiments, the Compound 1 is in a crystalline form. In some embodiments, the Compound 1 is in a crystalline Form I. Characteristics of Form I include any of those described herein. In some embodiments, crystalline Form I can be characterized by (1) an X-ray powder diffraction (XRPD) pattern having one or more (e.g., 2, 4, 6, 8, or 10) of the following peaks: 6.9, 11.4, 11.5, 13.0, 14.8, 17.4, 17.8, 18.1, 19.4, and 22.8 degrees 2 theta, ±0.2°; (2) an X-ray powder diffraction (XRPD) pattern having one or more (e.g., 6 or more, 8 or more, 12 or more, or all) of the following peaks: 6.9, 11.4, 11.5, 13.0, 13.9, 14.8, 16.8, 17.1, 17.4, 17.8, 18.1, 19.4, 21.0, 22.8, 23.7, 24.7, and 26.2 degrees 2 theta, ±0.2°; (3) an XRPD pattern substantially the same as shown in FIG. 1A; (4) a Differential Scanning Calorimetry (DSC) pattern substantially the same as shown in FIG. 1B; or any combination thereof (e.g., (1) and (4), (2) and (4), (1), (2) and (4), or (3) and (4)). In some embodiments, the crystalline Form I can be characterized by an XRPD pattern having the major peaks (e.g., peaks with relative intensity of 20% or above, 30% or above, 40% or above, 50% or above, 60% or above, 70% or above, 80% or above, or 90% or above) of FIG. 1A or as shown in Table 1, degrees 2 theta, ±0.2°. To be clear, when it is said that the XRPD pattern of Form I has the major peaks of FIG. 1A or Table 1 or is substantially the same as FIG. 1A, it does not require that the XRPD pattern have the same relative intensities for the corresponding peaks as shown in FIG. 1A or Table 1, as applicable. It suffices that the XRPD pattern includes the peaks at the respective diffraction angels (degrees 2 theta, ±0.2°) corresponding to the peaks as shown in FIG. 1A or Table 1, as applicable, regardless of their relative intensities. Similar expressions as to other crystalline forms herein should be understood similarly. In some embodiments, the crystalline Form I can be characterized by an XRPD pattern having all of the following peaks: 6.9, 11.4, 11.5, 13.0, 14.8, 17.4, 17.8, 18.1, 19.4, and 22.8 degrees 2 theta, ±0.2°. In some embodiments, the crystalline Form I can also be characterized by a DSC pattern having an endothermic peak with an onset temperature of about 238.7° C. and/or peak temperature at about 240.9° C. As shown in the Examples section, Form I was determined to be an anhydrate. In some embodiments, the crystalline Form I is substantially the same as the crystalline Form I obtained in Example 3 of this application.

The Compound 1 in crystalline Form I can be prepared by methods described herein. For example, in some embodiments, Compound 1 in crystalline Form I can be prepared by a method comprising 1) suspending amorphous Compound 1 in a solvent, such as water, isopropanol, MTBE, THF/heptane and EA/heptane, preferably, isopropanol, to form a suspension; and 2) stirring the suspension at room temperature (RT) or under heat, such as at 50° C., for a period of time, such as 1 day, 3 days, etc. to form Compound 1 in crystalline Form I. In some embodiments, Compound 1 in crystalline Form I can be prepared by a method comprising 1) dissolving Compound 1 in a first solvent, such as ethyl acetate (EA) or tetrahydrofuran (THF), to form a solution; and then 2) adding an anti-solvent, such as MTBE (methyl tert-butyl ether), to the solution to precipitate Compound 1. Exemplified procedures for preparing Compound 1 in Form I are shown in Example 3 of this application.

Figure 2A:
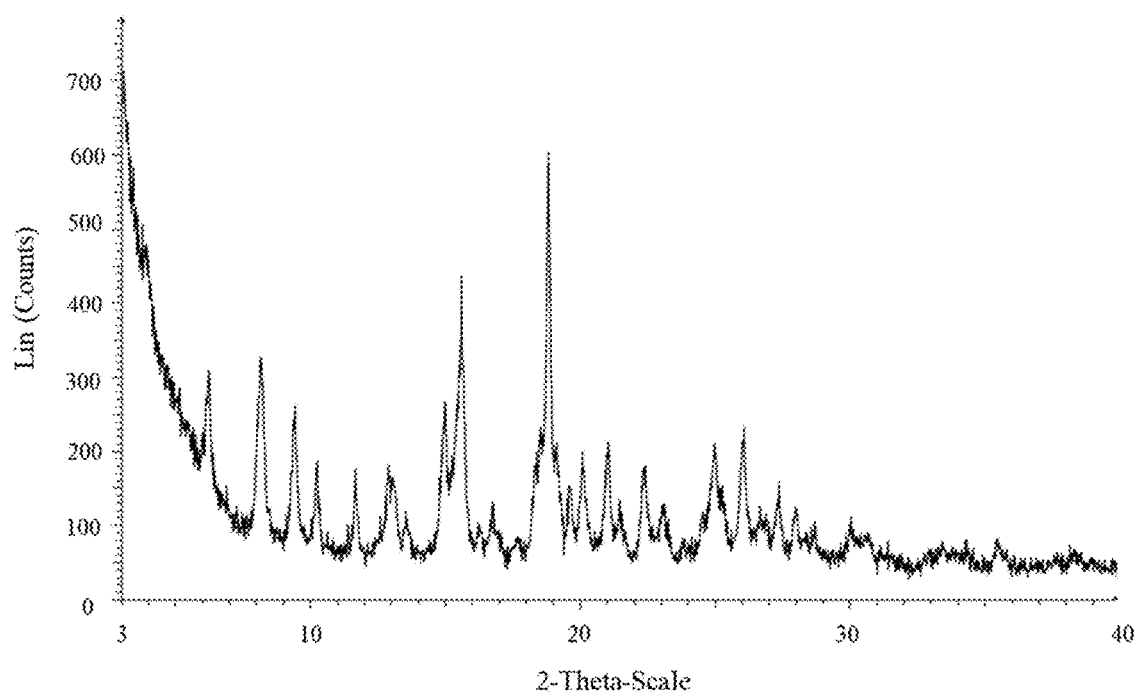
FIG. 2A shows a representative X-ray powder diffraction (XRPD) spectrum of crystalline form II of Compound 1.
Figure 2B:
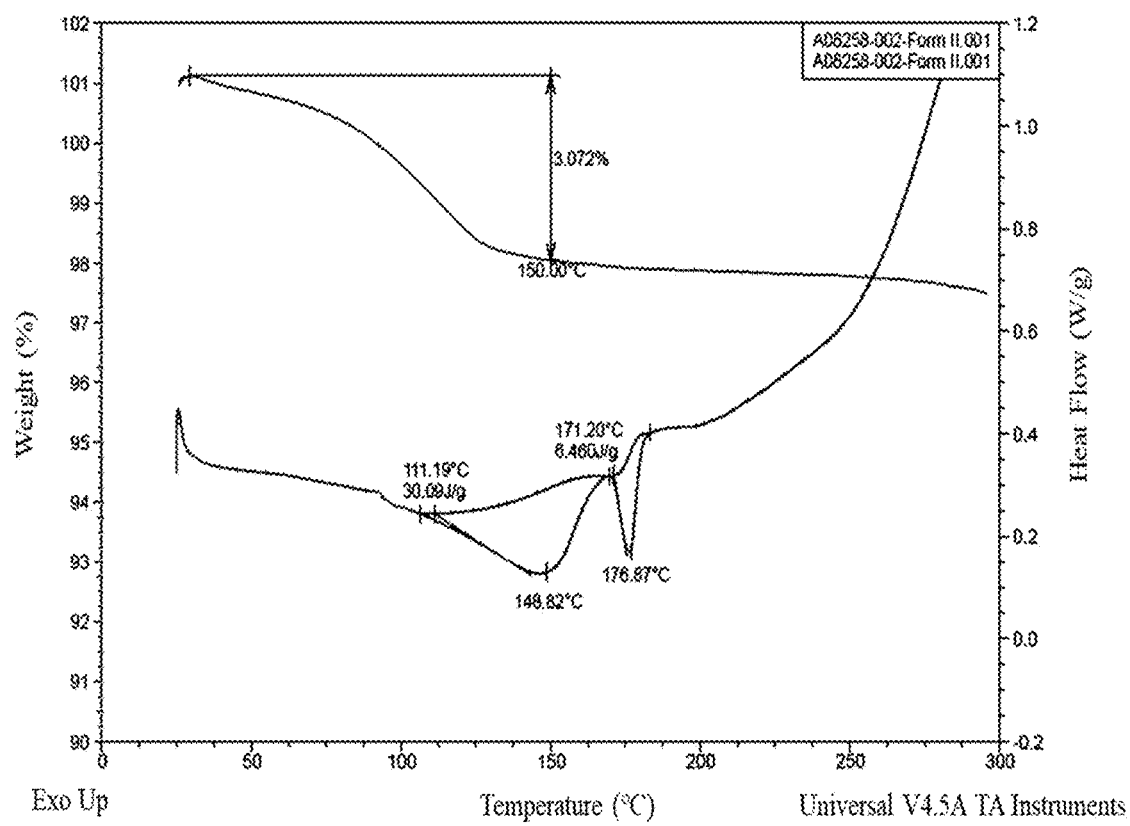
FIG. 2B shows a representative thermogravimetric analysis (TGA) and differential scanning calorimetry (DSC) analysis of crystalline form II of Compound 1.

In some embodiments, the Compound 1 is in a crystalline Form II. Characteristics of Form II include any of those described herein. In some embodiments, crystalline Form II can be characterized by (1) an X-ray powder diffraction (XRPD) pattern having one or more (e.g., 1, 2, or 3) of the following peaks: 8.1, 15.6, and 18.8 degrees 2 theta, ±0.2°; (2) an X-ray powder diffraction (XRPD) pattern having one or more (e.g., 6 or more, 8 or more, or all) of the following peaks: 6.2, 8.1, 9.4, 10.2, 15.6, 18.8, 19.1, 20.1, 21.0, 25.0, and 26.0 degrees 2 theta, ±0.2°; (3) an XRPD pattern substantially the same as shown in FIG. 2A; (4) a Differential Scanning Calorimetry (DSC) pattern substantially the same as shown in FIG. 2B; or any combination thereof (e.g., (1) and (4), (2) and (4), (1), (2) and (4), or (3) and (4)). In some embodiments, the crystalline Form II can be characterized by an XRPD pattern having the major peaks (e.g., peaks with relative intensity of 20% or above, 30% or above, 40% or above, 50% or above, 60% or above, 70% or above, 80% or above, or 90% or above) of FIG. 2A or as shown in Table 2, degrees 2 theta, ±0.2°. In some embodiments, the crystalline Form II can be characterized by an XRPD pattern having all of the following peaks: 8.1, 15.6, and 18.8 degrees 2 theta, ±0.2°. In some embodiments, the crystalline Form II can also be characterized by a DSC pattern having an endothermic peak with an onset temperature of about 171.2° C. and/or peak temperature at about 176.8° C.; and an endothermic peak with an onset temperature of about 111.2° C. and/or peak temperature at about 148.8° C. As shown in the Examples section, Form II was determined to be a mono-hydrate. In some embodiments, the crystalline Form H is substantially the same as the crystalline Form II obtained in Example 3 of this application.

The Compound 1 in crystalline Form II can be prepared by methods described herein. For example, in some embodiments, Compound 1 in crystalline Form II can be prepared by a method comprising 1) dissolving Compound 1 in a first solvent, such as acetone, e.g., at room temperature, to form a solution; and then 2) adding an anti-solvent, such as water, to the solution to precipitate Compound 1. In some embodiments, the method further comprises stirring the mixture of Compound 1 in the first solvent and the anti-solvent, e.g., at room temperature, for a period of time (e.g., 1-5 days), to form a suspension; and optionally filtering and drying the precipitated Compound 1. Exemplified procedures for preparing Compound 1 in Form II are shown in Example 3 of this application.

Figure 3A:
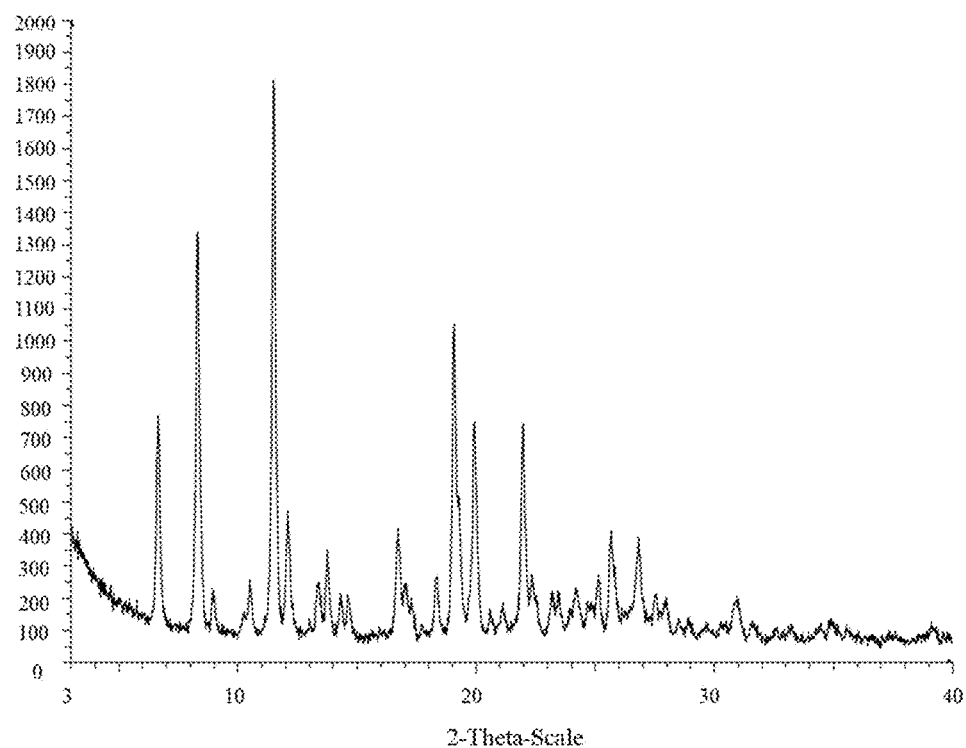
FIG. 3A shows a representative X-ray powder diffraction (XRPD) spectrum of crystalline form III of Compound 1.
Figure 3B:
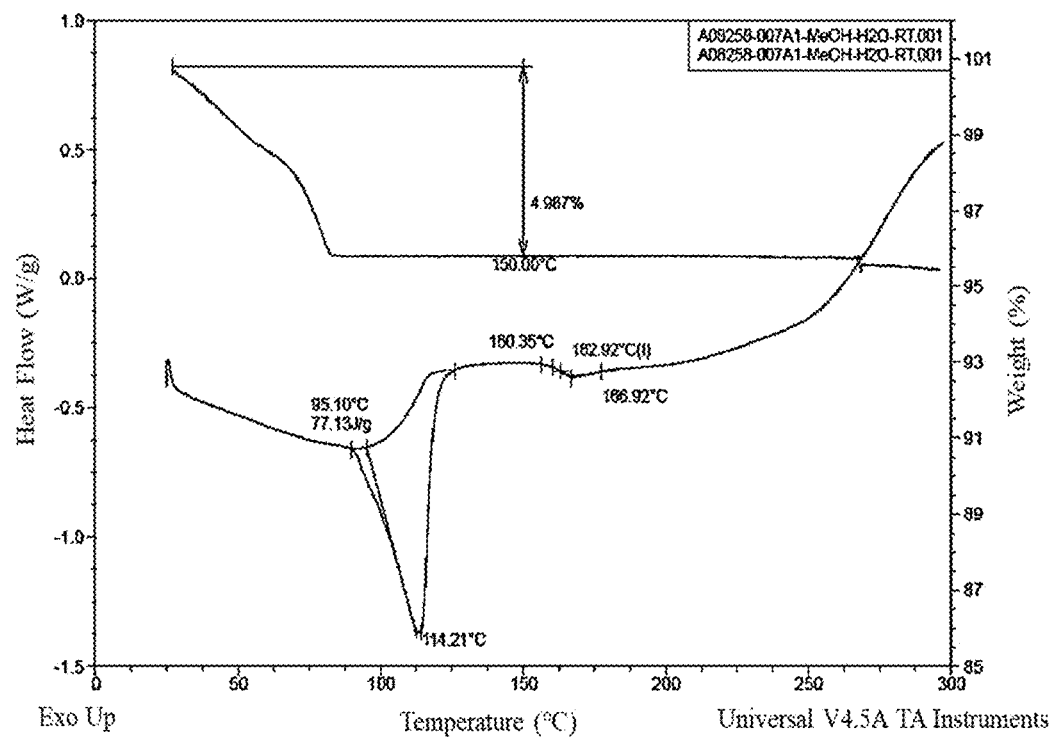
FIG. 3B shows a representative thermogravimetric analysis (TGA) and differential scanning calorimetry (DSC) analysis of crystalline form III of Compound 1.

In some embodiments, the Compound 1 is in a crystalline Form III. Characteristics of Form III include any of those described herein. In some embodiments, crystalline Form III can be characterized by (1) an X-ray powder diffraction (XRPD) pattern having one or more (e.g., 1, 2, 3, 4, 5, or 6) of the following peaks: 6.6, 8.3, 11.5, 19.1, 19.9, and 22.0 degrees 2 theta, ±0.2°; (2) an X-ray powder diffraction (XRPD) pattern having one or more (e.g., 4 or more, 8 or more, or all) of the following peaks: 6.6, 8.3, 11.5, 12.1, 16.7, 19.1, 19.9, 22.0, 25.7 and 26.8 degrees 2 theta, ±0.2°; (3) an XRPD pattern substantially the same as shown in FIG. 3A; (4) a Differential Scanning Calorimetry (DSC) pattern substantially the same as shown in FIG. 3B; or any combination thereof (e.g., (1) and (4), (2) and (4), (1), (2) and (4), or (3) and (4)). In some embodiments, the crystalline Form III can be characterized by an XRPD pattern having the major peaks (e.g., peaks with relative intensity of 20% or above, 30% or above, 40% or above, 50% or above, 60% or above, 70% or above, 80% or above, or 90% or above) of FIG. 3A or as shown in Table 3, degrees 2 theta, ±0.2°. In some embodiments, the crystalline Form III can be characterized by an XRPD pattern having all of the following peaks: 6.6, 8.3, 11.5, 19.1, 19.9, and 22.0 degrees 2 theta, ±0.2°. In some embodiments, the crystalline Form III can also be characterized by a DSC pattern having an endothermic peak with an onset temperature of about 95.1° C. and/or peak temperature at about 114.2° C. As shown in the Examples section, Form III was determined to be a di-hydrate. In some embodiments, the crystalline Form III is substantially the same as the crystalline Form III obtained in Example 3 of this application.

The Compound 1 in crystalline Form III can be prepared by methods described herein. For example, in some embodiments, Compound 1 in crystalline Form III can be prepared by a method comprising 1) dissolving Compound 1 in a first solvent, such as methanol, e.g., at room temperature, to form a solution; and then 2) adding an anti-solvent, such as water, to the solution to precipitate Compound 1. In some embodiments, the method further comprises stirring the mixture of Compound 1 in the first solvent and the anti-solvent, e.g., at room temperature, for a period of time (e.g., 1 hour to 5 days), to form a suspension; and optionally filtering and drying the precipitated Compound 1. Exemplified procedures for preparing Compound 1 in Form III are shown in Example 3 of this application.

In some embodiments, the Compound 1 is in a crystalline Form IV. Characteristics of Form IV include any of those described herein. In some embodiments, crystalline Form IV can be characterized by (1) an X-ray powder diffraction (XRPD) pattern having one or more (e.g., 1, 2, 3, 4, or 5) of the following peaks: 6.7, 8.6, 16.6, 18.9, and 19.2 degrees 2 theta, ±0.2°; (2) an X-ray powder diffraction (XRPD) pattern having one or more (e.g., 4 or more, 8 or more, 12 or more, or all) of the following peaks: 6.3, 6.7, 8.6, 14.6, 14.8, 15.7, 16.6, 17.6, 18.9, 19.2, 20.8, 21.2, and 23.2 degrees 2 theta, ±0.2°; (3) an XRPD pattern substantially the same as shown in FIG. 4A; (4) a Differential Scanning Calorimetry (DSC) pattern substantially the same as shown in FIG. 4B; or any combination thereof (e.g., (1) and (4), (2) and (4), (1), (2) and (4), or (3) and (4)). In some embodiments, the crystalline Form IV can be characterized by an XRPD pattern having the major peaks (e.g., peaks with relative intensity of 20% or above, 30% or above, 40% or above, 50% or above, 60% or above, 70% or above, 80% or above, or 90% or above) of FIG. 4A or as shown in Table 4, degrees 2 theta, ±0.2°. In some embodiments, the crystalline Form IV can be characterized by an XRPD pattern having all of the following peaks: 6.7, 8.6, 16.6, 18.9, and 19.2 degrees 2 theta, ±0.2°. In some embodiments, the crystalline Form IV can also be characterized by a DSC pattern having an endothermic peak with an onset temperature of about 273.0° C. and/or peak temperature at about 276.0° C. As shown in the Examples section, Form IV was determined to be an anhydrate. In some embodiments, the crystalline Form IV is substantially the same as the crystalline Form IV obtained in Example 3 of this application.

The Compound 1 in crystalline Form IV can be prepared by methods described herein. For example, in some embodiments, Compound 1 in crystalline Form IV can be prepared by a method comprising 1) dissolving Compound 1 in a first solvent, such as methanol, to form a solution, e.g., at 50° C.; and then 2) adding an anti-solvent, such as heptane, to the solution to precipitate Compound 1. In some embodiments, the method further comprises stirring the mixture of Compound 1 in the first solvent and the anti-solvent for a period of time (e.g., 0.2 hour to 2 hours); and optionally filtering and drying the precipitated Compound 1. In some embodiments, Compound 1 in crystalline Form IV can be prepared by a method comprising 1) dissolving Compound 1 in a suitable solvent under heat (e.g., up to the boiling point of the solvent), such as ethyl acetate, to form a solution; and then 2) cooling the solution to precipitate Compound 1, e.g., cooling to room temperature or below such as to 0-10° C. Exemplified procedures for preparing Compound 1 in Form IV are shown in Example 3 of this application.

As detailed in the Examples section, Compound 1 in Form IV can be more suited for various pharmaceutical uses compared to various other forms. For example, based on the interconversion study, Form 1, II and III all converted to Form IV at 50° C. or RT in the solvent systems without water, suggesting Form IV was the stable form. Form stability of Form IV in aqueous solution was evaluated and the result indicated Form IV was stable RT or 50° C. for 3 d and no hydrate was formed.

In some embodiments, Compound 1 can be in an amorphous form. Amorphous form of Compound 1 can be prepared by various methods described herein. As shown herein, the amorphous Compound 1 can be more suited for certain pharmaceutical uses compared to various other forms because of its superior solubility in biologically relevant fluids compared to the crystalline forms tested.

The methods of preparing the various crystalline forms of Compound 1 herein typically use one or more solvents. Suitable solvents are generally known, which include, but not limited to, THF, toluene, MeOH, ethanol, n-propanol, isopropanol, isobutanol, methyl tert-butyl ether, ether, isoamylol, butyl acetate, ethyl formate, 1,4-dioxane, n-butanol, tert-butanol, n-heptane, cyclohexane, methyl isobutyl ketone, dimethylbenzene, isobutyl acetate, 2-butanone, acetonitrile, acetone, ethyl acetate, isopropyl acetate, and water. The solvents can be used alone or in various combinations. Crystallization technics are generally known in the art. For example, Compound 1 can be slurried in one or more of the solvents at room temperature or under heat; Compound 1 can be heated in one or more of the solvents followed by cooling; Compound 1 can be dissolved in a solvent and then an antisolvent is added; and other techniques such as solid/liquid diffusion or liquid/liquid diffusion can also be used. The starting Compound 1 is not limited, which can be an amorphous solid. In some embodiments, the starting Compound 1 can also be a crystalline form, such as Form I. In some embodiments, the starting Compound 1 can also be a combination of an amorphous solid and crystalline form.

In some embodiments, the present disclosure also provides a solid form of Compound 1 that can be produced by any of the applicable methods described in the Examples section.

Compound 2

In some embodiments, the present disclosure is directed to Compound 2. Compound 2 and its synthesis were described in International Application Nos. PCT/CN2019/087772, filed on May 21, 2019, and/or PCT/CN2019/095947, filed on Jul. 15, 2019, the content of each of which is herein incorporated by reference in its entirety. Compound 2 should be understood as in its free base form to distinguish it from a salt formed with an external acid or base. Unless obvious from context, Compound 2 should be understood as in its free base form as discussed.

In some embodiments, Compound 2 can be in a solid form, such as an amorphous form, a crystalline form, or a combination thereof. In some embodiments, Compound 2 can be an amorphous form. In some embodiments, Compound 2 can be in a crystalline form (e.g., in any one or more crystalline forms A, B, C, and D as described herein). As used herein, when Compound 2 is said to exist or be in one particular solid form (e.g., a crystalline form), it should be understood that in some embodiments, it can exist predominantly in that particular form. However, in some embodiments, Compound 2 can also exist in the particular form, in a mixture with one or more other solid forms, including amorphous form. For example, when Compound 2 is said to exist or be in Form B, Compound 2 can exist predominantly in Form B, such as more than 80% by weight, more than 90% by weight, or more than 95% by weight of Compound 2 are in Form B, or no other solid form can be identified, for example, by XRPD; or Compound 2 can exist in Form B, in a mixture with one or more solid forms such as an amorphous form.

Compound 2 herein is typically in a substantially pure form. For example, in some embodiments, Compound 2 can have a purity of greater than 70%, preferably greater than 90% (e.g., greater than 95%, greater than 97%, greater than 98%, greater than 98.5%), by weight, by HPLC area, or both. In some embodiments, the Compound 2 can be characterized by a purity by weight and/or by HPLC area of about 70%, about 75%, about 80%, about 85%, about 90%, about 95%, about 97%, about 99%, or any ranges between the specified values. For example, in some embodiments, the Compound 2 can be characterized by a purity by HPLC area of about 70%, about 75%, about 80%, about 85%, about 90%, about 95%, about 97%, about 99%, or any ranges between the specified values. The substantially pure Compound 2 can be in a solid form (e.g., a crystalline form described herein, amorphous form, or a combination thereof) or in a solution, suspension, or another form. In some embodiments, the substantially pure Compound 2 can be in crystalline Form B. For the avoidance of doubt, a composition comprising the substantially pure Compound 2 herein and one or more other ingredients should be understood as a mixture of the substantially pure Compound 2 herein and the one or more other ingredients, for example, such composition can be obtained directly or indirectly from mixing the substantially pure Compound 2 with the one or more other ingredients, such as water, pharmaceutically acceptable excipients, etc.

In some embodiments, the Compound 2 is in a crystalline form. In some embodiments, the Compound 2 is in a crystalline Form A. Characteristics of Form A include any of those described herein. In some embodiments, crystalline Form A can be characterized by (1) an X-ray powder diffraction (XRPD) pattern having one or more (e.g., 1, 2, 3, or 4) of the following peaks: 6.2, 12.6, 14.8, and 19.9 degrees 2 theta, ±0.2°; (2) an X-ray powder diffraction (XRPD) pattern having one or more (e.g., 4 or more, 6 or more, or all) of the following peaks: 6.2, 12.6, 13.8, 14.8, 15.1, 18.0, 19.6 and 19.9 degrees 2 theta, ±0.2°; (3) an XRPD pattern substantially the same as shown in FIG. 5A; (4) a Differential Scanning Calorimetry (DSC) pattern substantially the same as shown in FIG. 5B; or any combination thereof (e.g., (1) and (4), (2) and (4), (1), (2) and (4), or (3) and (4)). In some embodiments, the crystalline Form A can be characterized by an XRPD pattern having the major peaks (e.g., peaks with relative intensity of 20% or above, 30% or above, 40% or above, 50% or above, 60% or above, 70% or above, 80% or above, or 90/o or above) of FIG. 5A or as shown in Table 9, degrees 2 theta, ±0.2°. In some embodiments, the crystalline Form A can be characterized by an XRPD pattern having all of the following peaks: 6.2, 12.6, 14.8, and 19.9 degrees 2 theta, ±0.2°. In some embodiments, the crystalline Form A can be characterized by an XRPD pattern having none of the following peaks: 7.3, 14.2, 15.7, and 16.3 degrees 2 theta, ±0.2°. In some embodiments, the crystalline Form A can be characterized by an XRPD pattern that does not have two or more, three or more, or all of the following peaks: 7.3, 14.2, 15.7, and 16.3 degrees 2 theta, ±0.2°. In some embodiments, the crystalline Form A can be characterized by an XRPD pattern having none of the following peaks: 14.5, 15.6, 20.2, and 38.6 degrees 2 theta, ±0.2°. In some embodiments, the crystalline Form A can be characterized by an XRPD pattern that does not have two or more, three or more, or all of the following peaks: 14.5, 15.6, 20.2, and 38.6 degrees 2 theta, ±0.2°. In some embodiments, the crystalline Form A can also be characterized by a DSC pattern having an endothermic peak with an onset temperature of about 286.4° C. and/or peak temperature at about 289.2° C. In some embodiments, the crystalline Form A is substantially the same as the crystalline Form A obtained in Example 5 or 6 of this application.

The Compound 2 in crystalline Form A can be prepared by methods described herein. For example, in some embodiments, Compound 2 in crystalline Form A can be prepared by a method comprising slurring Compound 2 in a solvent, such as ethyl acetate (EA or EtOAc), or by a method comprising 1) dissolving Compound 2 in an appropriate solvent, such as acetone, THF, 2-butanone and/or dichloromethane (DCM), and then 2) adding anti-solvent, such as n-heptane, to precipitate Compound 2. Exemplified procedures for preparing Compound 2 in Form A are shown in Example 5 and 6 of this application.

In some embodiments, the Compound 2 is in a crystalline Form B. Characteristics of Form B include any of those described herein. In some embodiments, crystalline Form B can be characterized by (1) an X-ray powder diffraction (XRPD) pattern having one or more (e.g., 1, 2, 3, 4, or 5) of the following peaks: 6.2, 12.6, 14.8, 19.0, and 19.8 degrees 2 theta, ±0.2°; (2) an X-ray powder diffraction (XRPD) pattern having one or more (e.g., 4 or more, 6 or more, 8 or more, or all) of the following peaks: 6.2, 12.6, 13.6, 14.5, 14.8, 17.8, 19.0, 19.8, 21.4, 26.3, 31.9 and 38.6 degrees 2 theta, ±0.20; (3) an XRPD pattern substantially the same as shown in FIG. 6A; (4) a Differential Scanning Calorimetry (DSC) pattern substantially the same as shown in FIG. 6B; or any combination thereof (e.g., (1) and (4), (2) and (4), (1), (2) and (4), or (3) and (4)). In some embodiments, the crystalline Form B can be characterized by an XRPD pattern having the major peaks (e.g., peaks with relative intensity of 20% or above, 30% or above, 40% or above, 50% or above, 60% or above, 70% or above, 80% or above, or 90% or above) of FIG. 6A or as shown in Table 10, degrees 2 theta, ±0.2°. In some embodiments, the crystalline Form B can be characterized by an XRPD pattern having all of the following peaks: 6.2, 12.6, 14.8, 19.0, and 19.8 degrees 2 theta, ±0.2°. In some embodiments, the crystalline Form B can be characterized by an XRPD pattern having at least one (e.g., 1, 2, 3, 4, 5, or 6) of the following peaks: 14.5, 17.8, 21.4, 26.3, 31.9 and 38.6 degrees 2 theta, ±0.2°. In some embodiments, the crystalline Form B can be characterized by an XRPD pattern having all of the following peaks: 6.2, 12.6, 14.8, 19.0, and 19.8 degrees 2 theta, ±0.2° and at least one (e.g., 1, 2, 3, 4, 5, or 6) of the following peaks: 14.5, 17.8, 21.4, 26.3, 31.9 and 38.6 degrees 2 theta, ±0.2°. In some embodiments, the crystalline Form B can be characterized by an XRPD pattern that has all of the following peaks: 6.2, 12.6, 14.8, 19.0, and 19.8 degrees 2 theta, ±0.2°; has two or more, three or more, or all of the following peaks: 14.5, 15.6, 20.2, and 38.6 degrees 2 theta, ±0.2°; and does not have either or both peaks at 7.3 and 14.2 degrees 2 theta, ±0.2°. In some embodiments, the crystalline Form B can also be characterized by a DSC pattern having an endothermic peak with an onset temperature of about 289.0° C. and/or peak temperature at about 290.1° C. In some embodiments, the crystalline Form B is substantially the same as the crystalline Form B obtained in Example 6 of this application.

The Compound 2 in crystalline Form B can be prepared by methods described herein. For example, in some embodiments, Compound 2 in crystalline Form B can be prepared by a method comprising 1) dissolving Compound 2 in a first solvent, e.g., at room temperature, such as methanol, to form a solution; and then 2) adding an anti-solvent, such as water, to the solution to precipitate Compound 2. In some embodiments, the method further comprises stirring the mixture of Compound 2 in the first solvent and the anti-solvent, e.g., at room temperature, for a period of time (e.g., 1-24 hours), to form a suspension; and optionally filtering and drying the precipitated Compound 2. In some embodiments, Compound 2 in crystalline Form B can be prepared from a different crystalline form. For example, in some embodiments, Compound 2 in crystalline Form B can be prepared by a method comprising 1) suspending Compound 2 (e.g., in Form A) in a solvent, such as methanol, to form a suspension; and 2) stirring the suspension at room temperature (RT) or under heat, such as at 50° C., for a period of time, such as 1 day, 3 days, etc. to form Compound 2 in crystalline Form B. The concentration of the suspension with the solvent can range from 15-100 mg/ml, such as about 100 mg/mL. Exemplified procedures for preparing Compound 2 in Form B are shown in Example 6 of this application.

In some embodiments, the Compound 2 is in a crystalline Form C. Characteristics of Form C include any of those described herein. In some embodiments, crystalline Form C can be characterized by (1) an X-ray powder diffraction (XRPD) pattern having one or more (e.g., 1, 2, or 3) of the following peaks: 6.2, 12.5, and 19.9 degrees 2 theta, ±0.2°; (2) an X-ray powder diffraction (XRPD) pattern having one or more (e.g., 4 or more, 8 or more, or all) of the following peaks: 6.2, 6.8, 7.3, 12.5, 14.2, 14.7, 15.7, 16.3, 19.9, 21.2, 22.9 and 26.1 degrees 2 theta, ±0.2°; (3) an XRPD pattern substantially the same as shown in FIG. 7A; (4) a Differential Scanning Calorimetry (DSC) pattern substantially the same as shown in FIG. 7B; or any combination thereof (e.g., (1) and (4), (2) and (4), (1), (2) and (4), or (3) and (4)). In some embodiments, the crystalline Form C can be characterized by an XRPD pattern having the major peaks (e.g., peaks with relative intensity of 20% or above, 30% or above, 40% or above, 50% or above, 60% or above, 70% or above, 80% or above, or 90% or above) of FIG. 7A or as shown in Table 11, degrees 2 theta, ±0.2°. In some embodiments, the crystalline Form C can be characterized by an XRPD pattern having all of the following peaks: 6.2, 12.5, and 19.9 degrees 2 theta, ±0.2°. In some embodiments, the crystalline Form C can be characterized by an XRPD pattern having at least one (e.g., 1, 2, 3, 4, 5, 6, 7, 8, or all) of the following peaks: 7.3, 14.2, 14.7, 15.7, 16.3, 19.9, 21.2, 22.9 and 26.1 degrees 2 theta, ±0.2°. In some embodiments, the crystalline Form C can be characterized by an XRPD pattern having all of the following peaks: 6.2, 12.5, and 19.9 degrees 2 theta, ±0.2° and at least one (e.g., 1, 2, 3, or 4) of the following peaks: 7.3, 14.2, 20.8, and 26.1 degrees 2 theta, ±0.2°. In some embodiments, the crystalline Form C can be characterized by an XRPD pattern that has all of the following peaks: 6.2, 12.5, and 19.9 degrees 2 theta, ±0.2°; and has either or both peaks at 7.3 and 14.2 degrees 2 theta, ±0.2°. In some embodiments, the crystalline Form C can also be characterized by a DSC pattern having an endothermic peak with an onset temperature of about 288.7° C. and/or peak temperature at about 289.4° C. In some embodiments, the crystalline Form C is substantially the same as the crystalline Form C obtained in Example 6 of this application.

The Compound 2 in crystalline Form C can be prepared by methods described herein. Exemplified procedures for preparing Compound 2 in Form C are shown in Example 6 of this application.

In some embodiments, the Compound 2 is in a crystalline Form D. Characteristics of Form D include any of those described herein. In some embodiments, crystalline Form D can be characterized by (1) an X-ray powder diffraction (XRPD) pattern having one or more (e.g., 1, 2, 3, or 4) of the following peaks: 5.6, 11.2, 16.9, and 22.6 degrees 2 theta, ±0.2°; (2) an X-ray powder diffraction (XRPD) pattern having one or more (e.g., 2 or more, 4 or more, 6 or more, or all) of the following peaks: 5.6, 11.2, 15.8, 16.1, 16.9, 21.4, 22.6 and 34.3 degrees 2 theta, ±0.2°; (3) an XRPD pattern substantially the same as shown in FIG. 8A; (4) a Differential Scanning Calorimetry (DSC) pattern substantially the same as shown in FIG. 8B; or any combination thereof (e.g., (1) and (4), (2) and (4), (1), (2) and (4), or (3) and (4)). In some embodiments, the crystalline Form D can be characterized by an XRPD pattern having the major peaks (e.g., peaks with relative intensity of 20% or above, 30% or above, 40% or above, 50% or above, 60% or above, 70% or above, 80% or above, or 90% or above) of FIG. 8A or as shown in Table 12, degrees 2 theta, ±0.2°. In some embodiments, the crystalline Form D can be characterized by an XRPD pattern having all of the following peaks: 5.6, 11.2, 16.9, and 22.6 degrees 2 theta, ±0.2°. In some embodiments, the crystalline Form D can be characterized by an XRPD pattern having at least one (e.g., 1, 2, 3, 4, 5, 6, 7, or 8) of the following peaks: 5.6, 11.2, 15.8, 16.1, 16.9, 21.4, 22.6 and 34.3 degrees 2 theta, ±0.2°. In some embodiments, the crystalline Form D can also be characterized by a DSC pattern having an endothermic peak with an onset temperature of about 286.9° C. and/or peak temperature at about 289.0° C. and an endothermic peak with an onset temperature of about 133.7° C. and/or peak temperature at about 140.8° C. In some embodiments, the crystalline Form D is substantially the same as the crystalline Form D obtained in Example 6 of this application.

The Compound 2 in crystalline Form D can be prepared by methods described herein. For example, in some embodiments, Compound 2 in crystalline Form D can be prepared by a method comprising 1) dissolving Compound 2 in a first solvent, such as isopropanol or isobutanol, to form a first solution, e.g., saturated solution; and then 2) dissolving Compound 2 in a second solvent, such as 2-butanone, acetone, or THF, to form a second solution, e.g., saturated solution; 3) mixing the first and second solution; and 4) precipitating Compound 2 through slow evaporation of solvents. In some embodiments, the first and second solvent can be isopropanol and 2-butanone, isopropanol and THF, isopropanol and acetone, or isobutanol and THF. Exemplified procedures for preparing Compound 2 in Form D are shown in Example 6 of this application.

As detailed in the Examples section, Compound 2 in Form B can be more suited for various pharmaceutical uses compared to various other forms. Solid state stability results indicated that Form B was both physically and chemically stable at 40° C./75% RH for 7 days, and the crystal form remained unchanged 92.5% RH for 10 days and 60° C. for 7 days. Further, based on the interconversion study, Form B was more stable than Form A and C.

In some embodiments, Compound 2 can be in an amorphous form. Amorphous form of Compound 2 can be prepared by various methods described herein.

The methods of preparing the various crystalline forms of Compound 2 herein typically use one or more solvents. Suitable solvents are generally known, which include, but not limited to, THF, toluene, MeOH, ethanol, n-propanol, isopropanol, isobutanol, methyl tert-butyl ether, ether, iso-amylol, butyl acetate, ethyl formate, 1,4-dioxane, n-butanol, tert-butanol, n-heptane, cyclohexane, methyl isobutyl ketone, dimethylbenzene, isobutyl acetate, 2-butanone, acetonitrile, acetone, ethyl acetate, isopropyl acetate, and water. The solvents can be used alone or in various combinations. Crystallization technics are generally known in the art. For example, Compound 2 can be slurried in one or more of the solvents at room temperature or under heat; Compound 2 can be heated in one or more of the solvents followed by cooling; Compound 2 can be dissolved in a solvent and then an antisolvent is added; and other techniques such as solid/liquid diffusion or liquid/liquid diffusion can also be used. The starting Compound 2 is not limited, which can be an amorphous solid or a crystalline form, such as Form A. In some embodiments, the starting Compound 2 can also be a combination of an amorphous solid and crystalline form.

In some embodiments, the present disclosure also provides a solid form of Compound 2 that can be produced by any of the applicable methods described in the Examples section.

In some embodiments, the present disclosure is also directed to any products produced by any of the methods herein, and methods of using such products.

Pharmaceutical Compositions

In various embodiments, the present disclosure also provides pharmaceutical compositions comprising a compound of the present disclosure, such as Compound 1 (e.g., Form IV) or Compound 2 (e.g., Form B) described herein, and optionally a pharmaceutically acceptable excipient. Non-limiting suitable excipients include, for example, encapsulating materials or additives such as absorption accelerators, antioxidants, binders, buffers, carriers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof. See also Remington's The Science and Practice of Pharmacy, 21st Edition, A. R. Gennaro (Lippincott, Williams & Wilkins, Baltimore, Md., 2005; incorporated herein by reference), which discloses various excipients used in formulating pharmaceutical compositions and known techniques for the preparation thereof.

In some embodiments, the present disclosure provides a pharmaceutical composition comprising one or more of the compounds of the present disclosure (e.g., Compound 1 in Form IV, amorphous Compound 1, Compound 2 in Form B, amorphous Compound 2, or any combination thereof). Typically, the pharmaceutical composition comprises a therapeutically effective amount of one or more of the compounds of the present disclosure (e.g., Compound 1 in Form IV, amorphous Compound 1, Compound 2 in Form B, amorphous Compound 2, or any combination thereof), and optionally a pharmaceutically acceptable excipient or carrier. In some embodiments, the pharmaceutical composition comprises one or more of the substantially pure compounds as described herein (e.g., Compound 1 and/or 2). In some embodiments, the pharmaceutical composition comprises one or more of the solid forms selected from Compound 1 in Form 1, Compound 1 in Form II, Compound 1 in Form III, Compound 1 in Form IV, amorphous Compound 1, Compound 2 in Form A, Compound 2 in Form B, Compound 2 in Form C, Compound 2 in Form D, and amorphous Compound 2.

In some specific embodiments, the pharmaceutical composition comprises Form IV of Compound 1. In some specific embodiments, the active ingredient in the pharmaceutical composition can comprise, consist essentially of, or consist of Form IV of Compound 1. In some embodiments, Compound 1 exists in the pharmaceutical composition essentially in Form IV, for example, at least 80% (e.g., at least 85%, at least 90%, at least 95%, by weight of total Compound 1) of Compound 1 exist in the pharmaceutical composition in Form IV. In some embodiments, the pharmaceutical composition is substantially free of Compound 1 in any other solid form, such as other crystalline forms. In some embodiments, the pharmaceutical composition is free or substantially free of Compound 1 in a crystalline form other than Form IV, for example, the pharmaceutical composition can in some embodiments include less than 10%, less than 5%, less than 2%, less than 1%, by weight of total Compound 1, or non-detectable amount, of Compound 1 in a crystalline form other than Form IV.

In some specific embodiments, the active ingredient in the pharmaceutical composition can comprise, consist essentially of, or consist of the Compound 1 in Form IV, amorphous form, or a mixture thereof. In some embodiments, Compound 1 can exist in the pharmaceutical composition as a mixture of Form IV and an amorphous form of the Compound 1, for example, at least 80% (e.g., at least 85%, at least 90%, at least 95%, by weight of total Compound 1) of Compound 1 can exist in the pharmaceutical composition in Form IV or an amorphous form.

In some specific embodiments, the pharmaceutical composition comprises Form B of Compound 2. In some specific embodiments, the active ingredient in the pharmaceutical composition can comprise, consist essentially of, or consist of Form B of Compound 2. In some embodiments, Compound 2 exists in the pharmaceutical composition essentially in Form B, for example, at least 80% (e.g., at least 85%, at least 90%, at least 95%, by weight of total Compound 2) of Compound 2 exist in the pharmaceutical composition in Form B. In some embodiments, the pharmaceutical composition is substantially free of Compound 2 in any other solid form, such as other salts or other crystalline forms. In some embodiments, the pharmaceutical composition is free or substantially free of Compound 2 in a crystalline form other than Form B, for example, the pharmaceutical composition can in some embodiments include less than 10%, less than 5%, less than 2%, less than 1%, by weight of total Compound 2, or non-detectable amount, of Compound 2 in a crystalline form other than Form B.

In some specific embodiments, the active ingredient in the pharmaceutical composition can comprise, consist essentially of, or consist of the Compound 2 in Form B, amorphous form, or a mixture thereof. In some embodiments, Compound 2 can exist in the pharmaceutical composition as a mixture of Form B and an amorphous form of the Compound B, for example, at least 80% (e.g., at least 85%, at least 90%, at least 95%, by weight of total Compound 2) of Compound 2 can exist in the pharmaceutical composition in Form B or an amorphous form.

Typically, the compound of the present disclosure is provided in an effective amount in the pharmaceutical composition. In certain embodiments, the effective amount is a therapeutically effective amount (e.g., amount effective for treating a cancer comprising a G12C mutation of KRAS, HRAS and/or NRAS, e.g., a KRAS G12C mutation, in a subject in need thereof). As used herein, a therapeutically effective amount of a compound of the present disclosure is an amount effective to treat a disease or disorder as described herein, which can depend on the recipient of the treatment, the disease or disorder being treated and the severity thereof, the composition containing the compound, the time of administration, the route of administration, the duration of treatment, the compound potency (e.g., for inhibiting KRAS G12C), its rate of clearance and whether or not another drug is co-administered.

Pharmaceutical compositions described herein can be prepared by any method known in the art of pharmacology. In general, such preparatory methods include bringing the active ingredient, such as the salt of the present disclosure, into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients useful for the manufacture of the pharmaceutical compositions herein include, for example, inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

The pharmaceutical composition can be formulated for any routes of administration, for example, oral administration. Typically, the pharmaceutical composition is a solid dosage form. However, in some embodiments, other dosage forms such as liquid, suspension, or semi-solid dosage forms can also be used.

Solid dosage forms for oral administration include for example capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient (e.g., the compounds of the present disclosure) can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Although the descriptions of pharmaceutical compositions provided herein are mainly directed to pharmaceutical compositions which are suitable for administration to humans, such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation. For veterinary use, a compound of the present disclosure can be administered as a suitably acceptable formulation in accordance with normal veterinary practice. The veterinarian can readily determine the dosing regimen and route of administration that is most appropriate for a particular animal.

The compounds of the present disclosure are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder, the activity of the specific active ingredient employed; the specific composition employed, the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

In some embodiments, all the necessary components for the treatment of KRAS-related disorder using a compound of the present disclosure either alone or in combination with another agent or intervention traditionally used for the treatment of such disease can be packaged into a kit. Specifically, in some embodiments, the present invention provides a kit for use in the therapeutic intervention of the disease comprising a packaged set of medicaments that include the compound disclosed herein as well as buffers and other components for preparing deliverable forms of said medicaments, and/or devices for delivering such medicaments, and/or any agents that are used in combination therapy with the compound of the present disclosure, and/or instructions for the treatment of the disease packaged with the medicaments. The instructions may be fixed in any tangible medium, such as printed paper, or a computer readable magnetic or optical medium, or instructions to reference a remote computer data source such as a world wide web page accessible via the internet.

Methods of Treatment

The compounds of the present disclosure and pharmaceutical compositions described herein are useful in treating and/or preventing diseases or disorders that are associated with RAS, e.g., KRAS G12C.

In some embodiments, the present disclosure provides a method of inhibiting RAS-mediated cell signaling comprising contacting a cell with an effective amount of one or more compounds of the present disclosure (e.g., Compound 1 and/or 2). Inhibition of RAS-mediated signal transduction can be assessed and demonstrated by a wide variety of ways known in the art. Non-limiting examples include a showing of (a) a decrease in GTPase activity of RAS; (b) a decrease in GTP binding affinity or an increase in GDP binding affinity; (c) an increase in $K_{off}$ of GTP or a decrease in $K_{off}$ of GDP; (d) a decrease in the levels of signaling transduction molecules downstream in the RAS pathway, such as a decrease in pMEK, pERK, or pAKT levels; and/or (e) a decrease in binding of RAS complex to downstream signaling molecules including but not limited to Raf. Kits and commercially available assays can be utilized for determining one or more of the above.

In some embodiments, the present disclosure provides a method of inhibiting KRAS, HRAS, and/or NRAS G12C in a cell, the method comprising contacting the cell with an effective amount of one or more compounds of the present disclosure (e.g., Compound 1 and/or 2).

In some embodiments, the present disclosure provides a method of treating a disease or disorder, e.g., a cancer associated with G12C mutation of KRAS, HRAS and/or NRAS, such as a cancer associated with KRAS G12C, in a subject in need thereof. In some embodiments, the method comprises administering to the subject a therapeutically effective amount of a compound of the present disclosure (e.g., Compound 1 in Form IV, amorphous Compound 1, Compound 2 in Form B, amorphous Compound 2, or any combination thereof) or a therapeutically effective amount of a pharmaceutical composition described herein.

In some embodiments, a method for treatment of cancer is provided, the method comprising administering to a subject in need thereof an effective amount of any of the compound of the present disclosure (e.g., Compound 1 in Form IV, amorphous Compound 1, Compound 2 in Form B, amorphous Compound 2, or any combination thereof) or a pharmaceutical composition comprising the compound of the present disclosure. In some embodiments, the cancer comprises a G12C mutation of KRAS, HRAS and/or NRAS, e.g., a KRAS G12C mutation. Determining whether a tumor or cancer comprises a G12C mutation of KRAS, HRAS and/or NRAS is known in the art, for example, as described in US2018/0334454. In various embodiments, the cancer can be pancreatic cancer, endometrial cancer, colorectal cancer or lung cancer (e.g., non-small cell lung cancer). In some embodiments, the cancer is a hematological cancer (e.g., described herein). In some embodiments, the cancer is MYH associated polyposis. In some embodiments, the cancer is gall bladder cancer, thyroid cancer, or bile duct cancer. Non-limiting examples of cancer also include acute myeloid leukemia, cancer in adolescents, adrenocortical carcinoma childhood, AIDS-related cancers (e.g. Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, Burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myeloproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, Hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer multiple endocrine neoplasia syndromes, multiple myeloma/plasma cell neoplasm, mycosis fungoides, myelodysplasia syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or viral-induced cancer.

In some embodiments the present disclosure provides a method of treating a disease or disorder (e.g., a cancer described herein) in a subject in need thereof, wherein the method comprises determining if the subject has a G12C mutation of KRAS, HRAS and/or NRAS, e.g., KRAS G12C mutation, and if the subject is determined to have the KRAS, HRAS and/or NRAS G12C mutation, e.g., KRAS G12C mutation, then administering to the subject a therapeutically effective dose of at least one compound of the present disclosure (e.g., Compound 1 in Form IV, amorphous Compound 1, Compound 2 in Form B, amorphous Compound 2, or any combination thereof) or a pharmaceutical composition comprising the at least one compound of the present disclosure.

G12C mutation of KRAS, HRAS and/or NRAS has also been identified in hematological malignancies (e.g., cancers that affect blood, bone marrow and/or lymph nodes). Accordingly, certain embodiments are directed to a method of treating hematological malignancy in a subject in need thereof, the method typically comprises administration of a compound of the present disclosure (e.g., in the form of a pharmaceutical composition) to the subject. Such malignancies include, but are not limited to leukemias and lymphomas, such as Acute lymphoblastic leukemia (ALL), Acute myelogenous leukemia (AML), Chronic lymphocytic leukemia (CLL), small lymphocytic lymphoma (SLL), Chronic myelogenous leukemia (CML), Acute monocytic leukemia (AMoL) and/or other leukemias. In some embodiments, the hematological malignancy can also include lymphomas such as Hodgkins lymphoma or non-Hodgkins lymphoma, plasma cell malignancies such as multiple myeloma, mantle cell lymphoma, and Waldenstrom's macroglubunemia.

Compounds of the present disclosure can be used as a monotherapy or in a combination therapy. In some embodiments, the combination therapy includes treating the subject with a chemotherapeutic agent, therapeutic antibody, radiation, cell therapy, or immunotherapy. In some embodiments, compounds of the present disclosure can also be co-administered with an additional pharmaceutically active compound, either concurrently or sequentially in any order, to a subject in need thereof (e.g., a subject having a cancer associated with KRAS G12C mutation as described herein). In some embodiments, the additional pharmaceutically active compound can be a chemotherapeutic agent, a therapeutic antibody, etc. Any of the known chemotherapeutics can be used in combination with the compounds of the present disclosure. In some embodiments, compounds of the present disclosure can also be used in combination with a radiation therapy, hormone therapy, cell therapy, surgery and immunotherapy, which therapies are well known to those skilled in the art.

The administering herein is not limited to any particular route of administration. For example, in some embodiments, the administering can be orally, nasally, transdermally, pulmonary, inhalationally, buccally, sublingually, intraperitoneally, subcutaneously, intramuscularly, intravenously, rectally, intrapleurally, intrathecally or parenterally. In some embodiments, the administering is orally.

Dosing regimen including doses can vary and can be adjusted, which can depend on the recipient of the treatment, the disease or disorder being treated and the severity thereof, the composition containing the compound, the time of administration, the route of administration, the duration of treatment, the compound potency, its rate of clearance and whether or not another drug is co-administered.

Definitions

"Compound(s) of the present disclosure" as used herein refers to Compound 1, Compound 2, an isolated form thereof, a substantially pure form thereof, a solid form thereof including crystalline forms, amorphous forms, hydrates and/or solvates.

As used herein, the term "about" modifying an amount related to the invention refers to variation in the numerical quantity that can occur, for example, through routine testing and handling; through inadvertent error in such testing and handling; through differences in the manufacture, source, or purity of ingredients employed in the invention; and the like. As used herein, "about" a specific value also includes the specific value, for example, about 10% includes 10%. Whether or not modified by the term "about", the claims include equivalents of the recited quantities. In one embodiment, the term "about" means within 20% of the reported numerical value.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a compound of the present disclosure to a subject in need of such treatment.

The term "therapeutically effective amount," as used herein, refers to that amount of a therapeutic agent (e.g., any one or more of the Compounds of the present disclosure) sufficient to result in amelioration of one or more symptoms of a disorder or condition (e.g., a cancer associated with KRAS G12C mutation), or prevent appearance or advancement of a disorder or condition, or cause regression of or cure from the disorder or condition.

The term "subject" (alternatively referred to herein as "patient") as used herein, refers to an animal, preferably a mammal, most preferably a human, who has been the object of treatment, observation or experiment. In any of the embodiments described herein, the subject can be a human.

EXAMPLES

Example 1. General Methods

Materials: the starting materials, reagents, solvents, etc. are generally available through commercial sources.

$^1$H NMR was performed using Bruker Advance 300 equipped with automated sampler (B-ACS 120).

POWDER X-RAY DIFFRACTION (XRPD): The solid samples were examined using X-ray diffractometer (Bruker D8 advance). The system is equipped with LynxEye detector. The X-ray wavelength is 1.5418 Å. The samples were scanned from 3 to 40° 2θ, at a step size 0.02° 2θ. The tube voltage and current were 40 KV and 40 mA, respectively.

Polarizing microscope analysis (PLM): Light microscopy was performed using a Polarizing Microscope ECLIPSE LV100POL (Nikon, JPN).

TGA ANALYSIS: TGA was carried out on a TGA Q500 or Discovery TGA 55 (TA Instruments, US). The sample was placed into an open tared aluminum pan, automatically weighed, and inserted into the TGA furnace. The sample was heated at a rate of 10° C./min from room temperature (RT) to the final temperature.

DSC ANALYSIS: DSC was performed using a DSC Q200 or Discovery DSC 250 (TA Instruments, US). The sample was placed into an aluminum pin-hole hermetic pan and the weight was accurately recorded. The sample was heated at a rate of 10° C./min from 25° C. to the final temperature.

Dynamic Moisture Sorption Analysis (DVS):

Method 1. Used for studies with solid state of Compound 1. Moisture sorption/desorption data was collected on a DVS Intrinsic (SMS, UK). The sample was placed into a tared sample chamber and automatically weighed. The sample was dried at 40° C. until the dm/dt was less than 0.002% and cooled to 25° C. Set the instrument parameters as below.

Step time (min): 60 min
Sample temperature: 25° C.
Cycle: Full cycle
Adsorption: 0, 10, 20, 30, 40, 50, 60, 70, 80, 90
Desorption: 80, 70, 60, 50, 40, 30, 20, 10, 0
Save Data Rate: 5 s
Total flow rate: 200 sccm
Post experiment total flow: 200 sccm Method 2. Used for studies with solid state of Compound 2. Moisture sorption/desorption data was collected on IGAsorp Dynamic Moisture Sorption Analyzer. The sample was placed into a tarred sample chamber and automatically weighed. The sample was dried at 50° C. until the humidity was less than 0.3% and cooled to 25° C. The instrument parameters were set as given below.

Sample temperature: 25° C.
Temperature stability: 0.1° C./min
Flow rate: 250 mL/min
Scans: 2
Mode: F1
Min time: 30 min
Time out: 120 min Wait until: 98%
Beginning: with adsorption scan
Adsorption: 0, 10, 20, 30, 40, 50, 60, 70, 80, 90
Desorption: 80, 70, 60, 50, 40, 30, 20, 10, 0

HPLC Analysis:

Method 1. a representative HPLC method is shown below, which can be used, for example, to analyze the purity, solubility, and stability of Compound 1 herein.

| | |
|---|---|
| Instrument | Agilent 1260 series |
| Column | Ascentis Express C18 4.6 × 100 mm, 2.7 μm |
| Column temperature | 40° C. |
| Mobile phase | A: 0.1% TFA in water |
| | B: 0.1% TFA in ACN |
| Gradient condition | 0 min: 30% |
| (% of B) | 8.0 min: 60% |
| | 10.0 min: 90% |
| | 12.0 min: 90% |
| Flow rate | 1.0 mL/min |
| Injection volume | 5 μL |
| UV wavelength | 220 nm |
| Post time | 3 min |
| Diluent | ACN (acetonitrile) |

Method 2. HPLC analysis was performed with an Agilent HPLC 1260 series instrument. A representative HPLC method used for purity, solubility and stability study for Compound 2 analysis.

| | | | | |
|---|---|---|---|---|
| Column | Diamonsil C18, 4.6*200 mm, 5 μm | | | |
| Mobile Phase | A: 0.01% TFA in water | | | |
| | B: ACN | | | |
| Gradient | Time (min) | 0 | 10 | 20 |
| | Mobil phase B % | 20% | 90% | 90% |
| Column Temperature | 30° C. | | | |
| Detector | DAD; 210 nm | | | |
| Flow Rate | 1.0 mL/min | | | |
| Injection Conc. | 0.4 mg/mL | | | |
| Injection Volume | 2 μL | | | |
| Run Time | 20 minutes | | | |
| Post Time | 5 minutes | | | |
| Diluent | ACN/water (1:1) | | | |

Example 2. Preparation and Solid State Characterization of Compound 1

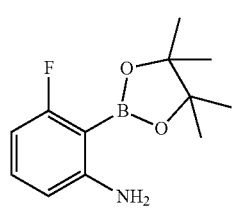

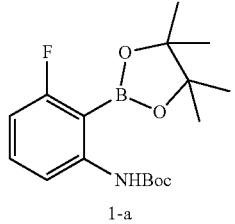

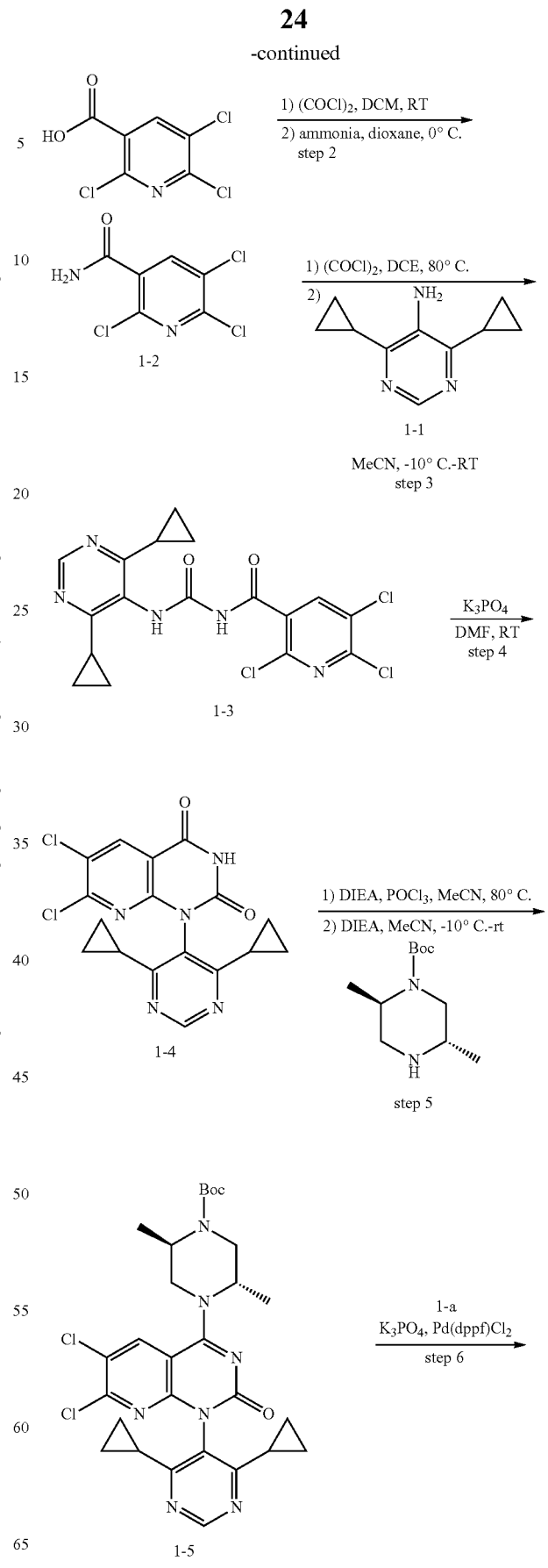

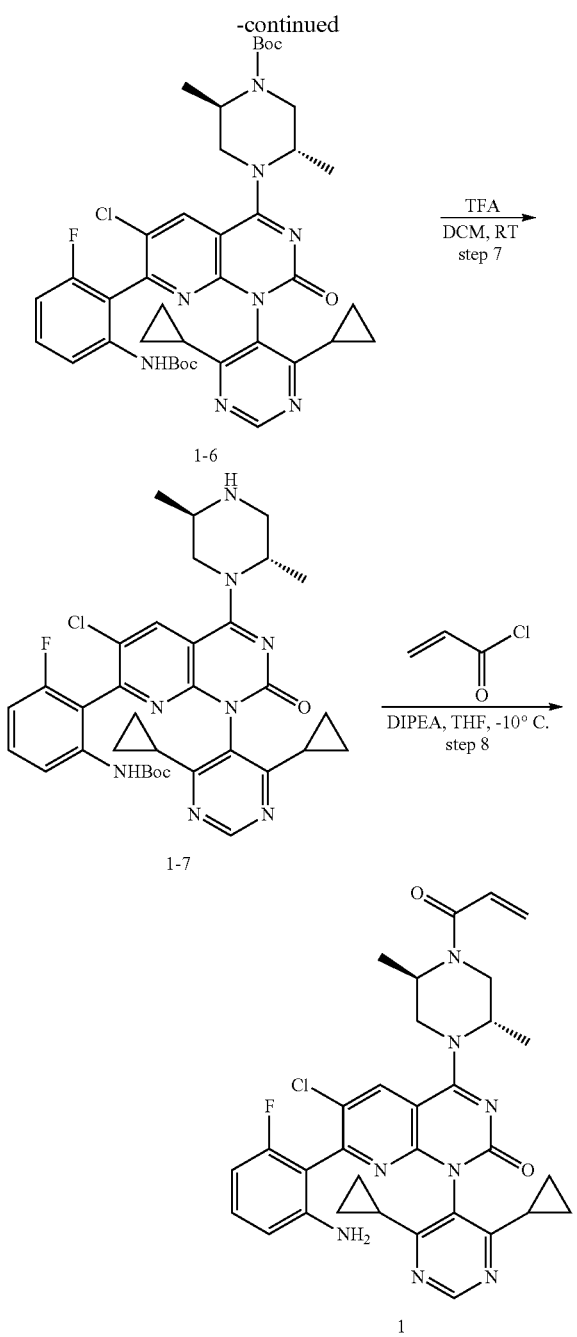

Compound 1-1 was prepared following the procedure for the synthesis of compound 1-1 in example 1 of WO2020233592A1.

Step 1: A mixture of 3-fluoro-2-(4,4,5,5-tetramethyl-1,3,2-dioxaborolan-2-yl)aniline (10 g, 42.18 mmol) and di-tert-butyl decarbonate (12.6 g, 57.73 mmol) in toluene (10 mL) was heated at 80° C. for 5 hours. The mixture was concentrated and the residue was purified by flash column chromatography on silica gel (ethyl acetate/petroleum ether=0/1 to 1/3) to afford 1-a.

Step 2: To a suspension of 2,5,6-trichloronicotinic acid (10 g, 44 mmol) in dichloromethane (100 mL) at room temperature was added oxalyl chloride (11 g, 88 mmol) and 15 drops of dry DMF. After 30 minutes, the resulting solution was concentrated to give a residue which was dissolved in dioxane (40 mL). 100 mL of ammonia (28% $NH_3$ in water) was added dropwise at 0° C., and the reaction mixture was allowed to stir for additional 10 minutes, filtered, and washed with water. The filter cake was collected and freeze-dried to afford 1-2.

Step 3: A solution of 1-2 (30 g, 133.07 mmol) in DCE (300 mL) was treated with oxalyl chloride (33.7 g, 265.52 mmol). The mixture was stirred at 80° C. for 45 minutes and then concentrated. The residue was dissolved in dichloromethane (60 mL) and concentrated. The residue was dissolved in THF (120 mL) and cooled to −10° C., and a solution of 1-1 (23.3 g, 139.96 mmol) in THF (120 mL) was added. The resulting mixture was stirred at room temperature for 2 hours. The mixture was extracted between EtOAc and water. The organic layer was washed with brine and concentrated. The residue was slurried in EtOAc/PE (1/10) and filtered. The filter cake was dried to afford 1-3.

Step 4: To a stirred solution of 1-3 (10 g, 25.63 mmol) in DMF (60 mL) was added $K_3PO_4$ (6.5 g, 30.62 mmol). The resulting mixture was then stirred at room temperature for 2 hours. The reaction was quenched with HCl (1N) and filtered. The filter cake was washed with water, and then slurried in MeCN. Filtered, and the filter cake was dried to afford 1-4.

Step 5: To a solution of 1-4 (10 g, 25.63 mmol) and DIEA (8.3 g, 64.22 mmol) in MeCN (50 mL) was added $POCl_3$ (7.9 g, 51.53 mmol) dropwise at room temperature. The resulting solution was stirred at 80° C. for 45 minutes, followed by addition of DIEA (8.3 g, 64.22 mmol) and a solution of (2R,5S)-tert-butyl 2,5-dimethylpiperazine-1-carboxylate (6.6 g, 30.80 mmol) in MeCN (50 mL) dropwise at −10° C. After stirring at room temperature for 1 hour, the reaction was then quenched with ice-water and the mixture was extracted with ethyl acetate. The combined organic layers were dried over anhydrous sodium sulfate and concentrated. The residue was purified by flash column chromatography on silica gel (ethyl acetate/petroleum ether=0/1 to 3/1) to afford 1-5.

Step 6: A mixture of 1-5 (2 g, 3.41 mmol), 1-a (1.38 g, 4.09 mmol), Pd(dppf)$Cl_2$ (250 mg, 0.34 mmol) and $K_3PO_4$ (1.45 g, 6.83 mmol) in toluene (20 mL) was stirred at 80° C. for 2 hours under nitrogen atmosphere. The mixture was diluted with water and extracted with ethyl acetate. The combined organic layers were dried over anhydrous $Na_2SO_4$ and concentrated. The residue was purified by flash column chromatography on silica gel (ethyl acetate/petroleum ether=0/1 to 3/1) to afford 1-6.

Step 7: A mixture of 1-6 (5 g, 6.57 mmol) in DCM (25 mL) was treated with TFA (9 g), and the mixture was stirred at 25° C. for 3 hours. The reaction was quenched with an aqueous $Na_2CO_3$ solution and the mixture was separated. The organic layer was washed with water twice and then concentrated to afford 1-7.

Step 8: To a mixture of 1-7 (2 g, 3.56 mmol) and DIPEA (550 mg, 4.26 mmol) in THF (40 mL) was added acryloyl chloride (322 mg, 3.56 mmol) at −10° C. The mixture was stirred for 1 hour and quenched with an aqueous citric acid solution. The mixture was extracted with EtOAc, and the organic layer was washed with water. The organic layer was concentrated and the residue was purified by flash column chromatography on silica gel (ethyl acetate/petroleum ether=0/1 to 3/1) to afford 1. The compound 1 was lyophilized in MeCN/$H_2O$ to afford an amorphous form. LCMS (ESI, m/z): [M+H]$^+$=615.3; HNMR (400 MHz, DMSO-$d_6$, ppm): δ 8.74 (s, 1H), 8.52-8.35 (m, 1H), 7.16-7.07 (m, 1H), 6.94-6.76 (m, 1H), 6.51 (d, J=6.0 Hz, 1H), 6.38 (t, J=6.6 Hz, 1H), 6.20 (dd, J=12.6, 1.8 Hz, 1H), 5.76 (dd, J=12.6, 1.6 Hz, 1H), 4.91-4.80 (m, 2H), 4.51-3.50 (m, 6H), 1.91-1.65 (m, 1H), 1.45-1.15 (m, 6H), 1.10-0.70 (m, 8H). FNMR (376 MHz, DMSO-$d_6$, ppm): δ −114.30 (1F).

Compound 1 thus obtained was found to be an amorphous solid. TGA showed two steps of weight loss prior to 200° C., 1.4% followed by 0.6% loss, one broad endothermic peak was observed by DSC at 35° C. Additionally, Tg of this amorphous solid is about 154° C. by DSC.

| Item | Result |
|---|---|
| PLM | No birefringence |
| XRPD | Amorphous |
| DSC, endo Onset/Peak, ΔH | 35.27/67.95° C., 30.0 J/g Tg: 154° C. |
| TGA wt loss %/@T (° C.) | 1.4% at RT-150° C., 0.6% at 150-200° C. |

Example 3. Polymorph Screening of Compound 1

This example screens polymorphs of Compound 1.

Evaporative Crystallization: Appropriate amounts of Compound 1 were added into 2.5 mL of each of the 13 solvents (MeOH, EtOH; IPA (isopropyl alcohol); IBA (isobutyl alcohol); MEK (methyl ethyl ketone or 2-butanone); THF (tetrahydrofuran); ACN (acetonitrile); MTBE (methyl tert-Butyl ether); Acetone; Water; Toluene; EA (ethyl acetate); IPAC (isopropyl acetate)) to make suspensions respectively. After stirring, 2 mL of each of the 13 drug suspensions were filtered. The filtrate was then used for either a binary solvent screening or a single solvent evaporation study.

For binary evaporation studies: the saturated drug solutions (filtrates) were distributed in a 96-well plate. Each well contained two different filtrates and the volume of each filtrate was 100 μL. The plate was covered by sealing film with pin holes and allowed to evaporate in an operating laboratory fume hood under ambient conditions. All samples obtained were glassy state or amorphous, and no crystalline samples were prepared.

For single solvent evaporation studies: the saturated drug solutions (filtrates) were used for slow evaporation study. After dryness, solid samples were tested by XRPD. Only 2 crystalline samples were obtained. Pattern 1 was obtained in IPA, Form II was obtained in isobutanol, and other samples were all glassy or amorphous.

Slurry Study: The suspension prepared in IPA, water, MTBE and heptane were slurried at RT for 3 days, and at 50° C. for 1 day. Solid samples were collected by filtration and analyzed by XRPD at a specific time. If new XRPD patterns were identified, the sample was further analyzed by DSC and TGA.

Alternatively, amorphous Compound 1 (~20 mg) was weighed into vials and 0.5 mL of the selected mixed solvents were added. The suspensions were stirred at RT for several days or at 50° C. for 1 day. Solid samples were collected by filtration and analyzed by XRPD at a specific time. If new XRPD patterns were identified, the sample was further analyzed by DSC and TGA.

Anti-solvent Precipitation: Amorphous Compound 1 (~20 mg) was dissolved into 0.1 or 0.2 mL of a solvent at RT, and then an anti-solvent was added slowly until precipitation appeared or up to 1 mL. If precipitation occurred, products were characterized accordingly. The amorphous Compound 1 has high solubility in the most solvents, and low solubility in MTBE, water and heptane.

In the polymorph screening, five XRPD Patterns (FIG. 11) were generated, and four forms were identified including 2 anhydrates and 2 hydrates. Pattern 1 was the XRPD pattern of a wet cake, and it was not stable. Patterns 2 to 5 were identified as Form I, II, III and IV, respectively. The details were summarized as follows.

Pattern 1 was the wet cake of the samples prepared by evaporation or slurry in IPA. Pattern 1 can convert to Form I during the air drying, and no pure Pattern 1 was prepared. Hence, Pattern 1 was an unstable solvate/hydrate, and it was not assigned as a Form.

Form I was obtained by slurry in water, IPA, MTBE, THF/heptane and EA/heptane, or anti-solvent precipitation from EA/MTBE and THF/MTBE. Only Form I prepared in IPA had one sharp melting peak, which may be attributed to the residual solvents or the quality of the crystals.

Scale-up of Form I: Amorphous Compound (~250 mg) was slurried in 1.5 mL of IPA at RT for 3 days. The sample was collected by filtration and characterized after dried at 50° C. for 5 h. Form I (~180 mg) was successfully prepared with a yield of 72%. Thermal profiles showed that there was one melting peak with onset temperature of 239° C. and 0.17% weight loss at RT to 200° C. (FIG. 1B), and NMR showed that there was no residual solvent, suggesting Form I was an anhydrous form.

Representative XRPD and DSC spectra of Form I are shown in FIG. 1A-1B. A table of XRPD peaks are shown below in Table 1.

TABLE 1

XRPD peak table for form I.

| Angle 2-Theta ° | Intensity % | Intensity Count | d value Angstrom |
|---|---|---|---|
| 6.857 | 64.3 | 470 | 12.88103 |
| 7.179 | 26.9 | 197 | 12.30411 |
| 9.345 | 13.4 | 98 | 9.45632 |
| 10.565 | 22.8 | 167 | 8.36705 |
| 11.351 | 66.8 | 488 | 7.78923 |
| 11.525 | 68.5 | 501 | 7.67179 |
| 12.997 | 100 | 731 | 6.80602 |
| 13.903 | 37.3 | 273 | 6.36481 |
| 14.494 | 23.3 | 170 | 6.10641 |
| 14.834 | 72.8 | 532 | 5.96698 |
| 15.274 | 22.2 | 162 | 5.79621 |
| 16.533 | 14.9 | 109 | 5.35766 |
| 16.838 | 35.8 | 262 | 5.26114 |
| 17.092 | 40.1 | 293 | 5.18349 |
| 17.368 | 53.5 | 391 | 5.10172 |
| 17.792 | 50.9 | 372 | 4.98123 |
| 18.056 | 90.7 | 663 | 4.90898 |
| 18.799 | 26 | 190 | 4.71647 |
| 19.415 | 56.6 | 414 | 4.56829 |
| 20.952 | 42.1 | 308 | 4.23651 |
| 21.846 | 27.6 | 202 | 4.06505 |
| 22.826 | 82.1 | 600 | 3.8927 |
| 23.736 | 38.4 | 281 | 3.74557 |
| 24.7 | 44.6 | 326 | 3.60144 |
| 25.671 | 13.4 | 98 | 3.46743 |
| 26.213 | 33.1 | 242 | 3.397 |
| 26.954 | 11.1 | 81 | 3.30525 |
| 28.067 | 25.6 | 187 | 3.17665 |
| 29.322 | 18.9 | 138 | 3.04351 |
| 30.705 | 18.3 | 134 | 2.90945 |
| 31.206 | 23.7 | 173 | 2.86385 |
| 32.316 | 16.7 | 122 | 2.768 |
| 34.733 | 12.4 | 91 | 2.58074 |
| 36.292 | 11.9 | 87 | 2.47333 |
| 38.012 | 13.3 | 97 | 2.36528 |

Form II was generated in the mixed solvents of acetone-heptane or acetone-water, and acetone-water was chosen as the solvent to prepare Form II.

Scale-up of Form II: Amorphous Compound 1 (~100 mg) was dissolved in 0.2 mL of acetone at RT. Sticky sample appeared immediately after adding 0.2 mL of water. However, it became suspension after stirring at RT for 3 days. The sample was collected by filtration and characterized after dried at 50° C. for 5 h. Form II (~65 mg) was successfully prepared with the yield of 63%.

DSC results showed that there were two endothermic peaks with onset temperature of 111° C. and 171° C., respectively. About 3.1% weight loss prior to 150° C. was observed by TGA (FIG. 2B), but only 0.1% residual acetone was detected by NMR. Hence, the weight loss was due to water, and Form II was a mono-hydrate (theoretical water content of the mono-hydrate is 2.8%). However it was not a stable hydrate, and dehydration occurred at low temperature.

Representative XRPD and DSC spectra of Form II are shown in FIG. 2A-2B. A table of XRPD peaks are shown below in Table 2.

TABLE 2

XRPD peak table for form 11.

| Angle 2-Theta ° | Intensity % | Intensity Count | d value Angstrom |
|---|---|---|---|
| 3.804 | 78.1 | 474 | 23.21113 |
| 6.175 | 49.4 | 300 | 14.30246 |
| 8.133 | 53.9 | 327 | 10.86239 |
| 9.376 | 43.5 | 264 | 9.42488 |
| 10.213 | 30.6 | 186 | 8.65464 |
| 11.649 | 28.8 | 175 | 7.5904 |
| 13.055 | 26.9 | 163 | 6.77625 |
| 13.523 | 19.4 | 118 | 6.54273 |
| 14.955 | 44 | 267 | 5.91917 |
| 15.578 | 71.8 | 436 | 5.68381 |
| 16.246 | 16.1 | 98 | 5.45168 |
| 16.727 | 21.4 | 130 | 5.29594 |
| 17.679 | 14 | 85 | 5.01285 |
| 18.343 | 29.8 | 181 | 4.83287 |
| 18.817 | 100 | 607 | 4.71218 |
| 19.131 | 34.6 | 210 | 4.63559 |
| 19.609 | 25 | 152 | 4.52365 |
| 20.089 | 32.9 | 200 | 4.41652 |
| 21.005 | 34.9 | 212 | 4.2259 |
| 21.464 | 22.1 | 134 | 4.13655 |
| 22.377 | 29.7 | 180 | 3.96986 |
| 23.066 | 20.8 | 126 | 3.85277 |
| 24.532 | 18.8 | 114 | 3.62583 |
| 24.984 | 34.4 | 209 | 3.56121 |
| 25.256 | 25.2 | 153 | 3.52349 |
| 26.043 | 35.3 | 214 | 3.41869 |
| 27.358 | 25.9 | 157 | 3.25731 |
| 27.99 | 20.1 | 122 | 3.18524 |
| 28.684 | 17.3 | 105 | 3.10973 |
| 30.064 | 18.1 | 110 | 2.96998 |
| 30.646 | 14.2 | 86 | 2.91494 |
| 35.513 | 13.5 | 82 | 2.52581 |

Form III was obtained by precipitation in MeOH/water. Form III (115 mg) was successfully prepared with a yield of 73% as the procedure below.

Scale-up of Form III: Amorphous Compound 1 (~100 mg) was dissolved in 0.3 mL MeOH at RT, and then 0.2 mL of water was added slowly. Sticky sample appeared immediately, and the solids appeared after stirring for 2 h. The solid sample was collected by filtration after stirring for another 2 h, and then dried at RT overnight.

Thermal profiles showed that there was one endothermic peak with onset temperature of 95° C. and 5% weight loss prior to 150° C. (FIG. 3B). No residual solvent was detected by NMR. Hence, Form III should be a di-hydrate (theoretical water content of the di-hydrate is 5.5%), which was still unstable and dehydration occurred at low temperature, and it converted to amorphous form after dehydration.

Representative XRPD and DSC spectra of Form III are shown in FIG. 3A-3B. A table of XRPD peaks are shown below in Table 3.

TABLE 3

XRPD peak table for form III.

| Angle 2-Theta ° | Intensity % | Intensity Count | d value Angstrom |
|---|---|---|---|
| 6.608 | 42.5 | 774 | 13.36587 |
| 8.278 | 73.7 | 1342 | 10.67303 |
| 8.935 | 12.6 | 229 | 9.88962 |
| 10.243 | 8.4 | 152 | 8.62925 |
| 10.482 | 14.3 | 260 | 8.43279 |
| 11.483 | 100 | 1820 | 7.69957 |
| 12.076 | 25.8 | 470 | 7.32286 |
| 12.998 | 6.8 | 123 | 6.80556 |
| 13.355 | 13.7 | 249 | 6.62426 |
| 13.745 | 19.1 | 348 | 6.43735 |
| 14.301 | 11.6 | 211 | 6.18834 |
| 14.628 | 10.9 | 199 | 6.05082 |
| 16.715 | 22.9 | 417 | 5.29968 |
| 17.03 | 13.4 | 243 | 5.20246 |
| 17.24 | 10.8 | 197 | 5.13943 |
| 17.718 | 6.2 | 113 | 5.00178 |
| 18.325 | 14.6 | 266 | 4.83759 |
| 19.063 | 58 | 1056 | 4.65174 |
| 19.935 | 41 | 747 | 4.45027 |
| 20.61 | 8.6 | 156 | 4.3061 |
| 21.103 | 10.2 | 186 | 4.20649 |
| 21.965 | 40.9 | 744 | 4.04338 |
| 22.358 | 14.7 | 268 | 3.97314 |
| 23.195 | 11.9 | 217 | 3.83173 |
| 23.453 | 12 | 218 | 3.79007 |
| 24.203 | 12.6 | 230 | 3.6743 |
| 24.743 | 9.4 | 171 | 3.59539 |
| 25.126 | 15 | 273 | 3.54145 |
| 25.674 | 22.6 | 411 | 3.46698 |
| 26.823 | 21.4 | 389 | 3.32111 |
| 27.534 | 11.5 | 210 | 3.23696 |
| 27.964 | 11 | 200 | 3.18813 |
| 28.511 | 7.4 | 135 | 3.12812 |
| 28.938 | 7.7 | 140 | 3.08299 |
| 30.927 | 10.5 | 192 | 2.88905 |
| 31.606 | 6.4 | 116 | 2.82855 |
| 32.618 | 5.8 | 105 | 2.74304 |
| 33.224 | 6.2 | 113 | 2.69439 |
| 34.487 | 6.6 | 121 | 2.59854 |
| 34.9 | 7.4 | 134 | 2.56872 |
| 35.613 | 5.5 | 101 | 2.51894 |
| 37.351 | 5.2 | 95 | 2.40564 |
| 39.166 | 6.7 | 122 | 2.29822 |
| 39.338 | 5.9 | 107 | 2.28857 |

Form IV was obtained by cooling crystallization in EA using Form I as a starting material or by anti-solvent precipitation in acetone/heptane at 50° C. using the amorphous Compound 1 as the starting material. Finally, Form IV was prepared in acetone-heptane.

Scale-up of Form IV: Amorphous Compound 1 (~100 mg) was dissolved in 0.2 mL of acetone at 50° C., then 0.4 mL of heptane was added. Solids appeared after stirring for 0.5 h at 50° C. The sample was collected by filtration after stirring for 1 h and characterized after dried at 50° C. under vacuum for 3 h. Form IV (~80 mg) was successfully prepared with a yield of 80%.

One melting peak with onset temperature of 273° C. and 0.33% weight loss before 200° C. (FIG. 4B) were observed by DSC and TGA, respectively. About 0.22% residual acetone was detected by NMR. Form IV should be an anhydrous form with residual solvent. DVS results (FIG. 4C) showed that Form IV was slightly hygroscopic with about 1.37% water uptake at 80% RH, and the crystal form remained unchanged after DVS testing.

Representative XRPD and DSC spectra of Form IV are shown in FIG. 4A-4B. A table of XRPD peaks are shown below in Table 4.

TABLE 4

XRPD peak table for form IV.

| Angle 2-Theta ° | Intensity % | Intensity Count | d value Angstrom | Angle 2-Theta ° | Intensity % | Intensity Count | d value Angstrom |
|---|---|---|---|---|---|---|---|
| 6.348 | 29.3 | 345 | 13.91278 | 23.16 | 24.4 | 288 | 3.8373 |
| 6.7 | 100 | 1179 | 13.18177 | 23.653 | 14 | 165 | 3.7585 |
| 8.641 | 45.1 | 532 | 10.22445 | 24.547 | 11.2 | 132 | 3.62364 |
| 10.858 | 18.2 | 215 | 8.1413 | 24.742 | 10.8 | 127 | 3.59543 |
| 11.401 | 11.7 | 138 | 7.75527 | 25.689 | 13.4 | 158 | 3.46501 |
| 12.415 | 18.2 | 214 | 7.12398 | 26.006 | 13.1 | 154 | 3.4235 |
| 12.821 | 11.1 | 131 | 6.899 | 26.638 | 6.3 | 74 | 3.34367 |
| 13.573 | 12.7 | 150 | 6.51862 | 27.365 | 10.1 | 119 | 3.25652 |
| 14.579 | 29.9 | 353 | 6.071 | 28.334 | 7.5 | 88 | 3.14731 |
| 14.842 | 33.2 | 391 | 5.96414 | 28.534 | 6.3 | 74 | 3.12573 |
| 15.71 | 20.4 | 240 | 5.6362 | 28.971 | 13.4 | 158 | 3.07957 |
| 16.235 | 10.4 | 123 | 5.45509 | 29.904 | 10.2 | 120 | 2.98555 |
| 16.612 | 53.5 | 631 | 5.33233 | 30.404 | 7.5 | 89 | 2.93759 |
| 17.636 | 33.7 | 397 | 5.02483 | 31.087 | 8.9 | 105 | 2.87455 |
| 18.937 | 37.3 | 440 | 4.68251 | 32.525 | 8.1 | 96 | 2.75071 |
| 19.165 | 36 | 425 | 4.62725 | 33.135 | 5.9 | 69 | 2.70147 |
| 20.35 | 18.7 | 221 | 4.3605 | 34.066 | 6.1 | 72 | 2.62971 |
| 20.792 | 28.2 | 333 | 4.26877 | 36.009 | 5.1 | 60 | 2.49216 |
| 21.211 | 22 | 259 | 4.18536 | 36.727 | 4.2 | 50 | 2.44503 |
| 22.79 | 11 | 130 | 3.89886 | 38.181 | 4.7 | 55 | 2.3552 |

Above all, four forms were obtained and characterized, as summarized in Table 5. Form I and IV were anhydrates. Two hydrates, Form II (mono-hydrate) and III (di-hydrate) were both not stable, and dehydration occurred at low temperature.

TABLE 5

Characterization Results of Different Forms

| Form | XRPD | DSC (Onset/Enthalpy) | TGA (wt %/Temp.) | Comment |
|---|---|---|---|---|
| N/A | Pattern 1 | N/A | N/A | Wet cake |
| Form I Anhydrate | Pattern 2 | 239° C., 60 J/g | 0.17%/200° C. | Sharp melting peak was only obtained by drying the sample prepared in IPA |
| Form II Mono-Hydrate | Pattern 3 | 111° C., 30 J/g 171° C., 6.5 J/g | 3.1%/RT-150° C. | 0.1% acetone, dehydration occurred at low temperature |
| Form III Di-Hydrate | Pattern 4 | 95° C., 77 J/g | 5.0%/RT-150° C. | Dehydration occurred at low temperature |
| Form IV Anhydrate | Pattern 5 | 273° C., >43 J/g (melting/decomp.) | 0.33%/RT-200° C. | Stable form, slightly hygroscopic, 0.2% residual acetone |

Example 4. Interconversion and Solubility Studies of Solid Forms of Compound 1

Interconversion Studies: Equal amounts (~7 mg) of Form I, II and III were mixed together and then suspended in 0.5 mL of different solvents at room temperature or 50° C., respectively. Residual solids were collected by filtration and characterized at appropriate time. Additionally, Form IV (~12 mg) was slurried in 0.5 ml, water or MeOH/water (1/4) at RT or 50° C. for 3 days. Residual solids were collected by filtration and analyzed by XRPD.

The results showed that the mixtures of Forms I, II, and III were converted to Form IV except in IPA and MeOH/water (1/4) at RT (Table 6). In IPA, the wet cake was still Pattern 1, which was likely an IPA solvate and Form II was obtained in the solvent systems containing water at RT. Hence, Form IV was the stable form in the solvent systems at high temperature and at RT without water.

TABLE 6

Interconversion Study

| Solvents | Temp. | Time paint (day) | XRPD of wet cake |
|---|---|---|---|
| IPA | RT | 3 | Pattern 1 |
| EA/MTBE (1/4) | | 3 | Form IV |
| MeOH/Water (1/4) | | 3 | Form II |
| IPA | 50° C. | 4 | Form IV |
| EA/MTBE (1/4) | | 3 | Form IV |
| MeOH/Water (1/4) | | 3 | Form IV |

Form IV was slurried in the solvent systems containing water to confirm whether it was the stable form in water or not. The results showed that Form IV remained unchanged after slurry in water or MeOH/water at RT and 50° C. for 3 days, and no hydrate was formed. Hence, Form IV was stable in aqueous systems without the seeds of hydrate for 3 days.

Solubility Studies: Solubility of Form IV was tested in three bio-relevant media (Simulated Gastric Fluid (SGF), Fasted State Simulated Intestinal Fluid (FaSSIF), and Fed State Simulated Intestinal Fluid (FeSSIF)) and water. Solubility of the amorphous Compound 1 was also tested in FaSSIF. Form IV (~10 mg) was weighed into 2 mL of four media to make suspensions respectively, and about 10 mg of the amorphous starting material was also added into 2 mL of FaSSIF. Then all suspensions were shaken at 37° C. with 200 rpm for up to 24 hours. At 0.5, 2 and 24 hours, about 0.7 mL of each suspension was filtered. The filtrate was analyzed by HPLC and pH meter, and the residual solids were also checked by XRPD at 24 hours.

As summarized in Table 7, Form IV had lower solubility in FaSSIF than the amorphous starting material, and the solubility decreased from 0.3 mg/mL to 0.02 mg/mL. In other media, Form IV also had low solubility, <0.07 mg/mL.

TABLE 7

Solubility Results

| Sample | Media | Solubility (mg/mL) | | | pH | | | XRPD-24 h |
| --- | --- | --- | --- | --- | --- | --- | --- | --- |
| | | 0.5 h | 2 h | 24 h | 0.5 h | 2 h | 24 h | |
| Form IV | SGF | 0.036 | 0.034 | 0.036 | 1.25 | 1.23 | 1.18 | unchanged |
| | FeSSIF | 0.037 | 0.037 | 0.062 | 4.99 | 4.95 | 4.96 | unchanged |
| | FaSSIF | 0.017 | 0.016 | 0.021 | 6.50 | 6.35 | 6.50 | unchanged |
| | Water | 0.014 | 0.011 | 0.009 | 7.01 | 6.86 | 7.23 | unchanged |
| Amorphous material | FaSSIF | 0.302 | 0.263 | 0.283 | 6.51 | 6.41 | 6.51 | unchanged |

Stability Studies: Appropriate amounts of Form IV were put at 40° C./75% RH, 60° C. and 25±2° C./92.5% RH conditions for 14 days. Then the sample was tested by HPLC and XRPD to determine the chemical and physical stability. The results are shown in Table 8.

TABLE 8

Stability Evaluation Results

| | Purity (Area %) | | |
| --- | --- | --- | --- |
| | Purity-initial (Area %) | 60° C. (7 D/14 D) | 40° C./75% RH (7 D/14 D) |
| Form IV | 98.30 | 97.98/97.88 | 98.21/98.12 |

After Form IV was stored at 60° C. for 2 weeks, a new impurity was detected, and it increased along with time. On the other hand, the purity of the starting material Form IV was only about 98.3%. For physical stability testing, XRPD remained unchanged under the test conditions for 14 days, Form IV was physically stable at 3 testing conditions during the testing period.

Form IV was also tested for mechanical stability. In this case, appropriate amount of Form IV was ground for 2 and 5 min, and then tested by XRPD to check the crystal form. The results show that no new form was generated, and the crystallinity decreased upon grinding.

Example 5. Preparation and Solid State Characterization of Compound 2

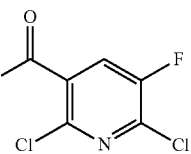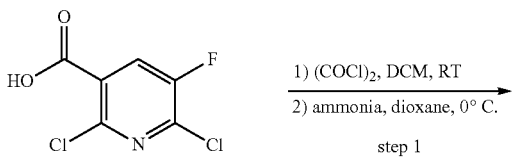

-continued

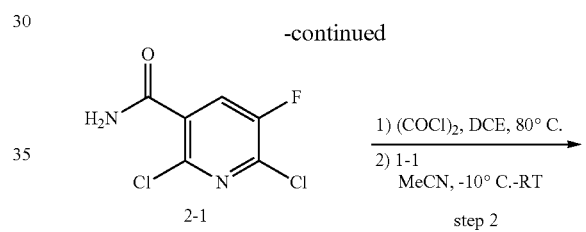

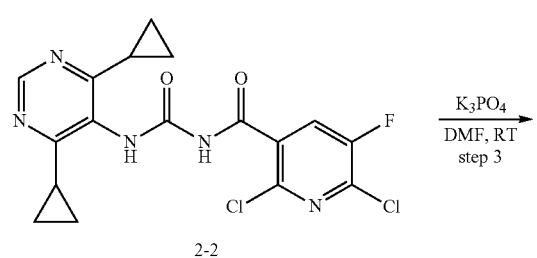

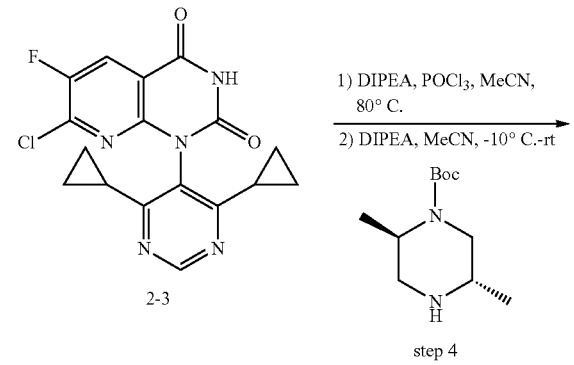

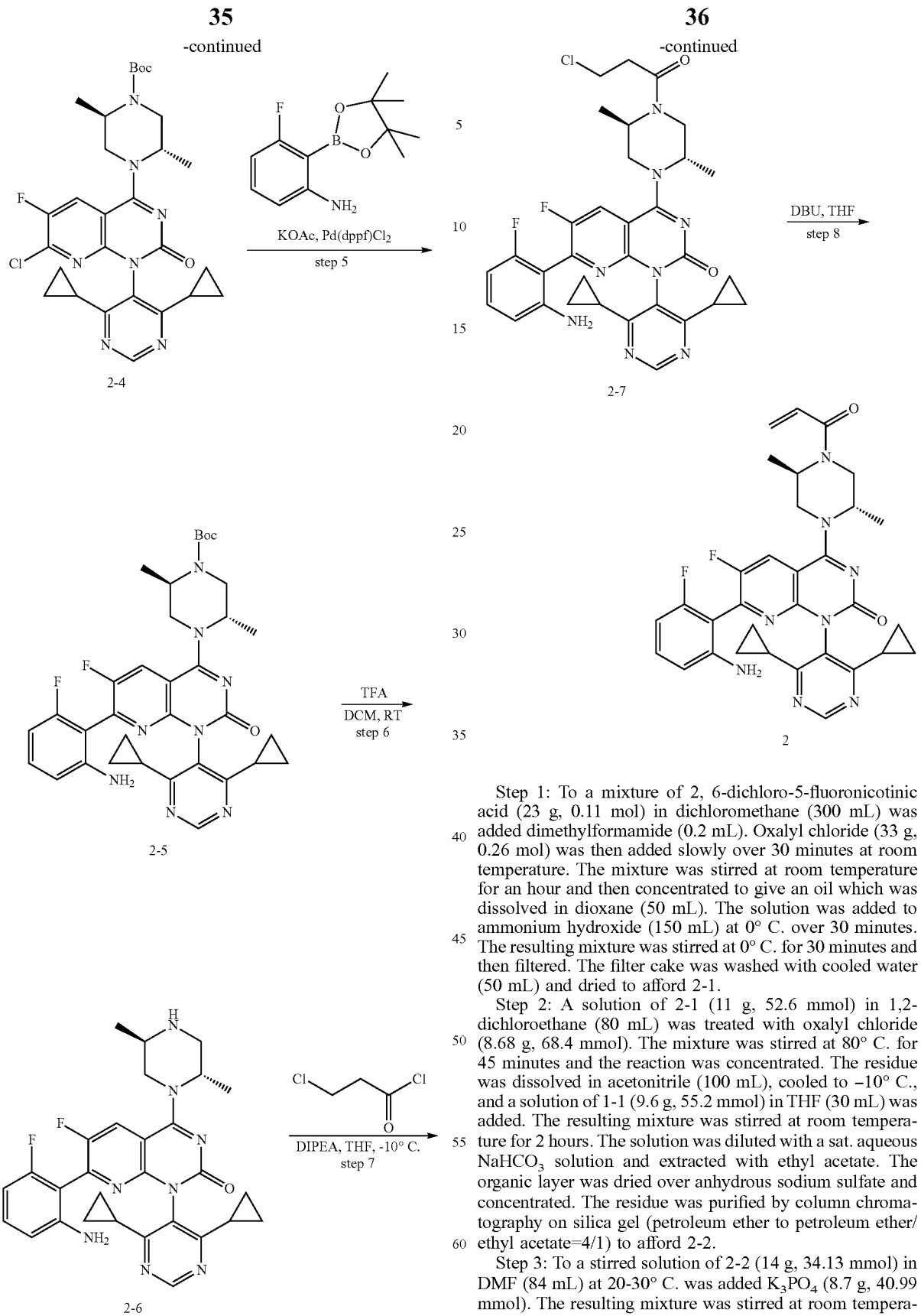

Step 1: To a mixture of 2, 6-dichloro-5-fluoronicotinic acid (23 g, 0.11 mol) in dichloromethane (300 mL) was added dimethylformamide (0.2 mL). Oxalyl chloride (33 g, 0.26 mol) was then added slowly over 30 minutes at room temperature. The mixture was stirred at room temperature for an hour and then concentrated to give an oil which was dissolved in dioxane (50 mL). The solution was added to ammonium hydroxide (150 mL) at 0° C. over 30 minutes. The resulting mixture was stirred at 0° C. for 30 minutes and then filtered. The filter cake was washed with cooled water (50 mL) and dried to afford 2-1.

Step 2: A solution of 2-1 (11 g, 52.6 mmol) in 1,2-dichloroethane (80 mL) was treated with oxalyl chloride (8.68 g, 68.4 mmol). The mixture was stirred at 80° C. for 45 minutes and the reaction was concentrated. The residue was dissolved in acetonitrile (100 mL), cooled to −10° C., and a solution of 1-1 (9.6 g, 55.2 mmol) in THF (30 mL) was added. The resulting mixture was stirred at room temperature for 2 hours. The solution was diluted with a sat. aqueous NaHCO₃ solution and extracted with ethyl acetate. The organic layer was dried over anhydrous sodium sulfate and concentrated. The residue was purified by column chromatography on silica gel (petroleum ether to petroleum ether/ethyl acetate=4/1) to afford 2-2.

Step 3: To a stirred solution of 2-2 (14 g, 34.13 mmol) in DMF (84 mL) at 20-30° C. was added K₃PO₄ (8.7 g, 40.99 mmol). The resulting mixture was stirred at room temperature for 16 hours. The reaction was quenched with HCl (1 N) and filtered. The solid was washed with water, and then slurried in MeCN. The mixture was filtered, and the filter cake was dried to afford 2-3.

Step 4: To a solution of 2-3 (16.6 g, 44.41 mmol) and DIEA (8.6 g, 66.54 mmol) in MeCN (83 mL) was added POCl$_3$ (8.2 g, 53.48 mmol) dropwise at room temperature. The resulting mixture was stirred at 80° C. for 45 minutes, followed by addition of DIEA (8.6 g, 66.54 mmol) and a solution of (2R,5S)-tert-butyl 2,5-dimethylpiperazine-1-carboxylate (9.5 g, 44.33 mmol) in MeCN (33 mL) dropwise at −10° C. After stirring at room temperature for 1 hour, the reaction was quenched with aqueous Na$_2$CO$_3$ solution and the mixture was filtered. The solid was slurried in water and then filtered. The solid was dried to afford 2-4.

Step 5: A mixture of 2-4 (50 g, 87.71 mmol), 3-fluoro-2-(4,4,5,5-tetramethyl-1,3,2-dioxaborolan-2-yl)aniline (25 g, 105.45 mmol), Pd(dppf)Cl$_2$ (1.3 g, 0.18 mmol), KOAc (17.2 g, 175.26 mmol) and water (1.6 g) in dioxane (500 mL) was stirred at 80° C. for 2 hours under nitrogen atmosphere. The mixture was cooled and filtered. The filtrated was added to water to precipitate, and then filtered. The solid was dissolved in DMC and was washed with aqueous Na$_2$CO$_3$ solution. The organic phase was performed solvent switch into toluene by distillation for several times. The mixture was heated in toluene at 80° C. and then cooled to 20° C. to crystallize. Filtered, and the filter cake was dried to afford 2-5.

Step 6: A mixture of 2-5 (10 g, 15.51 mmol) in DCM (50 mL) was treated with TFA (21.2 g), and the mixture was stirred at 25° C. for 3 hours. The reaction was quenched with an aqueous Na$_2$CO$_3$ solution and the mixture was separated. The organic layer was washed with water twice and then concentrated. The residue was dissolved in EtOH and a solution of fumaric acid in EtOH was added. The mixture was filtered and the solid was washed with EtOH. The solid was added to an aqueous Na$_2$CO$_3$ solution and the mixture was extracted with DCM. The organic layer was washed with water and then concentrated. The residue was performed a solvent switch in heptane by distillation for several times, and filtered. The filter cake was washed with heptane and dried to afford 2-6.

Step 7: To a mixture of 2-6 (10 g, 18.36 mmol) and DIPEA (2.6 g, 20.12 mmol) in THF (100 mL)) was added a solution of 3-chloropropionyl chloride (2.28 g, 17.96 mmol) in THF (100 mL) at −10° C. The mixture was stirred for 1 hour and quenched with an aqueous citric acid solution. The mixture was extracted with EtOAc, and the organic layer was washed with water. The organic layer was performed a solvent switch in heptane by distillation for several times, and filtered. The filter cake was washed with heptane and dried to afford 2-7.

Step 8: A mixture of 2-7 (10 g, 15.75 mmol) and DBU (4.79 g, 31.26 mmol) in THF (70 mL) and DMSO (30 mL) was stirred at 20° C. for 1 hour. EtOAc and an aqueous citric acid solution were added. The mixture was separated and the organic layer was water. The organic layer was performed a solvent switch in isopropanol by distillation for several times, and filtered. The filter cake was washed with water and dried to afford 2. LCMS (ESI, m/z): [M+H]$^+$=599.1; HNMR (400 MHz, methanol-d$_4$, ppm): δ 8.73 (s, 1H), 8.26-8.22 (m, 1H), 7.15-7.09 (m, 1H), 6.84-6.74 (m, 1H), 6.53 (d, J=8.4 Hz, 1H), 6.42-6.38 (m, 1H), 6.30-6.24 (m, 1H), 5.83-5.78 (m, 1H), 5.01 (brs, 1H), 4.91-4.83 (m, 1H), 4.53-4.29 (m, 2H), 3.96-3.89 (m, 1.5H), 3.54-3.50 (m, 0.5H), 1.82-1.75 (m, 1H), 1.73-1.66 (m, 1H), 1.47 (d, J=6.8 Hz, 3H), 1.37-1.27 (m, 3H), 1.16-1.05 (m, 4H), 1.03-0.97 (m, 2H), 0.88-0.83 (m, 2H). FNMR (376 MHz, methanol-d$_4$, ppm): δ −114.9 (1F), −125.6 (1F).

Compound 2 prepared via the above procedure was slurried in EtOAc, and filtered to provide Compound 2 in a crystalline form A. About 1.1% of residual EtOAc was detected by $^1$H-NMR, corresponding to weight loss at 120-290° C. in TGA (FIG. 5B). Two overlapped endothermic peaks were observed by DSC (FIG. 5B). Compound 2 in Form A was heated to 250° C. and DSC profile of the residual solid was unchanged, suggesting the overlapped peak was due to melting with crystal form transformation. Thus, the starting material was an anhydrate.

Form A was very soluble in DCM (>92 mg/mL) and soluble (20-33 mg/mL) in MeOH, butanone, THF, ACN and acetone. In other solvents, Form A was practically insoluble.

Representative XRPD and DSC spectra of Form A are shown in FIG. 5A-5B. A table of XRPD peaks are shown below in Table 9.

TABLE 9

XRPD peak table for Form A

| Angle 2-Theta ° | Intensity % | Intensity Count | d value Angstrom |
|---|---|---|---|
| 6.236 | 100 | 1978 | 14.1623 |
| 7.951 | 11.7 | 232 | 11.1101 |
| 10.241 | 7.2 | 143 | 8.63058 |
| 11.636 | 6.6 | 130 | 7.59894 |
| 12.226 | 16.3 | 322 | 7.2337 |
| 12.614 | 30.8 | 610 | 7.01205 |
| 13.759 | 20.8 | 411 | 6.4308 |
| 14.761 | 31.9 | 631 | 5.99658 |
| 15.128 | 19.6 | 387 | 5.85189 |
| 17.74 | 17.6 | 348 | 4.99561 |
| 18.033 | 20.5 | 406 | 4.91521 |
| 18.975 | 7.8 | 155 | 4.67329 |
| 19.646 | 22.8 | 450 | 4.51518 |
| 19.882 | 42.7 | 844 | 4.46203 |
| 20.612 | 7.6 | 150 | 4.30569 |
| 21.24 | 16.7 | 331 | 4.17978 |
| 21.913 | 7.9 | 156 | 4.05285 |
| 22.558 | 7.2 | 143 | 3.93849 |
| 23.06 | 15.4 | 305 | 3.85385 |
| 23.428 | 8.9 | 177 | 3.79407 |
| 24.589 | 11.7 | 231 | 3.61753 |
| 25.36 | 10.5 | 207 | 3.50922 |
| 26.39 | 10.1 | 200 | 3.37458 |
| 27.447 | 7.2 | 143 | 3.24701 |
| 29.958 | 4.9 | 96 | 2.98033 |
| 30.666 | 5.8 | 114 | 2.91305 |
| 31.233 | 4.2 | 84 | 2.86149 |
| 31.999 | 4.7 | 92 | 2.79467 |
| 33.19 | 5.1 | 100 | 2.69706 |

Example 6. Polymorph Screening of Compound 2

This example screens polymorphs of Compound 2. Following similar procedures as shown in Example 3, polymorph screening was conducted using Form A of Compound 2 as starting point with commonly used solvents and solvent mixtures by slurry, cooling, evaporative crystallization, anti-solvent precipitation and mechanical treatment method.

Slurry in single solvent: 15 to 20 mg of Compound 2 in Form A was added into different solvents (MeOH, EtOH, IPA (isopropyl alcohol), IBA (isobutyl alcohol), MEK (methyl ethyl ketone or 2-butanone), THF (tetrahydrofuran), ACN (acetonitrile), MTBE (methyl tert-Butyl ether), Acetone, Water, Toluene, EA (ethyl acetate), or IPAC (isopropyl acetate)) to make suspension with a concentration of 15 to 100 mg/mL. The suspensions were kept stirring at 50° C. for 1 day or at RT for 3 days, respectively. Solid samples were collected by filtration and analyzed by XRPD. If new XRPD patterns were identified, the sample was dried under vacuum at 50° C. for overnight, and further analyzed by DSC and TGA.

Five new patterns were identified by XRPD and assigned as Pattern 2, 3, 4, 5 and 6, and Pattern 2 was obtained from most of solvents. Wet cake obtained in EtOH through slurry at 50° C. for 1 day was identified as Pattern 3, which was converted to Pattern 4 after drying. Wet cake obtained in IPA through slurry at RT or 50° C. was identified as Pattern 5, which was converted to Pattern 6 after drying.

Slurry in Mixed Solvent (Organic Solvent/Water) at RT and 50° C.: About 20 mg of Compound 2 in Form A was added into 1 mL of mixed solvents of MeOH/$H_2O$ (1/9) and ACN/$H_2O$ (1/9), respectively, to make suspension with a concentration of 20 mg/mL. The suspensions were kept stirring at 50° C. or RT, respectively. Solid samples were collected by filtration and analyzed by XRPD. If new XRPD patterns were identified, the sample was dried under vacuum at 50° C. overnight, and further analyzed by DSC and TGA. Pattern 1 (Form A) was obtained in all experiments and no new pattern was obtained.

Evaporative Crystallization in binary solvents: 13 saturated drug solutions in MeOH, EtOH, IPA (isopropyl alcohol), IBA (isobutyl alcohol), MEK (methyl ethyl ketone or 2-butanone), THF (tetrahydrofuran), ACN (acetonitrile), MTBE (methyl tert-Butyl ether), Acetone, Water, Toluene, EA (ethyl acetate), or IPAC (isopropyl acetate) (filtrates) were distributed in 96-well plates. Each well contained two different filtrates and the volume of each filtrate was 100 μL. The plate was covered by sealing film with pin holes and allowed to evaporate in an operating laboratory fume hood under ambient conditions. All solids with sufficient quantities were analyzed by XRPD.

Three new patterns were identified and assigned as Pattern 7, 9 and Pattern 10, respectively. Pattern 7 was obtained from evaporation in EtOH and similar as that of Pattern 4. Pattern 9 was obtained from 96-well plate in IPA/2-butanone, IPA/THF, IPA/acetone and isobutanol/THF. Pattern 10 was obtained from evaporation in acetone/iPrOAc and converted into Pattern 2 (Form B) after drying. Other samples obtained in %-well plate were glassy.

Evaporative Crystallization in single solvent: About 0.5 mL of the 13 saturated drug solutions in MeOH, EtOH, IPA (isopropyl alcohol), IBA (isobutyl alcohol), MEK (methyl ethyl ketone or 2-butanone), THF (tetrahydrofuran), ACN (acetonitrile), MTBE (methyl tert-Butyl ether), Acetone, Water: Toluene, EA (ethyl acetate), or IPAC (isopropyl acetate) (filtrates) were evaporated with opening the lid in an operating laboratory fume hood under ambient conditions. All solids with sufficient quantity were analyzed by XRPD.

Cooling Crystallization: 15 to 20 mg of Compound 2 in Form A was added into vials. Different solvents (MeOH, THF, Acetone, ACN, 2-Butanone, Ethyl Acetate, or EtOH) were added at 50° C. with stirring, 100 to 500 μL per time, until the solution was clear. After filtration at 50° C., the filtrates were cooled down to RT or 5° C. Solid samples were collected by filtration and analyzed by XRPD. Pattern 2 and Pattern 6 were found from experiments performed in MeOH and EtOH, respectively.

Antisolvent precipitation: Based on estimated solubility results, anti-solvent precipitation was performed at RT using six selected good solvents (Acetone, MeOH, THF, ACN, 2-Butanone, and DCM) and five anti-solvents (toluene, iPrOAc, MEBE, water, and n-heptane). Saturated drug solutions were prepared in good solvents. Subsequently, anti-solvents were added gradually until turbid or 15V at RT. Pattern 1 (Form A) was generated from most of the precipitation experiments expect in MeOH/MTBE, MeOH/water and 2-butanone/water, in which Pattern 2 (Form B) was obtained. A new pattern was identified from acetone/water and THF/water. It was assigned as Pattern 8 and converted to Pattern 1 (Form A) after drying.

Total 10 XRPD patterns were found. All XRPD patterns are similar with a main peak about 6 degree 2-theta, except Pattern 9 that showed peak shift. It is interesting that the crystalline samples showed very similar XRPD patterns, suggesting they have isomorphic structures. Based on the characterization data, three anhydrous forms including the initial form were identified and assigned as Form A (Pattern 1), B (Pattern 2) and Form C (Pattern 6); a solvate was also found and assigned as Form D (Pattern 9). Other patterns were not pure phase or unstable without form assignment.

Form B (Pattern 2) obtained from slurry in MeOH (about 100 mg/mL) at 50° C. was used to characterize. No weight loss at 60-280° C. was observed by TGA, and the melting endothermic peak was at 289-290° C. with enthalpy of 95 J/g by DSC (FIG. 6B). The sample was an anhydrate, and assigned as Form B.

Form B which was the most stable form, was small scaled up for DVS analysis, solubility and stability studies. 103.02 mg of Compound 2 in Form A was dissolved in 5 mL of MeOH (48V) at RT. After filtration, 10 mL of water was added into the filtrate. Precipitation occurred quickly. The suspension was kept stirring at RT for about 2 hours. Solid samples were collected by filtration, dried under vacuum at 50° C. overnight. 94.16 mg solid was obtained with a yield of 91%.

Form B was slightly hygroscopic and absorbed ~0.84% water at 0-80% RH (FIG. 6C) without changing of crystal form after DVS testing (FIG. 6D).

Representative XRPD and DSC spectra of Form B are shown in FIG. 6A-6B. A table of XRPD peaks are shown below in Table 10.

TABLE 10

XRPD peak table for Form B.

| Angle 2-Theta ° | Intensity % | Intensity Count | d value Angstrom |
|---|---|---|---|
| 5.69 | 8.2 | 382 | 15.5188 |
| 6.249 | 100 | 4660 | 14.1315 |
| 7.983 | 6.4 | 300 | 11.0664 |
| 10.224 | 3.4 | 159 | 8.64514 |
| 10.562 | 2.3 | 107 | 8.36905 |
| 11.622 | 3.3 | 152 | 7.60784 |
| 11.861 | 3.8 | 176 | 7.45548 |
| 12.213 | 6.9 | 320 | 7.24107 |
| 12.617 | 87.7 | 4086 | 7.01017 |
| 13.639 | 11.9 | 556 | 6.48694 |
| 13.832 | 7.8 | 362 | 6.39688 |
| 14.472 | 11.1 | 516 | 6.11544 |
| 14.799 | 24 | 1118 | 5.98135 |
| 15.19 | 8.6 | 400 | 5.82825 |
| 15.599 | 3.8 | 177 | 5.67608 |
| 16.236 | 2.3 | 107 | 5.45499 |
| 17.501 | 6 | 281 | 5.06339 |
| 17.76 | 10.6 | 492 | 4.99 |
| 18.044 | 7.7 | 357 | 4.91227 |
| 18.614 | 3.9 | 181 | 4.76309 |
| 18.992 | 22.8 | 1063 | 4.66909 |
| 19.627 | 7.8 | 362 | 4.5195 |
| 19.863 | 19.8 | 923 | 4.46617 |
| 20.222 | 8.2 | 382 | 4.38775 |
| 20.597 | 5.9 | 276 | 4.30877 |
| 21.243 | 7 | 327 | 4.17919 |
| 21.403 | 10.1 | 470 | 4.14823 |
| 22.043 | 3.9 | 184 | 4.02928 |
| 22.514 | 6.3 | 292 | 3.94595 |
| 22.978 | 7.6 | 353 | 3.86739 |
| 23.13 | 7 | 324 | 3.84236 |
| 23.61 | 4.8 | 226 | 3.76525 |

TABLE 10-continued

XRPD peak table for Form B.

| Angle 2-Theta ° | Intensity % | Intensity Count | d value Angstrom |
|---|---|---|---|
| 24.37 | 5.8 | 271 | 3.64959 |
| 24.614 | 5.5 | 257 | 3.61396 |
| 25.42 | 9.8 | 456 | 3.50109 |
| 26.333 | 10.7 | 500 | 3.38178 |
| 26.674 | 7.9 | 369 | 3.33928 |
| 27.314 | 9 | 419 | 3.26247 |
| 28.271 | 2.9 | 135 | 3.15423 |
| 28.895 | 2.8 | 130 | 3.08743 |
| 29.943 | 3.4 | 159 | 2.98172 |
| 31.175 | 2.9 | 135 | 2.86664 |
| 31.948 | 16.6 | 772 | 2.79904 |
| 32.323 | 3.3 | 152 | 2.7674 |
| 33.731 | 2.3 | 109 | 2.65502 |
| 35.027 | 2.3 | 107 | 2.55972 |
| 35.958 | 2.8 | 131 | 2.49556 |
| 36.25 | 2.4 | 112 | 2.47612 |
| 37.268 | 2.2 | 103 | 2.41081 |
| 38.577 | 5.2 | 241 | 2.33197 |

Pattern 3 was identified from slurry experiment in EtOH at 50° C. After drying under vacuum at 50° C. for overnight, it converted to Pattern 4 and finally converted to Form B (Pattern 2) after desolvation or dehydration.

Pattern 4 was a plate shaped crystalline. 1.76% of weight loss at 110-240° C. was observed by TGA, corresponding to the small broad endothermic peak observed by DSC, due to desolvation or dehydration. After desolvation, it converted to Form B with a melting peak at 288-290° C. with enthalpy of 85 J/g. Pattern 4 might be a solvate or hydrate, but after comparing with pattern 6, it was found to be a mixture of pattern 6 and another pattern.

Pattern 5 was obtained from slurry experiment in IPA at 50° C. After drying under vacuum at 50° C. overnight, it converted to Pattern 6 and finally converted to Form B during heating.

Form C (Pattern 6): 0.9% of weight loss at 112-232° C. was observed by TGA, which might be due to loss of solvent. One exothermic peak at 206-221° C. followed by a melting peak at 288.7-289.4° C. was observed in DSC (FIG. 7B), suggesting potential crystal transformation during heating. Pattern 6 might be an anhydrate, and assigned as Form C (FIG. 7A). XRPD patterns of Form C and Pattern 4 were similar, but the extra peak of Pattern 4 was observed by XRPD, suggesting Pattern 4 was a mixture of Form C and solvate or hydrate.

Representative XRPD and DSC spectra of Form C are shown in FIG. 7A-7B. A table of XRPD peaks are shown below in Table 11.

TABLE 11

XRPD peak table for Form C.

| Angle 2-Theta ° | Intensity % | Intensity Count | d value Angstrom |
|---|---|---|---|
| 3.591 | 6.1 | 475 | 24.5858 |
| 6.187 | 100 | 7738 | 14.2735 |
| 6.772 | 4.7 | 361 | 13.0416 |
| 7.289 | 4.1 | 315 | 12.119 |
| 11.568 | 2.3 | 179 | 7.64371 |
| 12.257 | 6.7 | 515 | 7.21543 |
| 12.519 | 12.8 | 988 | 7.06516 |
| 14.244 | 7.7 | 599 | 6.21289 |
| 14.723 | 5.4 | 414 | 6.01178 |
| 15.68 | 6 | 463 | 5.64701 |

TABLE 11-continued

XRPD peak table for Form C.

| Angle 2-Theta ° | Intensity % | Intensity Count | d value Angstrom |
|---|---|---|---|
| 16.288 | 5.2 | 401 | 5.43757 |
| 16.675 | 2.6 | 198 | 5.31235 |
| 17.708 | 3.7 | 286 | 5.00466 |
| 18.877 | 4.1 | 320 | 4.69718 |
| 19.925 | 9.7 | 749 | 4.45258 |
| 20.76 | 3.9 | 299 | 4.27534 |
| 21.201 | 4.3 | 330 | 4.18737 |
| 22.147 | 3 | 235 | 4.0106 |
| 22.889 | 5.4 | 420 | 3.88217 |
| 23.309 | 4.5 | 345 | 3.81323 |
| 24.649 | 3.8 | 292 | 3.6088 |
| 25.347 | 4.9 | 382 | 3.51103 |
| 26.112 | 9.9 | 767 | 3.40991 |
| 26.826 | 3.3 | 256 | 3.32073 |
| 29.835 | 2.7 | 212 | 2.99226 |
| 30.101 | 2.4 | 186 | 2.96647 |
| 31.901 | 2.6 | 202 | 2.80307 |
| 33.126 | 2.1 | 163 | 2.70213 |
| 38.787 | 1.7 | 132 | 2.31981 |
| 39.494 | 1.6 | 120 | 2.27987 |

Pattern 7 was obtained from evaporation in EtOH and similar with Pattern 4. After heating to 250° C. by DSC, it converted to Form B (Pattern 2). About 1.3% of residual EtOH was detected by $^1$H-NMR, corresponding to weight loss at 102-210° C. in TGA. Two endothermic peaks due to desolvation and melting were observed by DSC. Pattern 7 might be a mixed form, similar as Pattern 4.

Pattern 8 was obtained from anti-solvent precipitation in acetone and water. After drying under vacuum at 50° C. for overnight, it converted to Form A. Pattern 8 might be a mixed form of Form A and unstable solvate. No further analysis was performed.

Form D (Pattern 9) was obtained from evaporation in 96-well plate in IPA/2-butanone, IPA/THF, IPA/acetone and isobutanol/THF. After drying under vacuum at 50° C. overnight, the crystal form was unchanged with decreasing of crystallinity. After heating to 250° C. by DSC, it converted to Form B. About 4% of weight loss at 107-223° C. was observed in TGA (FIG. 8B). 4.8% (~0.5 mol) of solvent was observed by NMR, suggesting the weight loss in TGA might be due to loss of solvent. Two endothermic peaks due to desolvation and melting were observed by DSC (FIG. 8B). Pattern 9 was a solvate, assigned as Form D.

Representative XRPD and DSC spectra of Form D are shown in FIG. 8A-8B. A table of XRPD peaks are shown below in Table 12.

TABLE 12

XRPD peak table for Form D.

| Angle 2-Theta ° | Intensity % | Intensity Count | d value Angstrom |
|---|---|---|---|
| 5.032 | 4.7 | 516 | 17.5474 |
| 5.558 | 100 | 10928 | 15.8867 |
| 7.942 | 2.2 | 242 | 11.1231 |
| 11.231 | 73.9 | 8080 | 7.87211 |
| 12.452 | 3 | 329 | 7.10297 |
| 14.881 | 4.9 | 536 | 5.94847 |
| 15.762 | 15.8 | 1731 | 5.6179 |
| 16.099 | 9.9 | 1079 | 5.50089 |
| 16.912 | 55.1 | 6021 | 5.2383 |
| 17.791 | 4 | 442 | 4.98141 |
| 18.518 | 7.6 | 830 | 4.7875 |
| 18.84 | 1.7 | 183 | 4.70629 |

TABLE 12-continued

XRPD peak table for Form D.

| Angle 2-Theta ° | Intensity % | Intensity Count | d value Angstrom |
|---|---|---|---|
| 19.39 | 3.1 | 334 | 4.57419 |
| 20.176 | 1.3 | 146 | 4.39776 |
| 20.959 | 3 | 329 | 4.23511 |
| 21.376 | 14.3 | 1560 | 4.15346 |
| 22.646 | 33.6 | 3676 | 3.92325 |
| 23.14 | 2.7 | 295 | 3.84059 |
| 23.524 | 4.1 | 448 | 3.77881 |
| 24.266 | 2.5 | 270 | 3.66495 |
| 24.702 | 3.8 | 419 | 3.60126 |
| 25.035 | 2.4 | 259 | 3.55403 |
| 25.714 | 2.1 | 229 | 3.46169 |
| 26.433 | 14 | 1525 | 3.36924 |
| 26.886 | 5.3 | 579 | 3.31348 |
| 27.64 | 1.2 | 136 | 3.22475 |
| 28.033 | 1.3 | 144 | 3.18043 |
| 28.444 | 8.5 | 933 | 3.13536 |
| 29.352 | 2 | 214 | 3.04046 |
| 30.117 | 1.8 | 200 | 2.96489 |
| 30.48 | 1.2 | 136 | 2.93039 |
| 32.107 | 1.1 | 122 | 2.78552 |
| 32.69 | 2.8 | 311 | 2.73716 |
| 33.399 | 1.7 | 183 | 2.68068 |
| 34.04 | 2.5 | 278 | 2.63166 |
| 34.3 | 36.5 | 3989 | 2.61228 |
| 34.841 | 1.3 | 143 | 2.57297 |
| 35.724 | 0.9 | 98 | 2.51136 |
| 37.854 | 1.6 | 177 | 2.37478 |
| 38.311 | 1.2 | 133 | 2.34755 |
| 39.318 | 1.2 | 136 | 2.28969 |
| 39.633 | 1.7 | 188 | 2.27223 |

Pattern 10 was obtained from evaporation in 96-well plate in Acetone/iPrOAc an Acetone/water. After drying under vacuum at 50° C. for overnight, it converted to Form B. Pattern 10 was an unstable form and no further analysis was performed.

Total ten XPRD patterns were identified, including three anhydrates, a solvate, two mixed forms and four unstable patterns. The XRPD patterns of Form A and B are very similar, and obviously different from Form C with the characteristic peaks at 7.3°, 14.2°, 15.7°, 16.3°, 20.8° and 26.1° 2θ. The characteristic peaks of Form B different from Form A are mainly located at 14.5°, 15.6°, 17.5°, 20.2°, 31.9° and 38.6° 2θ. Table 13 summarizes the anhydrous forms of Compound 2.

TABLE 13

Anhydrous Forms Summary of Compound 2

| Form Solvation | XRPD Pattern | DSC Onset (° C.), ΔH (J/g) | TGA wt loss %/@T (° C.) |
|---|---|---|---|
| A Anhydrate | 1 | 286, 89, double peak | 1.3/120-290 |
| B Anhydrate | 2 | 289, 95 | 0.0015/60-283 |
| C Anhydrate | 6 | 208, 6, exo 289, 87 | 0.9/112-232 |

Example 7. Interconversion and Solubility Studies of Solid Forms of Compound 2

Interconversion Studies: Competitive slurry of Form A, Form B and Form C was performed in acetone and acetone/water (1/4) at RT or 50° C., with details shown below.

| Solvent | Mass (mg) Farm A + Form B + Form C | Volume (mL) | Temp. |
|---|---|---|---|
| Acetone | 9.9 + 9.9 + 10.5 | 0.5 | RT |
| Acetone | 9.8 + 9.5 + 9.6 | 0.3 | 50° C. |
| Acetone/H$_2$O (1/4) | 10.0 + 9.4 + 9.9 | 0.5 | RT |
| Acetone/H$_2$O (1/4) | 10.1 + 10.1 + 10.4 | 0.3 | 50° C. |

Competitive slurry of Form A, Form B and Form C in acetone and acetone/water (1/4). The mixtures of different forms completely converted to Form B in non-aqueous solvent after 1 day and showed tendency to convert to Form B in solvent-aqueous solution after 7 days, peaks at 14.5° and 17.5° 2θ increased gradually. DSC of the remaining solids showed endothermic peak of Form A became very weak, suggesting the mixture has tendency to convert to Form B. The results indicated that Form B was the more stable form than Form A and C.

Solubility in Bio-relevant Media: Form A and Form B was added into SGF, FeSSIF, FaSSIF and water, respectively. The suspensions were kept shaking at 37° C. with 200 rpm for 24 hours. At 0.5 h, 2 h and 24 h, suspensions were filtered and drug concentrations of filtrates were analyzed by HPLC. pH of filtrates was measured at each time point. The remaining solids at 24 hours were characterized by XRPD.

Both forms showed pH dependency solubility profile, solubility was slightly high at low pH. Solubility of Form A in SGF was higher than Form B at 24 hours. In other media, solubility of these two forms was similar. XRPD patterns of remaining solids at 24 hours were unchanged. The results are shown in Table 14.

TABLE 14

Solubility Results of Form A (Pattern 1) and Form B (Pattern 2) in Bio-relevant Media

| Sample | Time (h) | Water | | SGF (pH 1.2) | | FaSSIF (pH 6.5) | | FeSSiF (pH 5.0) | |
|---|---|---|---|---|---|---|---|---|---|
| | | Solubility (mg/mL) | pH | Solubility (mg/mL) | pH | Solubility (mg/mL) | pH | Solubility (mg/mL) | pH |
| Form A | 0.5 h | 0.015 | 6.18 | 0.067 | 1.19 | 0.019 | 6.35 | 0.041 | 4.84 |
| | 2 h | 0.025 | 6.43 | 0.072 | 1.13 | 0.029 | 6.34 | 0.045 | 4.87 |
| | 24 h | 0.043 | 6.60 | 0.17 | 1.11 | 0.024 | 6.28 | 0.042 | 4.82 |
| Form B | 0.5 h | 0.021 | 5.93 | 0.060 | 1.15 | 0.016 | 6.29 | 0.044 | 4.82 |
| | 2 h | 0.020 | 6.77 | 0.058 | 1.09 | 0.051 | 6.37 | 0.043 | 4.90 |
| | 24 h | 0.019 | 6.78 | 0.056 | 1.14 | 0.018 | 6.26 | 0.037 | 4.83 |

Solid State Stability of Form B: About 10 mg of Form B was open placed at 40° C./75% RH and 60° C. for 7 days and at 25° C./92.5% RH for 10 days, respectively. Prepare samples in duplicate (n=2) per condition. The solids were analyzed by XRPD and HPLC (only for 40° C./75% RH and 60° C.).

Solid stability was conducted at 40° C./75% RH and 60° C. for 7 days and at 25° C./92.5% RH for 10 days, respectively. The results were summarized in Table 15. Form B was physically stable at test conditions; crystal form was unchanged. Form B was chemically stable at 40° C./75% RH for 7 days, however, slight degradation was observed at 60° C. for 7 days, purity decreased by 0.16% and two new impurities (RRT 0.86 and RRT 0.93) were detected.

TABLE 15

Stability Evaluation Results

| Initial | Purity-7 d | | XRPD | | |
|---|---|---|---|---|---|
| Purity | (Area %) | | 40° C./75% RH | 60° C. | 25° C./92.5% RH |
| (Area %) | 40° C./75% RH | 60° C. | After 7 d | After 7 d | After 10 d |
| 98.98 | 98.97 | 98.82 | Unchanged | Unchanged | Unchanged |

About 10-20 mg of Compound 2 in Form A and Form B were ground manually for 5 min, respectively. Form A was unchanged after grinding, while crystallinity of Form B became weak. DSC of Form B after grinding for 5 min suggesting Form A appeared after grinding, suggesting potential crystal form change during mechanical treatment.

In summary, solubility of both Form A and Form B showed pH dependence. The highest solubility of Form B was in SGF, 0.056 mg/mL, and the lowest was in FaSSIF, 0.018 mg/mL. Solubility of Form A was slightly higher in SGF than Form B, and similar in other media. Solid state stability results indicated that Form B was both physically and chemically stable at 40° C./75% RH for 7 days, and the crystal form remained unchanged 92.5% RH for 10 days and 60° C. for 7 days.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

With respect to aspects of the invention described as a genus, all individual species are individually considered separate aspects of the invention. If aspects of the invention are described as "comprising" a feature, embodiments also are contemplated "consisting of" or "consisting essentially of" the feature.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference. To the extent that any meaning or definition of a term in this document conflicts with any meaning or definition of the same term in a document incorporated by reference, the meaning or definition assigned to that term in this document shall govern.

What is claimed is:

1. A crystalline form of a compound having the following formula:

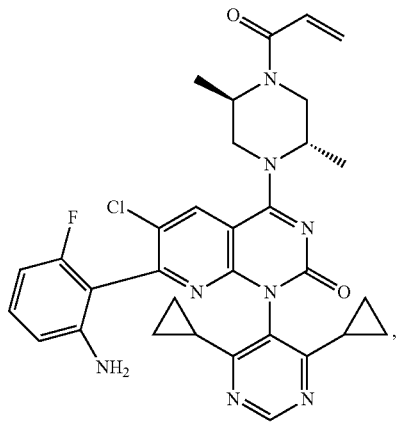 [SMILES: C=CC(=O)N1C[C@H](C)N(c2nc(=O)n(-c3c(C4CC4)ncnc3C3CC3)c3nc(-c4c(N)cccc4F)c(Cl)cc23)C[C@H]1C]

wherein the crystalline form is Form I, Form II, Form III, or Form IV, wherein crystalline Form I is characterized by an X-ray powder diffraction (XRPD) pattern having one or more of the following peaks: 6.9, 11.4, 11.5, 13.0, 14.8, 17.4, 17.8, 18.1, 19.4, and 22.8 degrees 2 theta, ±0.2°; Form II is characterized by an X-ray powder diffraction (XRPD) pattern having one or more of the following peaks: 8.1, 15.6, and 18.8 degrees 2 theta, ±0.2°; Form III is characterized by an X-ray powder diffraction (XRPD) pattern having one or more of the following peaks: 6.6, 8.3, 11.5, 19.1, 19.9, and 22.0 degrees 2 theta, ±0.2°; and Form IV is characterized by an X-ray powder diffraction (XRPD) pattern having one or more of the following peaks: 6.7, 8.6, 16.6, 18.9, and 19.2 degrees 2 theta, ±0.2°.

2. The crystalline form of claim 1, which is crystalline Form I, characterized by an X-ray powder diffraction (XRPD) pattern having the following peaks: 6.9, 11.4, 11.5, 13.0, 14.8, 17.4, 17.8, 18.1, 19.4, and 22.8 degrees 2 theta, ±0.2°.

3. The crystalline form of claim 1, which is crystalline Form II, characterized by an X-ray powder diffraction (XRPD) pattern having the following peaks: 8.1, 15.6, and 18.8 degrees 2 theta, ±0.2°.

4. The crystalline form of claim 1, which is crystalline Form III, characterized by an X-ray powder diffraction (XRPD) pattern having the following peaks: 6.6, 8.3, 11.5, 19.1, 19.9, and 22.0 degrees 2 theta, ±0.2°.

5. The crystalline form of claim 1, which is crystalline Form IV, characterized by an X-ray powder diffraction (XRPD) pattern having the following peaks: 6.7, 8.6, 16.6, 18.9, and 19.2 degrees 2 theta, ±0.2°.

6. The crystalline form of claim 1, which is substantially pure.

7. A pharmaceutical composition comprising the crystalline form of claim 1, and optionally a pharmaceutically acceptable excipient.

8. A pharmaceutical composition comprising the crystalline form of claim 5, wherein the pharmaceutical composition is free or substantially free of the compound in a solid form other than Form IV.

9. A crystalline form of a compound having the following formula:

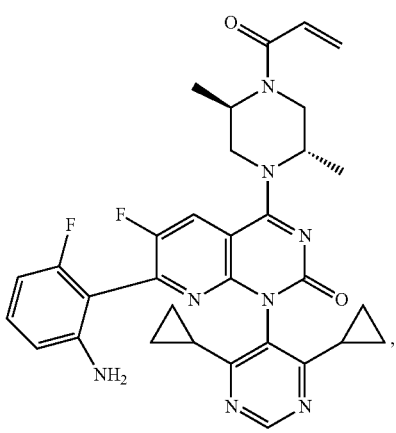 [SMILES: C=CC(=O)N1C[C@H](C)N(c2nc(=O)n(-c3c(C4CC4)ncnc3C3CC3)c3nc(-c4c(N)cccc4F)c(F)cc23)C[C@H]1C]

wherein the crystalline form is crystalline Form A, Form B, Form C, or Form D, wherein the crystalline Form A is characterized by an X-ray powder diffraction (XRPD) pattern having one or more of the following peaks: 6.2, 12.6, 14.8, and 19.9 degrees 2 theta, ±0.2°; Form B is characterized by an X-ray powder diffraction (XRPD) pattern having one or more of the following peaks: 6.2, 12.6, 14.8, 19.0, and 19.8 degrees 2 theta, ±0.2°; Form C is characterized by an X-ray powder diffraction (XRPD) pattern having one or more of the following peaks: 6.2, 12.5, and 19.9 degrees 2 theta, ±0.2°; and Form D is characterized by an X-ray powder diffraction (XRPD) pattern having one or more of the following peaks: 5.6, 11.2, 16.9, and 22.6 degrees 2 theta, ±0.2°.

10. The crystalline form of claim 9, which is crystalline Form A, characterized by an X-ray powder diffraction (XRPD) pattern having the following peaks: 6.2, 12.6, 14.8, and 19.9 degrees 2 theta, ±0.2°.

11. The crystalline form of claim 9, which is crystalline Form B, characterized by an X-ray powder diffraction (XRPD) pattern having the following peaks: 6.2, 12.6, 14.8, 19.0, and 19.8 degrees 2 theta, ±0.2°.

12. The crystalline form of claim 9, which is crystalline Form C, characterized by an X-ray powder diffraction (XRPD) pattern having the following peaks: 6.2, 12.5, and 19.9 degrees 2 theta, ±0.2°.

13. The crystalline form of claim 9, which is crystalline Form D, characterized by an X-ray powder diffraction (XRPD) pattern having the following peaks: 5.6, 11.2, 16.9, and 22.6 degrees 2 theta, ±0.2°.

14. The crystalline form of claim 9, which is substantially pure.

15. A pharmaceutical composition comprising the crystalline form of claim 9, and optionally a pharmaceutically acceptable excipient.

16. The crystalline form of claim 9, which is crystalline Form A, characterized by an X-ray powder diffraction (XRPD) pattern having the following peaks: 6.2, 12.6, 13.8, 14.8, 15.1, 18.0, 19.6 and 19.9 degrees 2 theta, ±0.2°.

17. The crystalline form of claim 9, which is crystalline Form A, characterized by an X-ray powder diffraction (XRPD) pattern substantially the same as shown in FIG. 5A.

18. The crystalline form of claim 9, which is crystalline Form B, characterized by an X-ray powder diffraction (XRPD) pattern having the following peaks: 6.2, 12.6, 13.6, 14.5, 14.8, 17.8, 19.0, 19.8, 21.4, 26.3, 31.9 and 38.6 degrees 2 theta, ±0.2°.

19. The crystalline form of claim 9, which is crystalline Form B, characterized by an X-ray powder diffraction (XRPD) pattern substantially the same as shown in FIG. 6A.

20. The crystalline form of claim 9, which is crystalline Form C, characterized by an X-ray powder diffraction (XRPD) pattern having the following peaks: 6.2, 6.8, 7.3, 12.5, 14.2, 14.7, 15.7, 16.3, 19.9, 21.2, 22.9 and 26.1 degrees 2 theta, ±0.2°.

21. The crystalline form of claim 9, which is crystalline Form C, characterized by an X-ray powder diffraction (XRPD) pattern substantially the same as shown in FIG. 7A.

22. The crystalline form of claim 9, which is crystalline Form D, characterized by an X-ray powder diffraction (XRPD) pattern having the following peaks: 5.6, 11.2, 15.8, 16.1, 16.9, 21.4, 22.6 and 34.3 degrees 2 theta, ±0.2°.

23. The crystalline form of claim 9, which is crystalline Form D, characterized by an X-ray powder diffraction (XRPD) pattern substantially the same as shown in FIG. 8A.

* * * * *